(12) United States Patent
Sakai et al.

(10) Patent No.: US 9,075,063 B2
(45) Date of Patent: Jul. 7, 2015

(54) METHYLATION ANALYSIS TO DETERMINE THE PRESENCE OF CANCER CELLS

(75) Inventors: Ayako Sakai, Kobe (JP); Atsushi Kaneda, Bunkyo-ku (JP); Kouichi Yagi, Bunkyo-ku (JP); Hiroyuki Aburatani, Bunkyo-ku (JP)

(73) Assignees: THE UNIVERSITY OF TOKYO, Tokyo (JP); SYSMEX CORPORATION, Hyogo (JP)

( * ) Notice: Subject to any disclaimer, the term of this patent is extended or adjusted under 35 U.S.C. 154(b) by 44 days.

(21) Appl. No.: 13/341,805

(22) Filed: Dec. 30, 2011

(65) Prior Publication Data

US 2012/0178634 A1 Jul. 12, 2012

Related U.S. Application Data

(63) Continuation of application No. PCT/JP2010/061164, filed on Jun. 30, 2010.

(30) Foreign Application Priority Data

Jul. 3, 2009 (JP) ................................ 2009-158873

(51) Int. Cl.
*C12Q 1/68* (2006.01)
*G01N 33/574* (2006.01)

(52) U.S. Cl.
CPC ........ *G01N 33/57419* (2013.01); *C12Q 1/6886* (2013.01); *C12Q 2600/154* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | | |
|---|---|---|---|---|
| 2004/0072197 A1* | 4/2004 | Jones et al. | ...................... | 435/6 |
| 2006/0292564 A1* | 12/2006 | Maier | .............................. | 435/6 |
| 2010/0273151 A1* | 10/2010 | Tapscott et al. | .................. | 435/6 |

FOREIGN PATENT DOCUMENTS

| | | |
|---|---|---|
| JP | 2001-165933 A | 6/2001 |
| JP | 2005-069846 A | 3/2005 |
| WO | WO 2004-020662 A2 | 3/2004 |
| WO | WO 2008009365 A2 * | 1/2008 |

OTHER PUBLICATIONS

Christensen et al. Aging and environmental exposures alter tissue-specific DNA methylation dependent upon CpG island context. PLOS Genetics, vol. 5, No. 8, e1000602, doi: 10.1371/journal.pgen.100602, Aug. 14, 2009, printed as pp. 1/13-13/13.*
Brennan et al. Comparative analysis of dna methylation profiles in peripheral blood leukocytes versus lymphoblastoid cell lines. Epigenetics, vol. 4, No. 3, pp. 159-164, Apr. 2009.*
Bonazzi et al. Identification of candidate tumor suppressor genes inactivated by promoter methylation in melanoma. Genes, Chromosomes & Cancer, vol. 48, pp. 10-21, 2009, published online Sep. 19, 2008.*
Andrew P. Feinberg, et al., "Perspectives", Nature Reviews, Cancer, Feb. 2004, pp. 143-153, vol. 4.
C. Richard Boland, et al., "A National Cancer institute Workshop on Microsatellite Instability for Cancer Detection and Familial Predisposition: Development of International Criteria for the Determination of Microsatellite Instability in Colorectal Cancer", Cancer Research, Nov. 15, 1998, vol. 58, pp. 5248-5257 vol. 58.
Daiji Oka, MD., et al, "The Presence of Aberrant DNA Methylation in Noncancerous Esophageal Mucosae in Association With Smoking History. A Target for Risk Diagnosis and Prevention of Esophageal Cancers.", Cancer, May 26, 2009, pp. 3412-3426, vol. 115, No. 15.
GDS2251/204513_s_at/ELMO1/*Homo sapiens*, Comparison of myeloid leukemia cells to normal monocytes. Transcriptional status of each gene compared to its CpG methylation state. The methylation of CpG islands is associated with transcriptional repression and, in cancer, leads to the abnormal silencing of tumor suppressor genes. '2006, 2 pages.
GDS2251/209343_AT/EFHD1/*Homo sapiens*, Comparison of myeloid leukemia cells to normal monocytes. Transcriptional status of each gene compared to its CpG methylation state. The methylation of CpG islands is associated with transcriptional repression and, in cancer, leads to the abnormal silencing of tumor suppressor genes. '2006, 2 pages.
GDS2251/214345_at/EDIL3/*Homo sapiens*, Comparison of myeloid leukemia cells to normal monocytes. Transcriptional status of each gene compared to its CpG methylation state. The methylation of CpG islands is associated with transcriptional repression and, in cancer, leads to the abnormal silencing of tumor suppressor genes. '2006, 2 pages.
GDS2251/226822_at/STOX2/*Homo sapiens*, Comparison of myeloid leukemia cells to normal monocytes. Transcriptional status of each gene compared to its CpG methylation state. The methylation of CpG islands is associated with transcriptional repression and, in cancer, leads to the abnormal silencing of tumor suppressor genes. '2006, 2 pages.
GDS2609/205082_s_at/AOXI/*Homo sapiens*, "Analysis of normal-appearing colonic mucosa of early onset colorectal cancer (CRC) patients without a prior family history of CRC. Results provide insight into the molecular pathogenesis of early onset CRC.", 2007, 4 pages.
Hiroshi Hayashi, et al., "High-resolution mapping of DNA methylation in human genome using oligonucleotide tiling array", Hum. Genet., 2007, pp. 701-711, vol. 120.

(Continued)

*Primary Examiner* — Jennifer Dunston
(74) *Attorney, Agent, or Firm* — Sughrue Mion, PLLC

(57) ABSTRACT

The present invention relates to a method for determination of the presence or absence of cancer cells in a biological sample or a method for determination of the prognosis of a colorectal cancer patient based on a result obtained by extracting DNA from a biological sample and analyzing methylation status of a marker gene in the DNA.

4 Claims, 12 Drawing Sheets

(56) References Cited

OTHER PUBLICATIONS

Manel Esteller, "Cancer epigenomics: DNA methylomes and histone-modification maps", Nature Review Genetics, Apr. 2007, pp. 286-298, vol. 8.

Marcel W. Coolen, et al., "Genomic profiling of CpG methylation and allelic specificity using quantitative high-throughput mass spectrometry: critical evaluation and improvements", Nucleic Acids Research, 2007, pp. 1-14, vol. 35, No. 18.

Mathias Ehrich, et al., "Quantitative high-throughput analysis of DNA methylation patterns by base-specific cleavage and mas spectrometry", PNAS, pp. 15785-15790, Nov. 1, 2005, vol. 102, No. 44.

Naohide Oue, et al., "Accumulation of DNA Methylation is Associated with Tumor Stage in Gastric Cancer", Cancer, 2006, pp. 1250-1259, vol. 106, No. 6.

Peter A. Jones, et al., "The Epigenomics of Cancer", Cell, Feb. 23, 2007, pp. 683-692, vol. 128.

S. Popat, "Systematic Review of Microsatellite instability and Colorectal Cancer Prognosis", Journal of Clinical Oncology, Jan. 20, 2005, pp. 609-618, vol. 23, No. 3.

Teresa Gomez Del Pulgar, et al., "Cdc42 is highly expressed in colorectal adenocarcinoma and downregulates ID4 through an epigenetic mechanism", International Journal of Oncology, 2008, pp. 185-193, vol. 33, No. 1.

Definition *Homo sapiens* dual specificity phosphatase 26 (putative) (DUSP26), mRNA., Database DDBJ/EMBL/GneBank [online], Feb. 22, 2009, URL, http://www.ncbi.nlm.nih.gov/nuccore/13128967?sat=13&satkey=8954120, [retrieved Jan. 13, 2015], 3 pages total.

Definition *Homo sapiens* myocardin (MYOCD), transcript variant 3, mRNA., Database DDBJ/EMBL/GenBank [online], May 17, 2009, URL, http://www.ncbi.nlm.nih.gov/nuccore/226423890?sat=13&satkey=4940342, [retrieved Jan. 13, 2015], 5 pages total.

* cited by examiner

SEQUENCE LISTING

```
<160> NUMBER OF SEQ ID NOS: 134

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
gaatagtygt tataatagtt gggata                                        26

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
acacctcaaa acraatacac ttaac                                         25

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gtttttgggg gttttaatgt                                               20

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ctccracacc actaactcct c                                             21

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
agaygtaaga gggtgtgata taga                                          24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
aaaaaataac raacacctaa aacc                                          24

<210> SEQ ID NO 7
<211> LENGTH: 24
<212> TYPE: DNA
<213> ORGANISM: Artificial Sequence
```

<220> FEATURE:
<223> OTHER INFORMATION: primer

<400> SEQUENCE: 7
tttggagtta ttaggaatgt atta                                    24

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
tcctccracc ctttttatct a                                       21

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
ggttattttt gattttgatt agg                                     23

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
caaaatcctt aaaacttcca at                                      22

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
ggttgaygtt agaattgaag aag                                     23

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
cccacctaaa cctaaaaact c                                       21

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
ggttatttta tttggatggt gt                                      22

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
aactacctaa acaactacct cctac                                       25

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tagygtagga tgagggaggt                                             20

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
crccttatac aaactaaaac tacac                                       25

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
ttttgtaatt ggtgtagttt tga                                         23

<210> SEQ ID NO 18
<211> LENGTH: 25
<212> TYPE: DNA
<213> ORGANISM: Artificial Sequence
<220> FEATURE:
<223> OTHER INFORMATION: primer

<400> SEQUENCE: 18
actattttta aaccataaca cacac                                       25

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
ataaagygtt gaggaaagag aa                                          22

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
ctctactcaa actttacaaa cact                                          24

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
taggagttgg ttagaagttg g                                             21

<210> SEQ ID NO 22
<211> LENGTH: 26
<212> TYPE: DNA
<213> ORGANISM: Artificial Sequence
<220> FEATURE:
<223> OTHER INFORMATION: primer

<400> SEQUENCE: 22
acractaatt ctcttttatc ttatca                                        26

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ggyggagtgt tgtagagttt                                               20

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
ccaactcctc actaaccata ac                                            22

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
aatgtgtttt tggttagtag gag                                           23

<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26
aaataactct acctctatcc tatacc                                        26

<210> SEQ ID NO 27

```
<211> LENGTH: 24
<212> TYPE: DNA
<213> ORGANISM: Artificial Sequence
<220> FEATURE:
<223> OTHER INFORMATION: primer

<400> SEQUENCE: 27
ggagtagtag tagataattt aggg                                          24

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
taactaacaa tataacacca aaac                                          24

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
ggatattgga aagttgtaaa ag                                            22

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ccrccctctc tcttactaac                                               20

<210> SEQ ID NO 31
<211> LENGTH: 25
<212> TYPE: DNA
<213> ORGANISM: Artificial Sequence
<220> FEATURE:
<223> OTHER INFORMATION: primer

<400> SEQUENCE: 31
gtagaggata aatgaggagt tagag                                         25

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tccctttcca aattcatacc                                               20

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
```
gggaaagttt atagtggaga gag                                              23

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
caaatcatca ctccttaaaa atc                                              23

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
gggtttggag tggttagtta                                                  20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
crctccctca acaacctaat                                                  20

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
gagaaggtta ttatttaggt tagtaa                                           26

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
actaccaact ctttccctcc                                                  20

<210> SEQ ID NO 39
<211> LENGTH: 22
<212> TYPE: DNA
<213> ORGANISM: Artificial Sequence
<220> FEATURE:
<223> OTHER INFORMATION: primer

<400> SEQUENCE: 39
gttagyggtt ttagaagagg tt                                               22

<210> SEQ ID NO 40
<211> LENGTH: 21
<212> TYPE: DNA

```
<213> ORGANISM: Artificial Sequence
<220> FEATURE:
<223> OTHER INFORMATION: primer

<400> SEQUENCE: 40
crcccactat acctacctac c                                              21

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
gaggaggagt tggtttttg                                                 20

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
aatctcttct acccccata c                                               21

<210> SEQ ID NO 43
<211> LENGTH: 23
<212> TYPE: DNA
<213> ORGANISM: Artificial Sequence
<220> FEATURE:
<223> OTHER INFORMATION: primer

<400> SEQUENCE: 43
ggygggaaaa agaaggtttt ata                                            23

<210> SEQ ID NO 44
<211> LENGTH: 26
<212> TYPE: DNA
<213> ORGANISM: Artificial Sequence
<220> FEATURE:
<223> OTHER INFORMATION: primer

<400> SEQUENCE: 44
acccraaaac aaatattcca aaatac                                         26

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
tggtattgtt tggtggagat                                                20

<210> SEQ ID NO 46
<211> LENGTH: 23
<212> TYPE: DNA
<213> ORGANISM: Artificial Sequence
<220> FEATURE:
<223> OTHER INFORMATION: primer

<400> SEQUENCE: 46
aaactcaaca aactaaacac cta                                            23
```

```
<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
gaggaaagaa ggaagggttg                                            20

<210> SEQ ID NO 48
<211> LENGTH: 26
<212> TYPE: DNA
<213> ORGANISM: Artificial Sequence
<220> FEATURE:
<223> OTHER INFORMATION: primer

<400> SEQUENCE: 48
aatacaaaat crtctctacc aatacc                                     26

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
ggttttaggg agaagaagtt                                            20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
racctacctc ccaacataaa                                            20

<210> SEQ ID NO 51
<211> LENGTH: 21
<212> TYPE: DNA
<213> ORGANISM: Artificial Sequence
<220> FEATURE:
<223> OTHER INFORMATION: primer

<400> SEQUENCE: 51
tygtaggaat gttttttttt g                                          21

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
ctctttccct tcacatttca                                            20

<210> SEQ ID NO 53
<211> LENGTH: 21
<212> TYPE: DNA
<213> ORGANISM: Artificial Sequence
<220> FEATURE:
```

<223> OTHER INFORMATION: primer

<400> SEQUENCE: 53
atggatgagt gaatgaatga a                                              21

<210> SEQ ID NO 54
<211> LENGTH: 21
<212> TYPE: DNA
<213> ORGANISM: Artificial Sequence
<220> FEATURE:
<223> OTHER INFORMATION: primer

<400> SEQUENCE: 54
acraaaacct aaaacaaaca c                                              21

<210> SEQ ID NO 55
<211> LENGTH: 22
<212> TYPE: DNA
<213> ORGANISM: Artificial Sequence
<220> FEATURE:
<223> OTHER INFORMATION: primer

<400> SEQUENCE: 55
gygatgttta gatagttttt tg                                             22

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
accacaactc caaaccttac                                                20

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
atygtttttg ttttgtttt g                                               21

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
aacactaata accccctacc                                                20

<210> SEQ ID NO 59
<211> LENGTH: 25
<212> TYPE: DNA
<213> ORGANISM: Artificial Sequence
<220> FEATURE:
<223> OTHER INFORMATION: primer

<400> SEQUENCE: 59
gttttgtttt ttaaggggtg ttgag                                          25

```
<210> SEQ ID NO 60
<211> LENGTH: 25
<212> TYPE: DNA
<213> ORGANISM: Artificial Sequence
<220> FEATURE:
<223> OTHER INFORMATION: primer

<400> SEQUENCE: 60
acactaactc craaaactac aaaac                                          25

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
ggtattygtt ttttagattg tt                                             22

<210> SEQ ID NO 62
<211> LENGTH: 21
<212> TYPE: DNA
<213> ORGANISM: Artificial Sequence
<220> FEATURE:
<223> OTHER INFORMATION: primer

<400> SEQUENCE: 62
aaataaatcc cacctctaca t                                              21

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
gaggaggaag aggaggtgat                                                20

<210> SEQ ID NO 64
<211> LENGTH: 22
<212> TYPE: DNA
<213> ORGANISM: Artificial Sequence
<220> FEATURE:
<223> OTHER INFORMATION: primer

<400> SEQUENCE: 64
aaaatctaaa tcccaaacac aa                                             22

<210> SEQ ID NO 65
<211> LENGTH: 22
<212> TYPE: DNA
<213> ORGANISM: Artificial Sequence
<220> FEATURE:
<223> OTHER INFORMATION: primer

<400> SEQUENCE: 65
tgttaggtat agagtaggtg gt                                             22

<210> SEQ ID NO 66
<211> LENGTH: 21
<212> TYPE: DNA
<213> ORGANISM: Artificial Sequence
<220> FEATURE:
<223> OTHER INFORMATION: primer
```

<400> SEQUENCE: 66
caacrctatt ttatttcctc c                                         21

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
ggttttaggt tggggtagtt                                           20

<210> SEQ ID NO 68
<211> LENGTH: 26
<212> TYPE: DNA
<213> ORGANISM: Artificial Sequence
<220> FEATURE:
<223> OTHER INFORMATION: primer

<400> SEQUENCE: 68
cctacacata catactccta cttact                                    26

<210> SEQ ID NO 69
<211> LENGTH: 25
<212> TYPE: DNA
<213> ORGANISM: Artificial Sequence
<220> FEATURE:
<223> OTHER INFORMATION: primer

<400> SEQUENCE: 69
tagttttttt tattaggatt ttttt                                     25

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
cccaaacata ttacccaaac                                           20

<210> SEQ ID NO 71
<211> LENGTH: 24
<212> TYPE: DNA
<213> ORGANISM: Artificial Sequence
<220> FEATURE:
<223> OTHER INFORMATION: primer

<400> SEQUENCE: 71
atgtttagtt atttttgatt ggtt                                      24

<210> SEQ ID NO 72
<211> LENGTH: 23
<212> TYPE: DNA
<213> ORGANISM: Artificial Sequence
<220> FEATURE:
<223> OTHER INFORMATION: primer

<400> SEQUENCE: 72
rctcaacaca actctaacaa cac                                       23

<210> SEQ ID NO 73
<211> LENGTH: 23

```
<212> TYPE: DNA
<213> ORGANISM: Artificial Sequence
<220> FEATURE:
<223> OTHER INFORMATION: primer

<400> SEQUENCE: 73
tatttaggga ttgggtttag ttt                                              23

<210> SEQ ID NO 74
<211> LENGTH: 22
<212> TYPE: DNA
<213> ORGANISM: Artificial Sequence
<220> FEATURE:
<223> OTHER INFORMATION: primer

<400> SEQUENCE: 74
cctccttaca tccttacacc tc                                               22

<210> SEQ ID NO 75
<211> LENGTH: 24
<212> TYPE: DNA
<213> ORGANISM: Artificial Sequence
<220> FEATURE:
<223> OTHER INFORMATION: primer

<400> SEQUENCE: 75
gggtagaatt tagtttgagt aggt                                             24

<210> SEQ ID NO 76
<211> LENGTH: 21
<212> TYPE: DNA
<213> ORGANISM: Artificial Sequence
<220> FEATURE:
<223> OTHER INFORMATION: primer

<400> SEQUENCE: 76
aactcccact cccttacact a                                                21

<210> SEQ ID NO 77
<211> LENGTH: 22
<212> TYPE: DNA
<213> ORGANISM: Artificial Sequence
<220> FEATURE:
<223> OTHER INFORMATION: primer

<400> SEQUENCE: 77
ggaagagatg aaatggtagt at                                               22

<210> SEQ ID NO 78
<211> LENGTH: 22
<212> TYPE: DNA
<213> ORGANISM: Artificial Sequence
<220> FEATURE:
<223> OTHER INFORMATION: primer

<400> SEQUENCE: 78
tcaaaaacac rctataaccc ta                                               22

<210> SEQ ID NO 79
<211> LENGTH: 22
<212> TYPE: DNA
<213> ORGANISM: Artificial Sequence
<220> FEATURE:
<223> OTHER INFORMATION: primer

<400> SEQUENCE: 79
```

```
yggtagaaat agtttaggga ag                                              22

<210> SEQ ID NO 80
<211> LENGTH: 23
<212> TYPE: DNA
<213> ORGANISM: Artificial Sequence
<220> FEATURE:
<223> OTHER INFORMATION: primer

<400> SEQUENCE: 80
tactccatac actcaaaaaa cac                                             23

<210> SEQ ID NO 81
<211> LENGTH: 24
<212> TYPE: DNA
<213> ORGANISM: Artificial Sequence
<220> FEATURE:
<223> OTHER INFORMATION: primer

<400> SEQUENCE: 81
tttatttygt tgttatggtg ttta                                            24

<210> SEQ ID NO 82
<211> LENGTH: 19
<212> TYPE: DNA
<213> ORGANISM: Artificial Sequence
<220> FEATURE:
<223> OTHER INFORMATION: primer

<400> SEQUENCE: 82
cctaacccct ttccctaac                                                  19

<210> SEQ ID NO 83
<211> LENGTH: 60
<212> TYPE: DNA
<213> ORGANISM: Artificial Sequence
<220> FEATURE:
<223> OTHER INFORMATION: primer

<400> SEQUENCE: 83
gcattagcgg ccgcgaaatt aatacgactc actatgggga gaaaaaaaaa aaaaaaaaab     60

<210> SEQ ID NO 84
<211> LENGTH: 4949
<212> TYPE: DNA
<213> ORGANISM: Homo sapiens

<400> SEQUENCE: 84
cgccccactc ggcgggtcgg tgccgccggg tccaggtgc ccgctacttc ccagaaccctc     60 cgcctcccgc tccgggccct cgaaccagcg cggacaccac aatggaccgg gcgtccgagc    120
tgctcttcta cgtgaacggc cgcaaggtga tagaaaaaaa tgtcgatcct gaaacaatgc    180
tgttgcctta tttgaggaag aagcttcgac tcacaggaac taagtatggc tgtgtggagag   240 gaggctgtgg tgcttgtaca gtgatgatat cacgatacaa ccccatcacc aagaggataa    300
ggcatcaccc agccaatgcc tgtctgattc ccatctgttc tctgtatggt gctgccgtca    360
ccacagtaga aggcatagga agcacccaca ccagaattca tcctgttcag gagaggattg    420
ccaagtgtca tggcacccag tgtggcttct gcacacctgg gatggtgatg tccatctaca    480
cgctgctcag gaaccaccca gagcccactc tggatcagtt aactgatgcc cttggtggta    540
acctgtgccg ttgcactgga tacaggccca taattgatgc atgcaagact ttctgtaaaa    600
cttcgggctg ctgtcaaagt aaagaaaatg gggtttgctg tttggatcaa ggaatcaatg    660
```

-continued

```
gattgccaga atttgaggaa ggaagtaaga caagtccaaa actcttcgca gaagaggagt    720
ttctgccatt ggatccaacc caggaactga tatttcctcc tgagctaatg ataatggctg    780
agaaacagtc gcaaaggacc agggtgtttg gcagtgagag aatgatgtgg ttttcccccg    840
tgaccctgaa ggaactgctg gaatttaaat tcaagtatcc ccaggctcct gttatcatgg    900
gaaacacctc tgtggggcct gaagtgaaat ttaaaggcgt ctttcaccca gttataattt    960
ctcctgatag aattgaagaa ctgagtgttg taaaccatgc atataatgga ctcacccttg   1020
gtgctggtct cagcctagcc caggtgaagg acattttggc tgatgtagtc cagaagcttc   1080
cagaggagaa gacacagatg taccatgctc tcctgaagca tttgggaact ctggctgggt   1140
cccagatcag gaacatggct tctttagggg gacacatcat tagcaggcat ccagattcag   1200
atctgaatcc catcctggct gtgggtaact gtacccctcaa cttgctatca aaagaaggaa   1260
aacgacagat tcctttaaat gagcaattcc tcagcaagtg ccctaatgca gatcttaagc   1320
ctcaagaaat cttggtctca gtgaacatcc cctactcaag gaagtgggaa tttgtgtcag   1380
ccttccgaca agcccagcga caggagaatg cgctagcgat agtcaattca ggaatgagag   1440
tcttttttgg agaaggggat ggcattatta gagagttatg catctcatat ggaggcgttg   1500
gtccagccac catctgtgcc aagaattcct gccagaaact cattggaagg cactggaacg   1560
aacagatgct ggatatagcc tgcaggctta ttctgaatga agtctccctt ttgggctcgg   1620
cgccaggtgg gaaagtggag ttcaagagga ctctcatcat cagcttcctc ttcaagttct   1680
acctggaagt gtcacagatt tgaaaaaga tggatccagt tcactatcct agccttgcag   1740
acaagtatga aagtgctttta gaagatcttc attccaaaca tcactgcagt acattaaagt   1800
accagaatat aggcccaaag cagcatcctg aagacccaat tggccacccc atcatgcatc   1860
tgtctggtgt gaagcatgcc acgggggagg ccatctactg tgatgacatg cctctggtgg   1920
accaggaact tttcttgact tttgtgacta gttcaagagc tcatgctaag attgtgtcta   1980
ttgatctgtc agaagctctc agcatgcccg gtgtggtgga catcatgaca gcagaacatc   2040
ttagtgacgt caactccttc tgctttttta ctgaagctga gaaatttctg gcgacagata   2100
aggtgttctg tgtgggtcag cttgtctgtg ctgtgcttgc cgattctgag gttcaggcaa   2160
agcgagctgc taagcgagtg aagattgtct atcaagactt ggagccgctg atactaacaa   2220
ttgaggaaag tatacaacac aactcctcct tcaagccaga aaggaaactg aatatggaa    2280 atgttgacga agcatttaaa gtggttgatc aaattcttga aggtgaaata catatgggag   2340
gtcaagaaca ttttttatatg gaaacccaaa gcatgcttgt cgttcccaag ggagaggatc   2400
aagaaatgga tgtctacgtg tccacacagt ttcccaaata tatacaggac attgttgcct   2460
caaccttgaa gctcccagct aacaaggtca tgtgccatgt aaggcgtgtt ggtggagcgt   2520
ttggagggaa ggtgttaaaa accggaatca ttgcagccgt cactgcattt gccgcaaaca   2580
aacatggccg tgcagttcgc tgtgttctgg aacgaggaga agacatgtta ataactggag   2640
gccgccatcc ttaccttgga agtacaaagc tggattcat gaacgatggc agaatcttgg    2700
ccctggacat ggagcattac agcaatgcag gcgcctcctt ggatgaatca ttattcgtga   2760
tagaaatggg acttctgaaa atggacaatg cttacaagtt tcccaatctc cgctgccggg   2820
gttgggcatg cagaaccaac cttccatcca acacagcttt tcgtgggttt ggctttcctc   2880
aggcagcgct gatcaccgaa tcttgtatca cggaagttgc agccaaatgt ggactatccc   2940
ctgagaaggt gcgaatcata aacatgtaca aggaaattga tcaaacaccc tacaaacaag   3000
```

| | |
|---|---:|
| agatcaatgc caagaaccta atccagtgtt ggagagaatg tatggccatg tcttcctact | 3060 |
| ccttgaggaa agttgctgtg gaaaagttca atgcagagaa ttattggaag aagaaaggac | 3120 |
| tggccatggt cccctgaag tttcctgttg gccttggctc acgtgctgct ggtcaggctg | 3180 |
| ctgccttggt tcacatttat cttgatggct ctgtgctggt cactcacggt ggaattgaaa | 3240 |
| tggggcaggg ggtccacact aaaatgattc aggtggtcag ccgtgaatta agaatgccaa | 3300 |
| tgtcgaatgt ccacctgcgt ggaacaagca cagaaactgt ccctaatgca atatctctg | 3360 |
| gaggttctgt ggtggcagat ctcaacggtt tggcagtaaa ggatgcctgt caaactcttc | 3420 |
| taaaacgcct cgaacccatc atcagcaaga atcctaaagg aacttggaaa gactgggcac | 3480 |
| agactgcttt tgatgaaagc attaaccttt cagctgttgg atacttcaga ggttatgagt | 3540 |
| cagacatgaa ctgggagaaa ggcgaaggcc agcccttcga atactttgtt tatggagctg | 3600 |
| cctgttccga ggttgaaata gactgcctga cggggatca taagaacatc agaacagaca | 3660 |
| ttgtcatgga tgttggctgc agtataaatc cagccattga cataggccag attgaaggtg | 3720 |
| catttattca aggcatggga ctttatacaa tagaggaact gaattattct ccccagggca | 3780 |
| ttctgcacac tcgtggtcca gaccaatata aaatccctgc catctgtgac atgcccacgg | 3840 |
| agttgcacat tgctttgttg cctccttctc aaaactcaaa tactctttat tcatctaagg | 3900 |
| gtctgggaga gtcgggggtg ttcctggggt gttccgtgtt tttcgctatc catgacgcag | 3960 |
| tgagtgcagc acgacaggag agaggcctgc atggacccct gacccttaat agtccactga | 4020 |
| ccccggagaa gattaggatg gcctgtgaag acaagttcac aaaaatgatt ccgagagatg | 4080 |
| aacctggatc ctacgttcct tggaatgtac ccatctgaat caaatgcaaa cttctggaga | 4140 |
| aaacagagtg cctcttccca gatggcaatc tgtcctatct ctgtgctgga agatgctaga | 4200 |
| tctgaaagac agagtttcca cagttcagaa atcatcccac agtgttgctt ttctatggag | 4260 |
| ctgatttaaa gtattccatt tagatttgat agatatgctt aagcaatcta taaatcattt | 4320 |
| tcaatgttat aaacactaat tggtttcctc tagggtgata ttcgtcatta ctctgtctct | 4380 |
| tcaatccatc cagctaaatg gaataggtga tgacttgcat gtgactccta cttggcttct | 4440 |
| atccaccaac agaaattata ccatatagtg aaaggcaatt ttctaaataa tttcattact | 4500 |
| aatatgaact gtgaagttgt cattttttca tttgtccttt tctgctatca ccttcctctt | 4560 |
| gtcagaatga atatagacac tgtatctaag tgggaccaaa gaaaaaatag cgaactttca | 4620 |
| ccaaagttttt catgaaaacc caaaagcttt aaaagttact atcaagaaat tgaaaggaaa | 4680 |
| cccacagaat aggataaaat atttgtaaat catatatttg ataaaagtct tgtaaccaga | 4740 |
| tacataaaga gctcttacaa ctcaataaaa ggcaagtaat ttaaaaatag gcaaaagaat | 4800 |
| tgctggatgg tatggtagtt ctatttttag tttttacccct aactactctg acttgatcat | 4860 |
| ttaacattct gtgtatgtaa caaaatatca catgcataaa tattatgtat caataaaatt | 4920 |
| ttttaatggg caaaaaaaaa aaaaaaaa | 4949 |

<210> SEQ ID NO 85
<211> LENGTH: 6264
<212> TYPE: DNA
<213> ORGANISM: Homo sapiens

<400> SEQUENCE: 85

| | |
|---|---:|
| gagtgtggct gcagtgcgcc gggacaccag ggctccgcgc tccgcactca agaggctccc | 60 |
| gcgtcccaac ccctcgcgcc cgcgcgttcg cggatccagg ccgaggaccg aaaggggccc | 120 |
| cccgagcccc cggggccggc gcccagagag cccagcaagg ccggccgccc tgccggtgtg | 180 |

```
ccgccggcgg gtgcttctgg aagggccaat gcgttcgggc agcagcccct gaagccgagc    240
ccgaggctaa gtgggactga ccggggccca gagtggacga accgccagca tgggagaga    300 ccagcgcgcg gtggccggcc ctccctacg gcggtggctg ctgctgggga cagtgaccgt    360
ggggttcctc gcccagagcg tcttggcggg tgtgaagaag tttgatgtgc cgtgtggagg    420
aagagattgc agtggggggct gccagtgcta ccctgagaaa ggtggacgtg gtcagcctgg    480
gccagtgggc cccaggggt acaatgggcc accaggatta caaggattcc cgggactgca    540
gggacgtaaa ggagacaagg gtgaaagggg agccccggga gtaacgggac ccaagggcga    600
cgtgggagca agaggcgttt ctggattccc tggtgccgat ggaattcctg acacccggg    660 gcaaggtggg cccaggggaa ggccgggcta cgatggctgc aacggaaccc agggagactc    720
aggtccacag ggccccccg ctctgaggg gttcaccggg cctcccggc ccaaggacc    780 aaaagggcag aaaggtgagc cttatgcact gcctaaagag gagcgcgaca gatatcgggg    840
tgaacctgga gagcctggat tggtcggttt ccagggacct cccggccgcc ctgggcatgt    900
gggacagatg ggtccagttg gagctccagg gagaccagga ccacctggac ccctggacc    960 aaaaggacag caaggcaaca gaggacttgg tttctacgga gttaagggtg aaaagggtga    1020
cgtagggcag ccgggaccca acgggattcc atcagacacc ctccacccca tcatcgcgcc    1080
cacaggagtc accttccacc cagatcagta caagggtgaa aaaggcagtg aggggggaacc    1140 aggaataaga ggcatttcct tgaagggaga agaaggaatc atgggctttc ctggactgag    1200
gggttaccct ggcttgagtg gtgaaaaaagg atcaccagga cagaagggaa gccgaggcct    1260
ggatggctat caagggcctg atggaccccg gggacccaag ggagaagccg agacccagg    1320 gcccctgga ctacctgcct actcccctca cccttcccta gcaaaggtg ccagaggtga    1380 cccgggattc ccaggggccc aaggggagcc aggaagccag ggtgagccag gagacccggg    1440
cctcccaggt ccccctggcc tctccatcgg agatggagat cagaggagag gcctgccggg    1500
tgagatggga cccaagggct tcatcggaga ccccggcatc cctgcgctct acggggggccc    1560 acctggacct gatggaaagc gagggcctcc aggaccccc gggctcctg gaccaccgg    1620 acctgatggc ttcctgtttg ggctgaaagg agcaaaagga gagcaggct tccctgggct    1680 tcccggctcc cctggagccc gcggaccaaa ggggtggaaa ggtgacgctg gggaatgcag    1740
atgtacagaa ggcgacgaag ctatcaaagg tcttccggga ctgccaggac ccaagggctt    1800
cgcaggcatc aacggggagc cggggaggaa aggggacaga ggagaccccg ccaacacgg    1860 cctccctggg ttcccaggggc tcaagggagt gcctggcaac attggtgctc ccggacccaa    1920
aggagcaaaa ggagattcca gaacaatcac aaccaaaggt gagcggggac agcccggcgt    1980
cccaggtgtg cccgggatga aggtgacga tggcagccca ggccgcgatg ggctcgatgg    2040
attccccggc ctcccaggcc ctccggtga tggcatcaag ggccctccag ggacccagg    2100 ctatccagga atacctggaa cgaagggtac tccaggagaa atgggccccc caggactggg    2160
ccttcccggc ctcaaaggcc aacgtggttt ccctggagac gccggcttac ctggaccacc    2220
aggcttcctg ggccctcctg gccccgcagg gaccccagga caaatagatt gtgacacaga    2280
tgtgaaaagg gccgttggag gtgacagaca ggaggccatc cagccaggtt gcataggagg    2340
gcccaaggga ttgccaggcc tgccaggacc ccaggcccc acaggtgcca aaggcctccg    2400
aggaatccca ggcttcgcag gagctgatgg aggaccaggg cccaggggct tgccaggaga    2460
cgcaggtcgt gaagggttcc caggaccccc agggttcata ggaccccgag gatccaaagg    2520
```

```
tgcagtgggc ctccctggcc cagatggatc cccaggtccc atcggcctgc cagggccaga    2580
tgggccccct ggggaaaggg gcctccctgg agaagtcctg ggagctcagc ccgggccacg    2640
gggagatgct ggtgtgcctg acagcctggg cttaaaggc cttcccggag acagaggccc     2700
ccctggattc agaggaagcc aagggatgcc tgggatgcca gggctgaagg gccagccagg    2760
cctcccagga ccttccggcc agccaggcct gtatgggcct ccaggactgc atggattccc    2820
aggagctcct ggccaagagg ggcccttggg gctgccagga atcccaggcc gtgaaggtct    2880
gcctggtgat agaggggacc ctggggacac aggcgctcct ggccctgtgg gcatgaaagg    2940
tctctctggt gacagaggag atgctggctt cacaggggag caaggccatc caggaagccc    3000
tggatttaaa ggaattgatg gaatgcctgg gacccccggg ctaaaaggag atagaggctc    3060
acctgggatg gatggtttcc aaggcatgcc tggactcaaa gggagacccg ggtttccagg    3120
gagcaaaggc gaggctggat ttttcggaat acccggtctg aagggtctgg ctggtgagcc    3180
aggttttaaa ggcagccgag ggaccctgg gcccccagga ccacctcctg tcatcctgcc     3240
aggaatgaaa gacattaaag gagagaaagg agatgaaggg cctatggggc tgaaaggata    3300
cctgggcgca aaaggtatcc aaggaatgcc aggcatccca gggctgtcag gaatccctgg    3360
gctgcctggg aggcccggcc acatcaaagg agtcaaggga gacatcggag tccccggcat    3420
ccccggtttg ccaggattcc ctggggtggc tggccccccct ggaattacgg gattcccagg   3480
attcatagga agccggggtg acaaaggtgc cccaggagga gcaggcctgt atggcgagat    3540
tggcgcgact ggtgatttcg gtgacatcgg ggacactata aatttaccag gaagaccagg    3600
cctgaagggg gagcggggca ccactggaat accaggtctg aagggattct ttggagagaa    3660
gggaacagaa ggtgacatcg gcttccctgg gataacaggc gtgactggag tccaaggccc    3720
tcctggactt aaaggacaaa caggctttcc agggctgact gggcctccag ggtcgcaggg    3780
agagctgggg cggattggac tgcctggtgg caaaggagat gatggctggc cgggagctcc    3840
gggcttacca ggttttccgg gactccgtgg gatccgcgc ttacacggct tgccaggcac    3900
caagggcttt ccaggatccc caggttctga catccacgga gacccaggct tcccaggccc    3960
tcctggggaa agaggtgacc caggagaggc caacaccctt ccaggccctg tgggagtccc    4020
aggacagaaa ggagaccaag gagctccagg ggaacgaggc ccacctggga gcccaggact    4080
tcaggggttc ccaggcatca caccccttc caacatctct ggggcacctg gtgacaaagg    4140
ggcgccaggg atatttggcc tgaaaggtta tcggggccca ccagggccac caggttctgc    4200
tgctcttcct ggaagcaaag gtgacacagg gaacccagga gctccaggaa ccccagggac    4260
caaaggatgg gccggggact ccgggcccca gggcaggcct ggtgtgtttg gtctcccagg    4320
agaaaaaggg cccaggggtg aacaaggctt catgggggaac actggaccca ccggggcggt    4380
gggcgacaga ggccccaagg gacccaaggg agacccagga ttccctggtg cccccgggac    4440
tgtgggagcc cccgggattg caggaatccc ccagaagatt gccgtccaac cagggacagt    4500
gggtccccag gggaggcgag gccccctgg ggcaccgggg gagatggggc cccagggccc     4560
ccccggagaa ccaggtttttc gtggggctcc agggaaagct gggccccaag gaagaggtgg    4620
tgtgtctgct gttcccggct ccgggagga tgaaggaccc ataggccacc agggccgat     4680 tggccaagaa ggtgcaccag gccgtccagg gagcccgggc ctgccgggta tgccaggccg    4740
cagcgtcagc atcggctacc tcctggtgaa gcacagccag acggaccagg agcccatgtg    4800
cccagtgggc atgaacaaac tctggagtgg atacagcctg ctgtacttcg agggccagga    4860
gaaggcgcac aaccaggacc tggggctggc gggctcctgc ctggcgcggt tcagcaccat    4920
```

```
gcccttcctg tactgcaacc ctggtgatgt ctgctactat gccagccgga acgacaagtc    4980
ctactggctc tctaccactg cgccgctgcc catgatgccc gtggccgagg acgagatcaa    5040
gccctacatc agccgctgtt ctgtgtgtga ggccccggcc atcgccatcg cggtccacag    5100
tcaggatgtc tccatcccac actgcccagc tgggtggcgg agtttgtgga tcggatattc    5160
cttcctcatg cacacggcgg cgggagacga aggcggtggc caatcactgg tgtcaccggg    5220
cagctgtcta gaggacttcc gcgccacacc attcatcgaa tgcaatggag gccgcggcac    5280
ctgccactac tacgccaaca agtacagctt ctggctgacc accattcccg agcagagctt    5340
ccagggctcg ccctccgccg acacgctcaa ggccggcctc atccgcacac acatcagccg    5400
ctgccaggtg tgcatgaaga acctgtgagc cggcgcgtgc caggaagggc cattttggtg    5460
cttattctta acttattacc tcaggtgcca acccaaaaat tggttttatt tttttcttaa    5520
aaaaaaaaaa gtctaccaaa ggaatttgca tccagcagca gcacttagac ctgccagcca    5580
ctgtcaccga gcgggtgcaa gcactcgggg tccctggagg gcaagccctg cccacagaaa    5640
gccaggagca gccctggccc ccatcagccc tgctagacgc accgcctgaa ggcacagcta    5700
accacttcgc acacacccat gtaaccactg cactttccaa tgccacagac aactcacatt    5760
gttcaactcc cttctcgggg tgggacagac gagacaacag cacacaggca gccagccgtg    5820
gccagaggct cgaggggctc agggcctcag gcaccgtcc ccacgcgagg gccccgtggg    5880
tgggcctggc cctgctttct acgccaatgt tatgccagct ccatgttctc ccaaataccg    5940
ttgatgtgaa ttatttttaaa ggcaaaaccg tgctctttat tttaaaaaac actgataatc    6000
acactgcggt aggtcattct tttgccacat ccctatagac cactgggttt ggcaaaactc    6060
aggcagaagt ggagacccttt ctagacatca ttgtcagcct tgctacttga aggtacaccc    6120
catagggtcg gaggtgctgt ccccactgcc ccacgttgtc cctgagattt aacccctcca    6180
ctgctggggg tgagctgtac tcttctgact gccccctcct gtgtaacgac tacaaaataa    6240
aacttggttc tgaatatttt taaa                                          6264
```

<210> SEQ ID NO 86
<211> LENGTH: 1665
<212> TYPE: DNA
<213> ORGANISM: Homo sapiens

<400> SEQUENCE: 86

```
gttggctggg gagcccacgc tgcctggcga ctcgggccac cgaatgtgag accgagtccc     60
tttatgtcac cagcgcacac gctgatttga accctgcttc gacgtgtgtg tcatggctta    120
aaaatagctg ctaatctgtc aacctgtctt gggcagaaac agcggcggcg acagcagcag    180
gagcgtcatg gccgtggcgc tgtctgcgcc ggcgatccgc ctttcggact gaggcccagc    240
gcagcgcttg caaagagcag cagctacctg gcaactgaac ccatcatcac cacagccact    300
cctgcagctg ccacggtttc tgccacctct aagatgtgcc ctggtaactg gctttgggct    360
tctatgactt ttatggcccg cttctcccgg agtagctcaa ggtctcctgt tcgaactcga    420
gggaccctgg aggagatgcc aaccgttcaa catccttttcc tcaatgtctt cgagttggag    480
cggctcctct acacaggcaa gacagccctgt aaccatgccg acgaggtctg gccaggcctc    540
tatctcggag accaggacat ggctaacaac cgccgggagc ttcgccgcct gggcatcacg    600
cacgtcctca atgcctcaca cagcggtgg cgaggcacgc ccgaggccta tgaggggctg    660
ggcatccgct acctgggtgt tgaggcccac gactcgccag cctttgacat gagcatccac    720
```

| | |
|---|---|
| ttccagacgg ctgccgactt catccaccgg gcgctgagcc agccaggagg gaagatcctg | 780 |
| gtgcattgtg ctgtgggcgt gagccgatcc gccaccctgg tactggccta cctcatgctg | 840 |
| taccaccacc ttaccctcgt ggaggccatc aagaaagtca agaccaccg aggcatcatc | 900 |
| cccaaccggg gcttcctgag gcagctcctg gccctggacc gcaggctgcg gcagggtctg | 960 |
| gaagcatgag gggagggga gagaggtcag gccaggcccg tgggtaggtc cctggctccc | 1020 |
| agctggagat aggaggccca ggtggcaggt agcaggaggc ccagatcacc catcctcccc | 1080 |
| tggggtcagg agaggccgag ccccaggcca ctgtcactct ttgtgggagg ggacggggag | 1140 |
| tgaggttggg cagtgtggtg gatgggcacc caggaagggt tgaccaggga aggaggcagc | 1200 |
| taggctgtag atggaagatg gtcctgggat tcgaacaccg ctgggatctg gccagggtgc | 1260 |
| tccctgggat tcacagtccc ttcccctctt tgtgcccaag tgtttccctc tctccctcac | 1320 |
| caaaacaaaa gggccatctc tgccctgcac ttgtgcagaa agtcagggat acggcaagca | 1380 |
| tgaatgcaat ggtgtagagt tgtgtgaaac ccctagcata gagacagaca gcgaagagat | 1440 |
| ggtgtgaaaa gcttgcagaa ccagacagag aaccccacac actttccact ccaagcacag | 1500 |
| gaggaggtag ctagcgtgtg agggttggca ctaggcccac ggctgctgct tgggccaaaa | 1560 |
| acatacagag gtgcatggct ggcagtcttg aaattgtcac tcgcttactg gatccaagcg | 1620 |
| tctcgaggat aaataaagat catgaaaaaa aaaaaaaaaa aaaaa | 1665 |

<210> SEQ ID NO 87
<211> LENGTH: 2974
<212> TYPE: DNA
<213> ORGANISM: Homo sapiens

<400> SEQUENCE: 87

| | |
|---|---|
| agaagccccg cagccgccgc gcggagaaca gcgacagccg agcgcccggt ccgcctgtct | 60 |
| gccggtgggt ctgcctgccc gcgcagcaga cccggggcgg ccgcgggagc ccgcgccccg | 120 |
| cccgccgcgc ctctgccggg acccaccccg agcggagggc tgagcccgcc ggcggctccc | 180 |
| cggagctcac ccacctccgc gcgccggagc gcaggcaaaa ggggaggaaa ggctcctctc | 240 |
| tttagtcacc actctccgcc tctccaagaa tttgtttaac aaagcgctga ggaaagagaa | 300 |
| cgtcttcttg aattctttag taggggcgga gtctgctgct gccctgcgct gccacctcgg | 360 |
| ctacactgcc ctccgcgacg acccctgacc agccggggtc acgtccggga gacgggatca | 420 |
| tgaagcgctc ggtagccgtc tggctcttgg tcgggctcag cctcggtgtc ccccagttcg | 480 |
| gcaaaggtga tatttgtgat cccaatccat gtgaaaatgg aggtatctgt ttgccaggat | 540 |
| tggctgatgg ttccttttcc tgtgagtgtc cagatggctt cacagacccc aactgttcta | 600 |
| gtgttgtgga ggttgcatca gatgaagaag aaccaacttc agcaggtccc tgcactccta | 660 |
| atccatgcca taatggagga acctgtgaaa taagtgaagc ataccgaggg gatacattca | 720 |
| taggctatgt ttgtaaatgt cccccgaggat ttaatgggat tcactgtcag cacaacataa | 780 |
| atgaatgcga agttgagcct tgcaaaaatg gtggaatatg tacagatctt gttgctaact | 840 |
| attcctgtga gtgcccaggc gaatttatgg aagaaattg tcaatacaaa tgctcaggcc | 900 |
| cactgggaat tgaaggtgga attatatcaa accagcaaat cacagcttcc tctactcacc | 960 |
| gagctctttt tggactccaa aaatggtatc cctactatgc acgtcttaat aagaaggggc | 1020 |
| ttataaatgc gtggacagct gcagaaatg acagatggcc gtggattcag ataaatttgc | 1080 |
| aaaggaaaat gagagttact ggtgtgatta cccaaggagc caagaggatt ggaagcccag | 1140 |
| agtatataaa atcctacaaa attgcctaca gtaatgatgg aaagacttgg gcaatgtaca | 1200 |

```
aagtgaaagg caccaatgaa gacatggtgt tcgtggaaa cattgataac aacactccat    1260
atgctaactc tttcacaccc cccataaaag ctcagtatgt aagactctat ccccaagttt    1320
gtcgaagaca ttgcactttg cgaatggaac ttcttggctg tgaactgtcg ggttgttctg    1380
agcctctggg tatgaaatca ggacatatac aagactatca gatcactgcc tccagcatct    1440
tcagaacgct caacatggac atgttcactt gggaaccaag gaaagctcgg ctggacaagc    1500
aaggcaaagt gaatgcctgg acctctggcc acaatgacca gtcacaatgg ttacaggtgg    1560
atcttcttgt tccaaccaaa gtgactggca tcattacaca aggagctaaa gattttggtc    1620
atgtacagtt tgttggctcc tacaaactgg cttacagcaa tgatggagaa cactggactg    1680
tataccagga tgaaaagcaa agaaaagata aggttttcca gggaaatttt gacaatgaca    1740
ctcacagaaa aaatgtcatc gaccctccca tctatgcacg acacataaga atccttcctt    1800
ggtcctggta cgggaggatc acattgcggt cagagctgct gggctgcaca gaggaggaat    1860
gaggggaggc tacatttcac aaccctcttc cctatttccc taaaagtatc tccatggaat    1920
gaactgtgca aaatctgtag gaaactgaat ggttttttt ttttttcat gaaaaagtgc    1980 tcaaattatg gtaggcaact aacggtgttt ttaagggggt ctaagcctgc cttttcaatg    2040
atttaatttg atttatttt atccgtcaaa tctcttaagt aacaacacat taagtgtgaa    2100 ttactttct ctcattgttt cctgaattat tcgcattggt agaaatatat tagggaaaga    2160
aagtagcctt cttttatag caagagtaaa aaagtctcaa agtcatcaaa taagagcaag    2220
agttgataga gcttttacaa tcaatactca cctaattctg ataaaaggaa tactgcaatg    2280
ttagcaataa gttttttct tctgtaatga ctctacgtta tcctgtttcc ctgtgcctac    2340
caaacactgt caatgtttat tacaaaattt taaagaagaa tatgtaacat gcagtactga    2400
tattataatt ctcattttac tttcattatt tctaataaga gattatgtga cttcttttc    2460 ttttagttct attctacatt cttaatattg tatattacct gaataattca attttttct    2520 aattgaattt cctattagtt gactaaaaga agtgtcatgt ttactcatat atgtagaaca    2580
tgactgccta tcagtagatt gatctgtatt taatattcgt taattaaatc tgcagtttta    2640
tttttgaagg aagccataac tatttaattt ccaaataatt gcttcataaa gaatcccata    2700
ctctcagttt gcacaaaaga acaaaaaata tatatgtctc tttaaattta aatcttcatt    2760
tagatggtaa ttacatatcc ttatatttac tttaaaaaat cggcttattt gtttatttta    2820
taaaaatttt agcaaagaaa tattaatata gtgctgcata gtttggccaa gcatactcat    2880
catttctttg ttcagctcca catttcctgt gaaactaaca tcttattgag atttgaaact    2940
ggtggtagtt tcccaggaag gcacaggtgg agtt                                2974
```

<210> SEQ ID NO 88
<211> LENGTH: 2000
<212> TYPE: DNA
<213> ORGANISM: Homo sapiens

<400> SEQUENCE: 88

```
agtcgctgag ccctggcgcc tccttaaagc cgcagctccg ccccgaccgc ccgcccgcc      60 agtccgtcct cagaccctcc caaccgccgg gtccccgccg cctcggcgga gtgttgtaga    120
gcctcgagcc tgcgaggagc gcgccgcccg ccagctccct gcgtcccgtc ccgcgtcccc    180
gcgttcccgc gtcctgcgat ccgccgccat ggccagtgag gagctggcgt gcaagctgga    240
gcgccggctg cggcgcgagg aggccgagga gagtggcccc cagctggctc ccctcggcgc    300
```

-continued

| | |
|---|---|
| cccagccccg agcccaagcc ccgagcccga gcctcccgcc cgtgcgccca cggccagcgc | 360 |
| cgacgcggag ctgagcgccc agctgagccg gcggctggac atcaacgagg gcgctgcgcg | 420 |
| gccccggcgc tgcagggtct tcaaccccta cacggagttc ccggagttca gccgccgcct | 480 |
| catcaaggac ctggagagca tgttcaaact gtatgacgct gggcgggatg gcttcatcga | 540 |
| cctgatggag ctgaagctga tgatggagaa gctgggggcc cccagaccc acctgggcct | 600 |
| gaagagcatg atcaaggagg tggatgagga cttcgatggc aagctcagct tccgggagtt | 660 |
| cctgctcatt ttccacaagg ccgcggcagg ggagctgcag gaggacagtg ggctgatggc | 720 |
| gctggcaaag ctttctgaga tcgatgtggc cctggagggt gtcaaaggtg ccaagaactt | 780 |
| ctttgaagcc aaggtccaag ccttgtcatc ggccagtaag tttgaagcag agttgaaagc | 840 |
| tgagcaagat gagcggaagc gggaggagga ggagaggcgg ctccgccagg cagccttcca | 900 |
| gaaactcaag gccaacttca atacatagtc ctgctgacct tgccctctgc ccacagctgt | 960 |
| gcctcacaga tgccccgaga agagatgact aggcatcttc atcactgctg tcggtcccct | 1020 |
| ccctgagcca gcatctccat ccaccacccc gtgccagctc ccgtgccagc cttcattcct | 1080 |
| cccagtgtcc aagcccctcc aggagggtcc tggggtgggc cagatgcctg cccacctctg | 1140 |
| tctcctgcct ctgctcctct gcccttctta tagccagaac ttgtatcttc tcagcaacct | 1200 |
| tcactttgtc cttgtccctt taccattccc catcaaagag tagtctgcta tatcaatttg | 1260 |
| tgtagatatg tctgtctttt tgggtcctca gagaaaatgc ccattttctc ggagaattct | 1320 |
| ctgcactcct ctctgcttca cattcaactt ccctgttctc atctttggta ggattctgcc | 1380 |
| agttgctttt gcatcttctg ttcctgggta atggtgggtc ttaatggagg ctgggtggac | 1440 |
| cactgcccgt ccactcttca acaggaggaa cagcatgcca ccatagtaac acacattaga | 1500 |
| gaaaggacag aggtctgctc cttcctgcca cctttctcct ggccccttag cattccccca | 1560 |
| gtccctccct cttcaccttg ctccgtctat gtcttcccag ctcagccttt tccccactct | 1620 |
| taaatactgt actacttcac tgtaagaacg aaagaatagt taggatacca atgagtaaaa | 1680 |
| gggttcctgt tcactctgac tctgtgcaaa ttgtattaca gtagaccgct gacgttccca | 1740 |
| agtgacagat ccagggcctt tcaaacatcc ccaaagtcat ggccatactc accattagcc | 1800 |
| agtttctaac atctgtttca gggtatccag ctgtagatgt tcttatcccc catacttgtg | 1860 |
| agttcttggg gttgctcaca aatactaggg gttttttgttg tattttttaac aaatatatcc | 1920 |
| taatgtcata tttattctct tttgtaactg ctgtctttac aataaagaaa tcatctgcct | 1980 |
| ttctatctta aaaaaaaaaa | 2000 |

<210> SEQ ID NO 89
<211> LENGTH: 3727
<212> TYPE: DNA
<213> ORGANISM: Homo sapiens

<400> SEQUENCE: 89

| | |
|---|---|
| aagtgagagc agcggcagcc ggcggtgcag cagccggccg acccagagtg taagtgcgtg | 60 |
| tgctggggcg agcgggagcg ggcgaggatg ggcacaggat agaggcagag ccacccacgc | 120 |
| cgccgcggcc ccacgctggg cgacagagcc tccagttccc cttcaatggt ggcgggtcgc | 180 |
| cggagctctg atcgccggga acccttgccg ctgctgtcct gcgaccccaa gcaggtatag | 240 |
| acacgtgtgg ccgtttacgc tgtaggatcc tcattcccac tggctttgaa cattttgggg | 300 |
| acttacaatg ccgccacccg cggacatcgt caaggtggcc atagaatggc cgggcgccta | 360 |
| ccccaaactc atggaaattg atcagaaaaa accactgtct gcaataataa aggaagtctg | 420 |

```
tgatgggtgg tctcttgcca accatgaata ttttgcactc cagcatgccg atagttcaaa    480
cttctatatc acagaaaaga accgcaatga gataaaaaat ggcactatcc ttcgattaac    540
cacatctcca gctcagaacg cccagcagct ccatgaacga atccagtcct cgagtatgga    600
tgccaagctg gaagccctga aggacttggc cagcctctcc cgggatgtca cgtttgccca    660
ggagtttata aacctggacg gtatctctct cctcacgcag atggtggaga gcggcactga    720
gcgataccag aaattgcaga agatcatgaa gccttgcttt ggagacatgc tgtccttcac    780
cctgacggcc ttcgttgagc tgatggacca tggcatagtg tcctgggata cattttcggt    840
ggcgttcatt aagaagatag caagttttgt gaacaagtca gccatagaca tctcgatcct    900
gcagcggtcc ttggccattt tggagtcgat ggtgctcaat agccatgacc tctaccagaa    960
agtggcgcag gagatcacca tcggccagct cattccacac ctgcaagggt cagatcaaga   1020
aatccaaacc tatactattg cagtgattaa tgcgcttttc ctgaaggctc ctgatgagag   1080
gaggcaggag atggcgaata ttttggctca gaagcaactg cgttccatca ttttaacaca   1140
tgtcatccga gcccagcggg ccatcaacaa tgagatggcg caccagctgt atgttctaca   1200
agtgctcacc tttaacctcc tggaagacag gatgatgacc aaaatggacc cccaggacca   1260
ggctcagagg gacatcatat ttgaacttcg aagaattgct tttgatgctg agtctgaacc   1320
taacaacagc agtggcagca tggagaaacg caagtccatg tacacgcgag attataagaa   1380
gcttgggttc attaatcatg tcaaccctgc catggacttc acgcagactc cacctgggat   1440
gttggctctg gacaacatgc tgtactttgc caagcaccac caagatgcct acatccggat   1500
tgtgcttgag aacagtagtc gagaagacaa gcatgaatgt ccctttggcc gcagtagtat   1560
agagctgacc aagatgctat gtgagatctt gaaagtgggc gagttgccta gtgagacctg   1620
caacgacttc cacccgatgt tcttcaccca cgacagatcc tttgaggagt ttttctgcat   1680
ctgtatccag ctcctgaaca agacatgaa ggaaatgagg gcaacttctg aagacttcaa   1740
caaggtaatg caggtggtga aggagcaggt tatgagagca cttacaacca agcctagctc   1800
cctggaccag ttcaagagca aactgcagaa cctgagctac actgagatcc tgaaaatccg   1860
ccagtccgag aggatgaacc aggaagattt ccagtcccgc ccgattttgg aactaaagga   1920
gaagattcag ccagaaatct tagagctgat caaacagcaa cgcctgaacc gccttgtgga   1980
agggacctgc tttaggaaac tcaatgcccg gcggaggcaa gacaagtttt ggtattgtcg   2040
gctttcgcca aatcacaaag tcctgcatta cggagactta aagagagtc ctcagggaga   2100
agtgccccac gattccttgc aggacaaact gccggtggca gatatcaaag ccgtggtgac   2160
gggaaaggac tgccctcata tgaaagagaa aggtgccctt aaacaaaaca aggaggtgct   2220
tgaactcgct ttctccatct tgtatgactc aaactgccaa ctgaacttca tcgctcctga   2280
caagcatgag tactgtatct ggacggatgg actgaatgcg ctactcggga aggacatgat   2340
gagcgacctg acgcggaatg acctggacac cctgctcagc atggaaatca gctccgcct    2400
cctggacctg gaaaacatcc agatccctga cgcacctccg ccgattccca aggagcccag   2460
caactatgac ttcgtctatg actgtaactg aagtggccgg gccagacat gccccttcca   2520
aaactggaac acctagctaa caggagagag gaatgaaaac acaccacgc cttgaaccg    2580
tcctttggta aagggaagct gtgggtccac attcccttca gcatcacctc tagccctggc   2640
aactttcagc cctagctgg catcttgctc accgccctga ttctgttcct cggctccact   2700
gcttcaggtc acttcccatg gctgcagtcc actggtggga caagagcaaa gcccactgcc   2760
```

| | |
|---|---|
| agtaagaagg ccaaagggcc cttccatcct agccctctgc aggcatgccc ttccttccct | 2820 |
| tgggcaggaa agccagcagc cccagactgc ccaaaaactt gcccaccaga ccaagggcag | 2880 |
| tgccccaagg cccctgtctg gaggaaatgg cctagctatt tgatgagaag accaaacccc | 2940 |
| acatcctcct ttccctctc tctagaatca tctcgcacca ccagttacac ttgaattaag | 3000 |
| atctgcgctc aaatctcctc ccacctctct ccctgctttt gccttgctct gttcctcttt | 3060 |
| ggtcccaaga gcagcagccg cagcctcctc gtgatcctcc ctagcataaa tttcccaaac | 3120 |
| agtccacagg tccatgccc actttgcgtc tgcactgtga tcgtgacaaa tcttccctcc | 3180 |
| tcaccagcta gtctggggtt tcctctccct gccccaggcc agaactgcct tcttcatttc | 3240 |
| cacccacgct cccagcctct tagctgaaag cacaaatggt gaaatcagta gtctcgctcc | 3300 |
| atctctaata gactaaacct aaatgcctct aggacggact gttgctatcc aagcgtttgg | 3360 |
| tgttaccttc tcctgggagg tcctgctgca actcaagttc cacaggatgg tcaagctgtc | 3420 |
| agacatccaa gtttacatca ttgtaattat tactggtatt tacaatttgc aagagttttg | 3480 |
| ggttagtttt tttttttttt tttgctttgt ttttgtacaa aagagtctaa cattttttgc | 3540 |
| caaacagata tatatttaat gaaaagaaga gatacataaa tgtgtgaatt tccagttttt | 3600 |
| ttttaattat tttaatccca aacatcttcc tgaaaataac attcccttaa acatgctgtg | 3660 |
| gaataaaatg gattgtgatg atttggaaaa aaaaaaaaa aaaaaaaaaa aaaaaaaaa | 3720 |
| aaaaaaa | 3727 |

<210> SEQ ID NO 90
<211> LENGTH: 4654
<212> TYPE: DNA
<213> ORGANISM: Homo sapiens

<400> SEQUENCE: 90

| | |
|---|---|
| gcagcgtagc gggctggcgg tgacttacac cgggactcca gagggagaga ggaagcgctg | 60 |
| caggccactt gcattgcgtc ttccaggctg cgtggacccg cgcccccggc gtgtgcggtt | 120 |
| gtggggagc tcgccgtggc ctcccctccc tctggcttta gcttcctttg gggttggcgc | 180 |
| aggtgggcca gcagcgcac cgcagatctc cccgttccca cgaaggctgg ctcgctgtct | 240 |
| ctctccgagc gggagggacc atcctaaaaa tatgtaaata tccaagcgct ggctccaggc | 300 |
| tggggcagct gccaaggtcc ccgcgccgcc gccgggtgtt ttacatgaaa atgagaagcc | 360 |
| tgatgggaac cgcgttctaa cttaaggcag cctggtgatt agcatgagac tgggcggctg | 420 |
| tcctgcttcc tgcccttcaa tagccgttcc gcgcgctcgc gccggagcag cgctgccgcc | 480 |
| gcgcggggt cgatcgcagg ctcggcgtcc ttggcagcca tggctccggc gccgcctcgg | 540 |
| ccagtaagta ggagcatgca tgtgtagggg gcacatgcgt gtcggcgcac ccacccagcc | 600 |
| atccacccgc gcgcacgcac agcgcccgga gcctcggcaa ggggaagatt gacgaggcgc | 660 |
| tgcagtcgcg gggacgacgc gggctcttcc tggattccgc aggagcccgc ccgccgcagc | 720 |
| tgctgtctgc agagcctgct cggatcctgt gcacacgcgc ccccgctcg agcctctgtg | 780 |
| atgaagactg tctcccgggg actgcagcgg aggcagagcc agccagcgcc ggggactgcg | 840 |
| ggccgtgcgc ctgataggcc cgcggggaca cgactcggac actgtcatcc ccacgcctcg | 900 |
| cgctgagctg cccggcgcgg agggtctgcc gccgcccctc cggcctcccg cacgcccgat | 960 |
| cccgggtcag ccccggaggc ctcggctgcc tcatttgttt gggtcttttg tgccgtggct | 1020 |
| cccagttggc caagcactcc tgcgctgaat cgggccattg tctgcgctcc cattgccttc | 1080 |
| acgctgcaag tctcggcgcc cccaccccgc ccgcccccctc ccgcctcct cccggccggg | 1140 |

```
gagcctccta acgtgccttt ccccccagga atctggaagc tataagccgg gcggattgca    1200
aatgaagtgt aatgcattgt gggacgtgtg taaaatcgga gccttcgccg tgggggtgtg    1260 gggggggcgtg gggagggccg gacccgccgc tggcggtgta gacgccgacg aggaggggct   1320
gggaaaatgt gcgcagagtc cgcccgggtc gtgcccgccg tagacggatg aaggagcgcg    1380
ctgcgccccg gcgctgaggc cccgaggatc ggggcggcag gtcgccctcc ccaccatgaa    1440
gaagacccgg agcacaacct gcggcgagc ctggcctagc tcggatttct cggaccgggc    1500
ctcggaccgc atgaggtccc gcagcgagaa ggactaccgc tgcacaagc gtttccccgc    1560 ggccttcgcg ccccaggctt cgcggggcta catgacatca ggtgatgtat cacccatcag   1620
tatgtctccc atcagtcagt ctcagtttat tccactcggg gagatcctct gcttggccat    1680
ctcagcaatg aactcggcaa gaaagcctgt cacccaagaa gcactgatgg agcacctgac    1740
cacgtgcttc ccaggtgttc aacgccaag ccaagaaatt ctgcggcaca cgctgaacac     1800
gctggtacgg gagaggaaga tctacccaac tccagatggc tacttcatcg tgaccccaca    1860
gacttatttc ataactcctt ccctcataag aactaacagt aaatggtacc atttggacga    1920
gaggatacct gaccggtctc agtgcacctc tccgcaaccc gggaccatca cgccctctgc    1980
ctcaggctgt gtcagggaaa ggacattgcc ccgaaaccac tgcgactctt gccactgctg    2040
cagagaagac gtgcacagca cgcatgcacc caccctgcaa aggaagtctg ccaaggactg    2100
caaagaccct tactgtcccc cttctctgtg ccaggtgcca cccactgaaa agagcaaaag    2160
tactgtaaat ttttcctata agacagaaac tctctcaaaa cctaaagata gtgaaaagca    2220
gtcaaaaaaa ttcgggctaa agttattccg gttaagtttt aaaaaagaca agaccaaaca    2280
gctggccaat ttttctgccc agtttcctcc tgaagagtgg cccctgcgag acgaggacac    2340
gccagctacg atccctcggg aagtagagat ggaaatcatt aggcgcatta cccagacct    2400 gaccgtggaa aatgtcatgc ggcacaccgc gctcatgaag aaactggaag aagaaaaggc    2460
ccagaggagt aaagccgggt cctctgccca tcacagcgga aggagtaaaa agagtaggac    2520
tcatcggaag tcccatggaa agtctcggtc tcacagcaag acacgggtgt ctaaaggaga    2580
cccttccgac ggttcacatc tggatatccc agctgaaaga gagtatgact tttgtgatcc    2640
tcttaccagg gtgcccaggg agggctgctt catcattgaa cacaaaggag ataacttcat    2700
catgcacagc aacacaaacg tgctcgagtc ccacttcccc atgacaccag aatgggatgt    2760
gtctggtgaa ttggctaaaa ggagaactga gatgccttt cctgaacctt ctaggggaag    2820
ctcccactca aaagtgcacc gaagccacag ccatacacag gaccggaggt ccaggaatga    2880
gagatccaac aaagccaagg agagatccag gtcgatggat aactccaaag ccctctggg    2940 tgcttcttct ctagggacgc cggaagacct tgctgaaggc tgcagccaag acgaccagac    3000
ccccagccaa tcctacattg acgacagtac tttaaggcct gcacagaccg ttagtctcca    3060
aagggctcac atttcgtcca caagctataa agaggtgtgt attccagaga tagtcagtgg    3120
cagcaaggaa ccgtccagcg cttgcagcct tttggagcca ggaaaaccac ccgagagttt    3180
gccatcctat ggcgaactca actcttgtcc aacaaaaaca gccacagatg actatttcca    3240
gtgcaacacc tctagtgaga cggtgctcac ggcaccatca cctctgggaa agaataagga    3300
ggaccatgac actctgactt tggcagaagg ggtgaaaaag ctctccctt ctgataggca    3360 ggtcccccac tcctccaggg agcctgtggg gcacaaggag gagtcaccaa aagggccggg    3420
tgggggcccc gctgcttcgg gaggagtggc tgaagggatc gccaacggac gcctcgtcca    3480
```

```
gcaccatggt gccgagccca gcagcttgga caagaggaaa gagatattta gcaaagacac    3540
actgttcaaa cctcttcaca gcaccttgtc tgtaaacagc tatcacaagt cgagcctgtc    3600
cctcctcaaa tctcacccga agacacctgc tgacacattg ccaggccgat gtgagaaact    3660
ggaaccgtcc ctggggacct cggcggcaca agccatgcct gcttcccagc gtcagcagga    3720
gtcaggaggg aaccaggaag cctcttttga ctattacaac gtctctgatg atgacgactc    3780
tgaggaaggg gcaaacaaga acacagagga ggagaaaaat agagaggacg taggcaccat    3840
gcagtggctc ctcgagcggg agaaggaaag agacttgcag aggaaatttg aaaagaacct    3900 caccttctt gctccaaaag aaaccgacag cagcagcaac cagagagcca cccattcagc    3960
ccggctcgac agcatggaca gcagcagcat cacagtggac agtggattca actccccacg    4020
tactcgggag agcctggctt ccaacacatc aagcattgtt gaaagtaacc gtcgtcagaa    4080
ccccgctttg agcccggccc atggtggagc tggtccagcc ttcaacttcc gagcgagcgc    4140
ggagcccccg acaaatgaag ctgagaagct acagaaacct tccaactgct tgcaagcttc    4200
tgttactagc gtgtgattgt ccttctgcct cagatcttct gtctcattcg atacagcaaa    4260
gtttacgaca ctgggactga tgtttacatc tttggaaaga caagcatctc aaccacagtt    4320
tttgtgttta cttaaactgt gctgctaagt agggctaggg caaaaaaaca aaaatcttt    4380 atttcagagt attgcttttc acatttatgg ctctgtagca actgagtaac agtagggtg    4440 atatgtatac ttttgcttca ctaattgtat ctgagcacac ataggaaagt ctagacactg    4500
taagtgtaat acgcattttc aatgtcatgc agttgccaat tccattttaa aatgccacag    4560
atgcgtgttg ctcccagtct gtggttaaac ggtgccacag aactgatcct tgacacttcc    4620
aaaaaaaaaa aaacaaaaca aaacaaaaaa aatt                                4654

<210> SEQ ID NO 91
<211> LENGTH: 2605
<212> TYPE: DNA
<213> ORGANISM: Homo sapiens

<400> SEQUENCE: 91
gaatatcgca tccgggaact ctgcgcgccc atgcggagag tcggagggcg agctgacgag      60
gacgctacgg cggcgggaag tctgtgggtt ctggcaccac ctgagcccac tgggcatctg     120
gtcatccctg gcacctctcc tttggagcca ccttgtccct ggctagacag tcacatttc     180 cagtgccgtt ttggaaagat gttgcctttg gagaaggcgt ttgcctcccc caggagctcc     240
ccagccccgc cggatctgcc cacgccgggg tcagcagccg gagtccagca ggaagaaccc     300
gagaccatcc ctgagaggac ccctgctgac ctggagttct cccgcctgcg tttccgggaa     360
tttgtctacc aggaggctgc cgggcccac cagaccctgg cccggctgca tgagctgtgc     420
cgccagtggc tgatgcctga ggcgcgctcc aaggagcaga tgctggagct gctggtgctg     480
gagcagttcc tgggcatcct gcctgataag gtccggccct gggtggtggc acagtaccct     540
gagagctgca agaaggcagc ctccctggtg gagggcctcg ctgatgtcct ggaagagcca     600
gggatgctgc tgggctcccc tgcgggctca tcctcaattc ttagcgatgg agtgtacgag     660
aggcacatgg accctctgct gctaccaggc gagctcgcga gcccagcca ggcccttgga     720 gctggggaga tcccggcacc ttctgagaca ccctggcttt ctccggaccc cctgtttctg     780
gaacagagga gggtcagaga agcaaagacc gaagaggacg gccctgccaa caccgagcag     840
aagctgaagt cctttccaga ggaccctcag cacctggggg agtggggcca cctgaccct     900 gccgaggaga acctgaagag ctaccggaag ctgctcctgt gggggtatca gctttcccag     960
```

| | | | |
|---|---|---|---|
| cctgacgctg | cctccaggct | ggacactgag gaactccggt | tggtggaaag agatccacaa | 1020 |
| ggaagcagcc | tcccagaagg | cgggaggcgg caggagagcg | ctgggtgcgc ctgcgaggag | 1080 |
| gccgccccg | cggggtgct | gcctgagctg cctacggagg | cgcccctgg ggacgccctt | 1140 |
| gccgatcccc | cgtcgggcac | cactgaggag gaggaagagc | agcctgggaa ggccccggac | 1200 |
| ccgcaggacc | cccaggacgc | ggagtccgac tctgccaccg | gatcgcagag gcagtccgtc | 1260 |
| atccagcagc | ctgccccgga | caggggcacg gcgaaactgg | gaaccaagag gccgcacccc | 1320 |
| gaggatgggg | acgggcagag | cctcgagggc gtctctagct | ccggcgacag cgcagggctg | 1380 |
| gaggccgggc | agggccctgg | ggctgacgag ccgggcttgt | cccgcgggaa gccctatgcc | 1440 |
| tgcggcgagt | gcggggaggc | cttcgcgtgg ctctcgcacc | tgatggagca ccacagcagc | 1500 |
| catggcggcc | ggaagcgcta | cgcctgtcag ggctgctgga | agaccttcca cttcagcctg | 1560 |
| gccctagccg | agcaccagaa | gacccacgag aaggagaaaa | gctacgcgct ggggggcgcc | 1620 |
| cggggccccc | aaccgtccac | ccgcgaagcc caggcggggg | ctaggcgggg cggtccccca | 1680 |
| gagagcgtgg | agggcgaggc | tcccccccgca cccccagagg | cgcagaggtg agccgctgtg | 1740 |
| ctgtcccgtt | ccggaggggc | cgcttttgccg gccgtgaatc | ccagacgagg cattgggcct | 1800 |
| ttccacgccc | ctgggtggcg | gcttcctgtg gtgtttgtgg | acgtcctctg cctgtgccct | 1860 |
| gaatccgctc | ctgaggctaa | gcgctcccaa cgagaagggt | ccacgggaag ccctcacctc | 1920 |
| tgtaaacaca | ccctgggcca | cgcgctcgcat ccgaggggag | ccgccggatg tggaagaaga | 1980 |
| ctcggctttc | ctgcagccat | ttagtgccgc cccatgctag | gttatttgac attgtgcagt | 2040 |
| gtagagttgc | cttaaagtgc | gtgatctgcc agtgctttct | tcaagtcacc cttgccccga | 2100 |
| ttcctcctgt | ttgcgctccc | cagggttgct caagtggaaa | ttttgtcagc tgtttagcct | 2160 |
| tttcgtactt | ggcgtgatgt | caacttcact tctaatctgc | aaaagcagaa gctgtttcct | 2220 |
| agtttacctc | gcgtgtgttt | acctatatgg agtagctcgc | agagatcaca gaaatgcttg | 2280 |
| cagcctaagg | cagggttttc | agaccgtggg tcccagccca | tttagtaaaa tgggaaatca | 2340 |
| attagcaagt | ggtcaccagc | attacacagc aatgaagcag | aataaagtag gccagaatgc | 2400 |
| atcatgtagt | aaaggcaaat | actgttttgt gaaacttttc | acccatacat ctaaatgtga | 2460 |
| gaactggttg | caatgtaaga | catttcttgc tgggaagttg | tgagcaaaat aagttgaaaa | 2520 |
| cactaataaa | gatctgtctg | tctgagcaaa ggagactaaa | ctccttgggc tacaaaaaaa | 2580 |
| aaaaaaaaaa | aaaaaaaaaa | aaaaa | | 2605 |

<210> SEQ ID NO 92
<211> LENGTH: 2389
<212> TYPE: DNA
<213> ORGANISM: Homo sapiens

<400> SEQUENCE: 92

| | | | |
|---|---|---|---|
| aggcgcggtt | gtgagtagta | ccgggagtgg ggtgatcccg | ggctagggga gcgcggcggc | 60 |
| cgcgatcggg | cttagtcgga | gctccgaagg gagtgactag | gacacccggg tgggctactt | 120 |
| ttcttccggt | gcttttgctt | ttttttttcct ttgggctcgg | gctgagtgtc gcccactgag | 180 |
| caaagattcc | ctcgtaaaac | ccagagcgac cctcccgtca | attgttgggc tcgggagtgt | 240 |
| cgcggtgccc | cgagcgcgcc | gggcgcggag gcaaagggag | cggagccggc gcggacggg | 300 |
| gcccggagct | tgcctgcctc | cctcgctcgc ccagcgggt | tcgctcgcgt agagcgcagg | 360 |
| gcgcgcgcga | tgaaggcggt | gagcccggtg cgcccctcgg | gccgcaaggc gccgtcgggc | 420 |

```
tgcggcggcg gggagctggc gctgcgctgc ctggccgagc acggccacag cctgggtggc    480
tccgcagccg cggcggcggc ggcggcggca gcgcgctgta aggcggccga ggcggcggcc    540
gacgagccgg cgctgtgcct gcagtgcgat atgaacgact gctatagccg cctgcggagg    600
ctggtgccca ccatcccgcc caacaagaaa gtcagcaaag tggagatcct gcagcacgtt    660
atcgactaca tcctggacct gcagctggcg ctggagacgc acccggccct gctgaggcag    720
ccaccaccgc ccgcgccgcc acaccacccg gccgggacct gtccagccgc gccgccgcgg    780
accccgctca ctgcgctcaa caccgacccg gccggcgcgg tgaacaagca gggcgacagc    840
attctgtgcc gctgagccgc gctgtccagg tgtgcggccg cctgagcccg agccaggagc    900
actagagagg gaggggaag agcagaagtt agagaaaaaa agccaccgga ggaaaggaaa    960
aaacatcggc caacctagaa acgttttcat tcgtcattcc aagagagaga gaggaaagaa    1020
aaatacaact ttcattcttt ctttgcacgt tcataaacat tctacatacg tattctcttt    1080
tgtctcttca tttataactg ctgtgaattg tacatttctg tgttttttgg aggtgcagtt    1140 aaactttttaa gcttaagtgt gacaggactg ataaatagaa gatcaagagt agatccgact    1200
ttagaagcct actttgtgac caaggagctc aattttgtt ttgaagcttt actaatctac    1260
cagagcattg tagatatttt ttttttacat ctattgttta aaatagatga ttataacggg    1320
gcagagaact tcttttctc tgcaagaatg ttacatattg tatagataaa tgagtgacat    1380
ttcataccat gtatatatag agatgttcta taagtgtgag aaagtatatg ctttaataga    1440
tactgtaatt ataagatatt tttaattaaa tattttttg taaatattat gtgtgtgttt    1500 tttttaatc tatgggaata tttcttttgg aaaatcattt ttcagctcaa ttacagagct    1560
cttgatatct tgaatgtctt ttctgtttgg cctggctctt aatttgcttt tgttttgccc    1620
agtatagact cggaagtaac agttatagct agtggtcttg catgattgca tgagatgttt    1680
aatcacaaat taaacttgtt ctgagtccat tcaaatgtgt ttttttaaat gtagattgaa    1740
atctttgtat ttgaagcata catgttgaaa atacacctta tcagttttta agtacagggt    1800
tttatagtgt aatatataca gagtaagtgt ttgttttgt ttttcaactg aggtcaaaat    1860
ggattctgaa tgatttttgca tatgggatga ggaaatgctt ggatccttaa ggagtttacg    1920
aaatctgctg ttttatcaaa gtgaaaaaaa attgcttatt actcttcatt ttacactaaa    1980
gcttaatgtc actaagtttc atgtctgtac agattattta aatcatggaa atgaaaaaaa    2040
tgttctctgc ttgctaccaa aggacaaact cttggaaatg aacactttct gctttccttc    2100
ctccaaagaa ttaataggca acagtgggag aaaaaaaagg cataatggca aatccttcaa    2160
gcagggataa aagtcgatct tcaaacatta acttaagcag accaaaaatt ctgatgaccg    2220
catctagatt attttttttat aaaaatgatt tcactatag ctatgttacg ctaagctact    2280
gtcccatctc ttgtgatgtg taacttttac atgtgaatat taaagtagat ttctctgtct    2340
tgtaaaaaaa aaaaaaaaa aaaaaaaaaa aaaaaaaaa aaaaaaaa    2389
```

<210> SEQ ID NO 93
<211> LENGTH: 3925
<212> TYPE: DNA
<213> ORGANISM: Homo sapiens

<400> SEQUENCE: 93

```
attacgtgaa caaatagctg aggggcggcc gggccagaac ggcttgtgta actttgcaaa     60
cgtgccagaa agtttaaaat ctctcctcct tccttcactc cagacactgc ccgctctccg    120
ggactgccgc gccgctcccc gttgccttcc aggactgaga aaggggaaag ggaagggtgc    180
```

```
cacgtccgag cagccgcctt gactggggaa gggtctgaat cccacccttg gcattgcttg    240
gtggagactg agatacccgt gctccgctcg cctccttggt tgaagatttc tccttccctc    300
acgtgatttg agccccgttt ttatttcctg tgagccacgt cctcctcgag cggggtcaat    360
ctggcaaaag gagtgatgcg cttcgcctgg accgtgctcc tgctcgggcc tttgcagctc    420
tgcgcgctag tgcactgcgc ccctcccgcc gccggccaac agcagccccc gcgcgagccg    480
ccggcggctc cgggcgcctg gcgccagcag atccaatggg agaacaacgg gcaggtgttc    540
agcttgctga gcctgggctc acagtaccag cctcagcgcc gccgggaccc gggcgccgcc    600
gtccctggtg cagccaacgc ctccgcccag cagccccgca ctccgatcct gctgatccgc    660
gacaaccgca ccgccgcggc gcgaacgcgg acggccggct catctggagt caccgctggc    720
cgccccaggc ccaccgcccg tcactggttc aagctggct actcgacatc tagagcccgc    780
gaagctggcg cctcgcgcgc ggagaaccag acagcgccgg agaagttcc tgcgctcagt    840 aacctgcggc cgcccagccg cgtggacggc atggtgggcg acgacccttta caaccccatc    900 aagtactctg acgacaaccc ttattacaac tactacgata cttatgaaag gcccagacct    960
gggggcaggt accggcccgg atacggcact ggctacttcc agtacggtct cccagacctg   1020
gtggccgacc cctactacat ccaggcgtcc acgtacgtgc agaagatgtc catgtacaac   1080
ctgagatgcg cggcggagga aaactgtctg gccagtacag catacagggc agatgtcaga   1140
gattatgatc acagggtgct gctcagattt ccccaaagag tgaaaaacca agggacatca   1200
gatttcttac ccagccgacc aagatattcc tgggaatggc acagttgtca tcaacattac   1260
cacagtatgg atgagtttag ccactatgac ctgcttgatg ccaacaccca gaggagagtg   1320
gctgaaggcc acaaagcaag tttctgtctt gaagacacat cctgtgacta tggctaccac   1380
aggcgatttg catgtactgc acacacacag ggattgagtc ctggctgtta tgatacctat   1440
ggtgcagaca tagactgcca gtggattgat attacagatg taaaacctgg aaactatatc   1500
ctaaaggtca gtgtaaaccc cagctacctg gttcctgaat ctgactatac caacaatgtt   1560
gtgcgctgtg acattcgcta cacaggacat catgcgtatg cctcaggctg cacaatttca   1620
ccgtattaga aggcaaagca aaactcccaa tggataaatc agtgcctggt gttctgaagt   1680
gggaaaaaat agactaactt cagtaggatt tatgtatttt gaaaagaga acagaaaaca   1740 acaaagaatt tttgtttggg actgttttca ataacaaagc acataactgg attttgaacg   1800
cttaagtcat cattacttgg gaaattttta atgtttatta tttacatcac tttgtgaatt   1860
aacacagtgt ttcaattctg taattacata tttgactctt tcaaagaaat ccaaatttct   1920
catgttcctt ttgaaattgt agtgcaaaat ggtcagtatt atctaaatga atgagccaaa   1980
atgactttga actgaaactt ttctaaagtg ctggaacttt agtgaaacat aataataatg   2040
ggtttatata tgtcatagca tagatgaatt tagaaacaat gctcctactg tttaaataca   2100
tatggacaca tctggtgctg agaaagaaac aaacacatta ccattggtgt caagaaatat   2160
tactatatag cagagaaatg gcaatacatg tactcagata gttacatccc tatataaaaa   2220
gtatgtttac atttaaaaaa ttagtagata acttcctttc tttcaagtgc acaatttcat   2280
tttgacttga gtcaactttt gttttggaac aaattaagta agggagctgc ccaatcctgt   2340
ctgatatttc ttgaggctgc cctctatcat tttatctttc ccatgggcag agatgttgta   2400
agtgggattc ttaatatcac cattcttggg actggtatac ataaggcagc cgtgaaactg   2460
gaaagtcatt ttgatgactg atgtgataca tccagaggta aaatgcattt aaacatatta   2520
```

```
aagtatttgc caaagataca attttcttgc tgacataaaa atcacacaaa caagtccccc    2580
ccaaaccaca actgtctctc aaatagctta aaaaaattga aaaacatttt aggattttc     2640 aagttttcta gattttaaaa agatgttcag ctattagagg aatgttaaaa attttatatt    2700
atctagaaca caggaacatc atcctgggtt attcaggaat cagtcacaca tgtgtgtgtg    2760
tctgagatat agtctaaatt agcaaagcac atagtattac atacttgagg ggttggtgaa    2820 caaggaaaa atatactttc tgcaaaacca aggactgtgc tgcgtaatga dacagctgtg     2880
atttcatttg aaactgtgaa accatgtgcc ataatagaat tttgagaatt ttgcttttac    2940
ctaaattcaa gaaaatgaaa ttacactttt aagttagtgg tgcttaagca aattttttcc    3000
tatattaacc agtattaaaa tctcaagtaa gattttccag tgccagaaca tgttaggtgg    3060
aattttaaaa gtgcctcggc atcctgtatt acatgtcata gaattgtaaa gtcaacatca    3120
attactagta atcattctgc actcactggg tgcatagcat ggttagaggg gctagagatg    3180
gacagtcatc aactggcgga tatagcggta catatgatcc ttagccacca gggcacaagc    3240
ttaccagtag acaatacaga cagagctttt gttgagctgt aactgagcta tggaatagct    3300
tctttgatgt acctctttgc cttaaattgc tttttagttc taagattgta gaatgatcct    3360
ttcaaattgt aatcttttct aacagagata ttttaatata cttgctttct taaaaaacaa    3420
aaaaactact gtcagtatta atactgagcc agactggcat ctacagattt cagatctatc    3480
attttattga ttcttaagct tgtattaaaa actaggcaat atcatcatgg atacatagga    3540
gaagacacat ttacaatcat tcattgggcc ttttatctgt ctatccatcc atcatcattt    3600
gaaggcctaa tatatgccaa gtactcacat ggtatgcatt gagacataaa aaagactgtc    3660
tataacctca ataagtatta aaaatcccat tattacccat aaggttcatc ttatttcatt    3720
tttagggaat aaaattacat gtctatgaaa tttcaattt aagcactatt gtttttcatg    3780
accataattt atttttaaaa ataaattaaa ggttaattat atgcatgtat gtatttctaa    3840
taattaaaaa tgtgttcaat ccctgaaatg tctgcctttt aaatataaca cctactattt    3900
ggttaaaaaa aaaaaaaaaa aaaaa                                          3925
```

<210> SEQ ID NO 94
<211> LENGTH: 2344
<212> TYPE: DNA
<213> ORGANISM: Homo sapiens

<400> SEQUENCE: 94

```
aaaatcgatt gctctctgcc acaaaccgga gacccttctt gggcgatccg ctttctcagc     60
atgtggaagg ttttctctc tctcttcttt ttctactaaa ccttccgctc ctaaacccat     120
tcctcgtgtg tatccctgtc ctgaattctt tctcgaccat gacaaagaac cagcttccac    180
tgcagagagg tccattccaa ctgctcagat gaagctgaaa agagcccgac tcgccgatga    240
tctcaatgaa aaaattgctc tacgaccagg gccactggag ctggtggaaa aaaacattct    300
tcctgtggat tctgctgtga agaggccat aaaaggtaac caggtgagtt ctccaaatc     360 cacggatgct tttgcctttg aagaggacag cagcagcgat gggctttctc cggatcagac    420
tcgaagtgaa gacccccaaa actcagcggg atccccgcca gacgctaaag cctcagatac    480
cccttcgaca ggttctctgg ggacaaacca ggatcttgct tctggctcag aaaatgacag    540
aaatgactca gcctcacagc ccagccacca gtcagatgcg gggaagcagg gcttggccc     600 ccccagcacc cccatagccg tgcatgctgc tgtaaagtcc aaatccttgg gtgacagtaa    660
gaaccgccac aaaaagccca aggaccccaa gccaaaggtg aagaagctta aatatcacca    720
```

```
gtacattccc ccagaccaga aggcagagaa gtcccctcca cctatggact cagcctacgc    780
tcggctgctc cagcaacagc agctgttcct gcagctccaa atcctcagcc agcagcagca    840
gcagcagcaa caccgattca gctacctagg gatgcaccaa gctcagctta aggaaccaaa    900
tgaacagatg gtcagaaatc caaactcttc ttcaacgcca ctgagcaata ccccttgtc     960
tcctgtcaaa aacagttttt ctggacaaac tggtgtctct tctttcaaac caggcccact   1020
cccacctaac ctggatgatc tgaaggtctc tgaattaaga caacagcttc gaattcgggg   1080
cttgcctgtg tcaggcacca aaacggctct catggaccgg cttcgaccct ccaggactg    1140
ctctggcaac ccagtgccga actttgggga tataacgact gtcactttc ctgtcacacc    1200
caacacgctg cccaattacc agtcttcctc ttctaccagt gccctgtcca acggcttcta   1260
ccactttggc agcaccagct ccagcccccc gatctcccca gcctcctctg acctgtcagt   1320
cgctgggtcc ctgccggaca ccttcaatga tgcctccccc tccttcggcc tgcacccgtc   1380
cccagtccac gtgtgcacgg aggaaagtct catgagcagc ctgaatgggg gctctgttcc   1440
ttctgagctg gatgggctgg actccgagaa ggacaagatg ctggtggaga agcagaaggt   1500
gatcaatgaa ctcacctgga aactccagca agagcagagg caggtggagg agctgaggat   1560
gcagcttcag aagcagaaaa ggaataactg ttcagagaag aagccgctgc ctttcctggc   1620
tgcctccatc aagcaggaag aggctgtctc cagctgtcct tttgcatccc aagtacctgt   1680
gaaaagacaa agcagcagct cagagtgtca cccaccggct tgtgaagctg ctcaactcca   1740
gcctcttgga aatgctcatt gtgtggagtc ctcagatcaa accaatgtac tttcttccac   1800
atttctcagc ccccagtgtt cccctcagca ttcaccgctg ggggctgtga aaagcccaca   1860
gcacatcagt ttgcccccat cacccaacaa ccctcacttt ctgccctcat cctccggggc   1920
ccagggagaa gggcacaggg tctcctcgcc catcagcagc caggtgtgca ctgcacagaa   1980
ctcaggagca cacgatggcc atcctccaag cttctctccc cattcttcca gcctccaccc   2040
gcccttctct ggagcccaag cagacagcag tcatggtgcc gggggaaacc cttgtcccaa   2100
aagcccatgt gtacagcaaa agatggctgg tttacactct tctgataagg tggggccaaa   2160
gttttcaatt ccatcccaa ctttttctaa gtcaagttca gcaatttcag aggtaacaca    2220
gcctccatcc tatgaagatg ccgtaaagca ggtaaccatg tgatttgttc tttatggaag   2280
aatagactga ctcaatgaac agacattgtt tgatatgatt aaacttcacg cagtttgtaa   2340
attc                                                                2344
```

<210> SEQ ID NO 95
<211> LENGTH: 21
<212> TYPE: DNA
<213> ORGANISM: Artificial Sequence
<220> FEATURE:
<223> OTHER INFORMATION: primer

<400> SEQUENCE: 95
ggttcgttta ttttgggttt c                                             21

<210> SEQ ID NO 96
<211> LENGTH: 20
<212> TYPE: DNA
<213> ORGANISM: Artificial Sequence
<220> FEATURE:
<223> OTHER INFORMATION: primer

<400> SEQUENCE: 96

```
tccgatcacc cctacatacg                                                         20

<210> SEQ ID NO 97
<211> LENGTH: 26
<212> TYPE: DNA
<213> ORGANISM: Artificial Sequence
<220> FEATURE:
<223> OTHER INFORMATION: primer

<400> SEQUENCE: 97
gagggaggta gtttattttt attgtt                                                  26

<210> SEQ ID NO 98
<211> LENGTH: 21
<212> TYPE: DNA
<213> ORGANISM: Artificial Sequence
<220> FEATURE:
<223> OTHER INFORMATION: primer

<400> SEQUENCE: 98
aaaaaccaaa ctcctcaacc a                                                       21

<210> SEQ ID NO 99
<211> LENGTH: 23
<212> TYPE: DNA
<213> ORGANISM: Artificial Sequence
<220> FEATURE:
<223> OTHER INFORMATION: primer

<400> SEQUENCE: 99
aaggggtcgt ttttattttc gtc                                                     23

<210> SEQ ID NO 100
<211> LENGTH: 21
<212> TYPE: DNA
<213> ORGANISM: Artificial Sequence
<220> FEATURE:
<223> OTHER INFORMATION: primer

<400> SEQUENCE: 100
tcttcccgaa acaccaacac g                                                       21

<210> SEQ ID NO 101
<211> LENGTH: 26
<212> TYPE: DNA
<213> ORGANISM: Artificial Sequence
<220> FEATURE:
<223> OTHER INFORMATION: primer

<400> SEQUENCE: 101
aagagggtgt gatatagatg ttaagt                                                  26

<210> SEQ ID NO 102
<211> LENGTH: 20
<212> TYPE: DNA
<213> ORGANISM: Artificial Sequence
<220> FEATURE:
<223> OTHER INFORMATION: primer

<400> SEQUENCE: 102
cttcccaaaa caccaacaca                                                         20

<210> SEQ ID NO 103
<211> LENGTH: 20
<212> TYPE: DNA
<213> ORGANISM: Artificial Sequence
```

```
<220> FEATURE:
<223> OTHER INFORMATION: primer

<400> SEQUENCE: 103
tcgtgtttgg tttgtaaggc                                          20

<210> SEQ ID NO 104
<211> LENGTH: 21
<212> TYPE: DNA
<213> ORGANISM: Artificial Sequence
<220> FEATURE:
<223> OTHER INFORMATION: primer

<400> SEQUENCE: 104
gatctcacat tcgataaccc g                                        21

<210> SEQ ID NO 105
<211> LENGTH: 23
<212> TYPE: DNA
<213> ORGANISM: Artificial Sequence
<220> FEATURE:
<223> OTHER INFORMATION: primer

<400> SEQUENCE: 105
tgtgtttggt ttgtaaggtg tgt                                      23

<210> SEQ ID NO 106
<211> LENGTH: 26
<212> TYPE: DNA
<213> ORGANISM: Artificial Sequence
<220> FEATURE:
<223> OTHER INFORMATION: primer

<400> SEQUENCE: 106
aaacaaaatt caaatcaaca tataca                                   26

<210> SEQ ID NO 107
<211> LENGTH: 20
<212> TYPE: DNA
<213> ORGANISM: Artificial Sequence
<220> FEATURE:
<223> OTHER INFORMATION: primer

<400> SEQUENCE: 107
tgagagtagc ggtagtcggc                                          20

<210> SEQ ID NO 108
<211> LENGTH: 20
<212> TYPE: DNA
<213> ORGANISM: Artificial Sequence
<220> FEATURE:
<223> OTHER INFORMATION: primer

<400> SEQUENCE: 108
aaaaactcta tcgcccaacg                                          20

<210> SEQ ID NO 109
<211> LENGTH: 25
<212> TYPE: DNA
<213> ORGANISM: Artificial Sequence
<220> FEATURE:
<223> OTHER INFORMATION: primer

<400> SEQUENCE: 109
agaggaagtg agagtagtgg tagtt                                    25
```

<210> SEQ ID NO 110
<211> LENGTH: 22
<212> TYPE: DNA
<213> ORGANISM: Artificial Sequence
<220> FEATURE:
<223> OTHER INFORMATION: primer

<400> SEQUENCE: 110
ccaacataaa accacaacaa ca                                              22

<210> SEQ ID NO 111
<211> LENGTH: 22
<212> TYPE: DNA
<213> ORGANISM: Artificial Sequence
<220> FEATURE:
<223> OTHER INFORMATION: primer

<400> SEQUENCE: 111
tgagaagttt gatgggaatc gc                                              22

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
acgacaacgc tactccgacg                                                 20

<210> SEQ ID NO 113
<211> LENGTH: 22
<212> TYPE: DNA
<213> ORGANISM: Artificial Sequence
<220> FEATURE:
<223> OTHER INFORMATION: primer

<400> SEQUENCE: 113
tgagaagttt gatgggaatt gt                                              22

<210> SEQ ID NO 114
<211> LENGTH: 22
<212> TYPE: DNA
<213> ORGANISM: Artificial Sequence
<220> FEATURE:
<223> OTHER INFORMATION: primer

<400> SEQUENCE: 114
tccaacacaa acacacaaaa ca                                              22

<210> SEQ ID NO 115
<211> LENGTH: 26
<212> TYPE: DNA
<213> ORGANISM: Artificial Sequence
<220> FEATURE:
<223> OTHER INFORMATION: primer

<400> SEQUENCE: 115
gttatttcgg ttatattgtt tttcgc                                          26

<210> SEQ ID NO 116
<211> LENGTH: 20
<212> TYPE: DNA
<213> ORGANISM: Artificial Sequence
<220> FEATURE:
<223> OTHER INFORMATION: primer

<400> SEQUENCE: 116
acccgaccaa aaaccaaacg                                             20

<210> SEQ ID NO 117
<211> LENGTH: 25
<212> TYPE: DNA
<213> ORGANISM: Artificial Sequence
<220> FEATURE:
<223> OTHER INFORMATION: primer

<400> SEQUENCE: 117
tgttgttgtt ttgtgttgtt atttt                                       25

<210> SEQ ID NO 118
<211> LENGTH: 21
<212> TYPE: DNA
<213> ORGANISM: Artificial Sequence
<220> FEATURE:
<223> OTHER INFORMATION: primer

<400> SEQUENCE: 118
cataatccca tctcccaaac a                                           21

<210> SEQ ID NO 119
<211> LENGTH: 26
<212> TYPE: DNA
<213> ORGANISM: Artificial Sequence
<220> FEATURE:
<223> OTHER INFORMATION: primer

<400> SEQUENCE: 119
ttcgttgtta tggtgtttaa aatgac                                      26

<210> SEQ ID NO 120
<211> LENGTH: 23
<212> TYPE: DNA
<213> ORGANISM: Artificial Sequence
<220> FEATURE:
<223> OTHER INFORMATION: primer

<400> SEQUENCE: 120
gaactacgac tcccacaata ccg                                         23

<210> SEQ ID NO 121
<211> LENGTH: 23
<212> TYPE: DNA
<213> ORGANISM: Artificial Sequence
<220> FEATURE:
<223> OTHER INFORMATION: primer

<400> SEQUENCE: 121
ggatgttggg aggttatatt tgt                                         23

<210> SEQ ID NO 122
<211> LENGTH: 24
<212> TYPE: DNA
<213> ORGANISM: Artificial Sequence
<220> FEATURE:
<223> OTHER INFORMATION: primer

<400> SEQUENCE: 122
acctacacac taaacctcac caca                                        24

<210> SEQ ID NO 123

```
<211> LENGTH: 22
<212> TYPE: DNA
<213> ORGANISM: Artificial Sequence
<220> FEATURE:
<223> OTHER INFORMATION: primer

<400> SEQUENCE: 123
tgttgtagag tttcgagttt gc                                              22

<210> SEQ ID NO 124
<211> LENGTH: 21
<212> TYPE: DNA
<213> ORGANISM: Artificial Sequence
<220> FEATURE:
<223> OTHER INFORMATION: primer

<400> SEQUENCE: 124
tcctcactaa ccataacgac g                                               21

<210> SEQ ID NO 125
<211> LENGTH: 26
<212> TYPE: DNA
<213> ORGANISM: Artificial Sequence
<220> FEATURE:
<223> OTHER INFORMATION: primer

<400> SEQUENCE: 125
gagtgtgttg tttgttagtt ttttgt                                          26

<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126
acctcctcac accacaacca                                                 20

<210> SEQ ID NO 127
<211> LENGTH: 14
<212> TYPE: DNA
<213> ORGANISM: Artificial Sequence
<220> FEATURE:
<223> OTHER INFORMATION: primer

<400> SEQUENCE: 127
agggtggggc ggat                                                       14

<210> SEQ ID NO 128
<211> LENGTH: 23
<212> TYPE: DNA
<213> ORGANISM: Artificial Sequence
<220> FEATURE:
<223> OTHER INFORMATION: primer

<400> SEQUENCE: 128
agaggaggtg tgggcgttgg agg                                             23

<210> SEQ ID NO 129
<211> LENGTH: 14
<212> TYPE: DNA
<213> ORGANISM: Artificial Sequence
<220> FEATURE:
<223> OTHER INFORMATION: primer

<400> SEQUENCE: 129
```

```
tcccaccccg ccta                                                           14

<210> SEQ ID NO 130
<211> LENGTH: 23
<212> TYPE: DNA
<213> ORGANISM: Artificial Sequence
<220> FEATURE:
<223> OTHER INFORMATION: primer

<400> SEQUENCE: 130
tctcctccac acccgcaacc tcc                                                 23

<210> SEQ ID NO 131
<211> LENGTH: 12
<212> TYPE: DNA
<213> ORGANISM: Artificial Sequence
<220> FEATURE:
<223> OTHER INFORMATION: primer

<400> SEQUENCE: 131
tcccaccccr cc                                                             12

<210> SEQ ID NO 132
<211> LENGTH: 18
<212> TYPE: DNA
<213> ORGANISM: Artificial Sequence
<220> FEATURE:
<223> OTHER INFORMATION: primer

<400> SEQUENCE: 132
tccacrcccr caacaacc                                                       18

<210> SEQ ID NO 133
<211> LENGTH: 10
<212> TYPE: DNA
<213> ORGANISM: Artificial Sequence
<220> FEATURE:
<223> OTHER INFORMATION: primer

<400> SEQUENCE: 133
aggaagagag                                                                10

<210> SEQ ID NO 134
<211> LENGTH: 31
<212> TYPE: DNA
<213> ORGANISM: Artificial Sequence
<220> FEATURE:
<223> OTHER INFORMATION: primer

<400> SEQUENCE: 134
cagtaatacg actcactata gggagaaggc t                                        31
```

US 9,075,063 B2

METHYLATION ANALYSIS TO DETERMINE THE PRESENCE OF CANCER CELLS

CROSS-REFERENCE TO RELATED APPLICATION

This is a continuation of Application of PCT/JP2010/061164, filed on Jun. 30, 2010, now abandoned.

BACKGROUND OF THE INVENTION

1. Field of the Invention

The present invention relates to a method for determination of the presence of cancer cells in a biological sample, to a method for determination of the prognosis of a patient having cancer, specifically colorectal cancer, and to marker genes used for these methods.

2. Description of the Related Art

Genomic DNAs of higher eukaryotes may sometimes undergo methylation in the 5-position of C (cytosine) among other bases constituting DNAs. Such DNA methylation in higher eukaryotes functions as a mechanism for suppression of expression of genetic information. For example, when a region containing many CpGs (CpG islands), which is often found in promoter regions of certain genes, is methylated, transcription of these genes may be suppressed. On the other hand, when a CpG island is not methylated, a transcription factor can bind to the promoter region and the gene can be transcribed.

Accordingly, DNA methylation is one of control mechanisms of gene expression. DNA methylation plays important roles in various physiological and pathological phenomena such as early embryonic development, expression of tissue specific genes, genomic imprinting and X chromosome inactivation which are characteristic to mammals, stabilization of chromosomes, synchronization of DNA replication and the like.

It has been recently revealed that gene silencing due to DNA methylation is involved in cancer development and progression (see Feinberg A P. and Tycko B., Nat Rev Cancer, Vol. 4, 143-153 (2004); and Jones P A. and Baylin S B., Cell, Vol. 128, 683-692 (2007)).

In the medical field, in order to decide therapeutic strategy for cancer, not only early detection of cancer but also prediction on possibilities of post-operative cancer recurrence or metastasis or on post-operative survival rate of patients for a predetermined period is important; thus it is important to establish a method for determination of prognosis. Prognosis has been conventionally determined based on the evaluation on differentiation states of tumor tissues obtained by operations or biopsies, although it has been unknown whether or not differentiation states is an independent prognosis factor. In addition, histological determination of differentiation states relies on subjective decisions by observers, making the prognosis determination inaccurate.

Especially in the case of colorectal cancer which is mainly represented by well-differentiated adenocarcinoma rather than moderately- or poorly-differentiated adenocarcinoma, prognosis determination may take little account of histology itself. Prognosis determination of colorectal cancer has been difficult because differentiation states of some cases are difficult to be evaluated, making histological diagnosis ambiguous (see Japanese Unexamined Patent Publication Nos. 2001-165933 and 2005-69846).

SUMMARY OF THE INVENTION

In view of foregoing, an object of the present invention is to provide a method for convenient determination of the presence or absence of cancer cells and a method for determination of the prognosis of a cancer patient by analyzing methylation status of a DNA in a biological sample.

The present inventors have investigated for genes whose methylation status is specific for genomic DNA of cancer patients by comparing methylation status of CpG sites of genomic DNAs of cancer patients and non-cancer subjects, and saw the opportunity to use identified genes for genetic markers of cancer.

The present inventors have first identified genes whose promoter region is methylated from genomic DNAs obtained from cell lines.

The present inventors then selected, among the identified genes whose promoter region is methylated, the genes whose expression is low or absent in the cell lines as silencing genes.

The present inventors have further analyzed methylation status of the silencing genes in cancer tissues and normal tissues, identified the genes whose extent of methylation is different between these tissues and found that these genes can be used as marker genes for determination of the presence of cancer cells in biological samples, thereby completing the present invention.

In addition, the present inventors have found that colorectal cancer patients having certain methylated genes among the silencing genes correspond to the cases of high microsatellite instability (hereinafter also referred to as "MSI"). It is generally known that colorectal cancer patients with high MSI have a favorable prognosis (see Popat S. et al., J Clin Oncol, vol. 23, 609-613 (2005)). The present inventors have found that these genes can be used as marker genes for determination of the prognosis of colorectal cancer patients, thereby completing the present invention.

Accordingly, the present invention provides a method for determination of the presence or absence of cancer cells in a biological sample obtained from a subject comprising the steps of:

extracting DNA from the biological sample;

analyzing methylation status of a CpG site in at least one gene selected from a group consisting of collagen, type IV, alpha 2 (COL4A2); aldehyde oxidase 1 (AOX1); dual specificity phosphatase 26 (DUSP26); EGF-like repeats and discoidin 1-like domains 3 (EDIL3); EF-hand domain family, member D1 (EFHD1); engulfment and cell motility 1 (ELMO1); storkhead box 2 (STOX2); and zinc finger protein 447 (ZNF447) contained in the DNA obtained from the step of extracting; and determining the presence or absence of cancer cells in the biological sample based on a result obtained from the step of analyzing.

The present invention also provides a method for determination of the prognosis of a colorectal cancer patient comprising the steps of:

extracting DNA from a biological sample obtained from the patient;

analyzing methylation status of a CpG site in at least one gene selected from the group consisting of inhibitor of DNA binding 4, dominant negative helix-loop-helix protein (ID4); lysyl oxidase (LOX); and myocardin (MYOCD) contained in the DNA obtained from the step of extracting; and determining the prognosis of the patient based on a result obtained from the step of analyzing.

The present invention further provides a marker gene for determination of the presence or absence of cancer cells by methylation analysis, selected from the group consisting of AOX1, COL4A2, DUSP26, EDIL3, EFHD1, ELMO1, STOX2 and ZNF447.

The present invention also provides a marker gene for determination of the prognosis of a colorectal cancer patient by methylation analysis, selected from the group consisting of ID4, LOX and MYOCD.

According to the method for determination of the presence or absence of cancer cells in a biological sample (hereinafter also referred to as "the present method 1") and the method for determination of the prognosis of a colorectal cancer patient (hereinafter also referred to as "the present method 2") of the present invention, the presence or absence of cancer cells and the prognosis of colorectal cancer patients can be conveniently determined by analyzing methylation status of the marker gene for determination of the presence or absence of cancer cells and the marker gene for determination of the prognosis of the present invention.

BRIEF DESCRIPTION OF THE DRAWINGS

FIG. 1A shows IVT products are cleaved by RNase A at a position between a base and uracil (U) or thymine (T) adjacent to the base and SEQ ID NO: 127 (AGGGTGGGGCGGAT), SEQ ID NO: 128 (AGAGGAGGTGTGGGCGTTGGAGG), SEQ ID NO: 129 (TCCCACCCCGCCTA), and SEQ ID NO: 130 (TCTCCTC-CACACCCGCAACCTCC); FIG. 1B shows peaks obtained by mass spectrometry can be assigned to portions of the marker gene candidates having certain base sequences; and FIG. 1C shows SEQ ID NO: 131 (TCCCACCCCRCC where R is A or G) and SEQ ID NO: 132 (TCCACRCCCRCAA-CAACC where R is A or G) and that when one CpG site in a DNA fragment in a sample is methylated, a peak obtained in MassARRAY® shifts 16 kDa toward the higher mass side (right hand side) (see the left panel in FIG. 1C), while when two CpG sites are methylated in the analysis of a DNA fragment having more than one CpG site, the shift is 32 kDa (see the right panel in FIG. 1C) and when three CpG sites are methylated, the shift is 48 kDa.

DETAILED DESCRIPTION OF THE EMBODIMENTS

Figure 1:
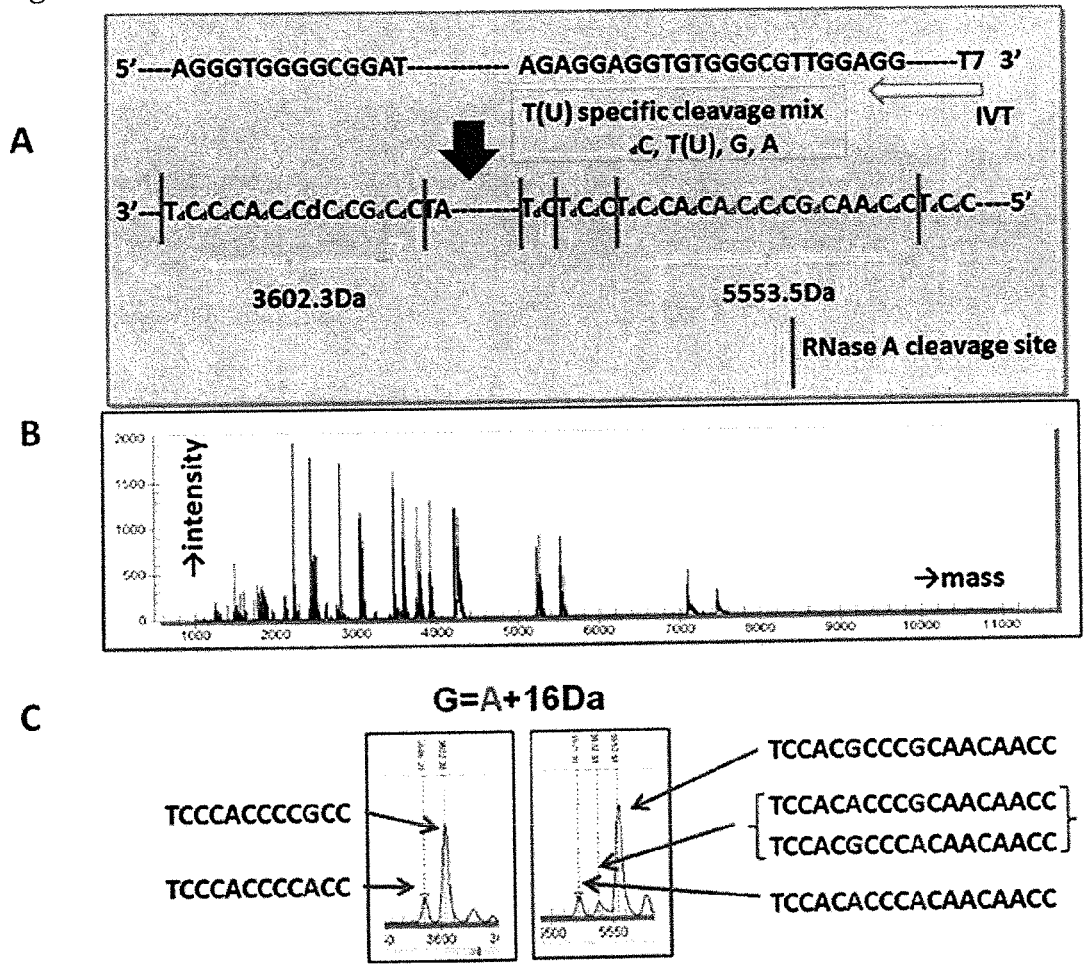
FIG. 1 is schematic representations showing principle of MassARRAY® analysis in which the methylation status of DNA is determined (FIGS. 1A and 1B)

As used herein, "CpG site" means a site in a base sequence where cytosine (C) and guanine (G) are adjacent in this order from 5'-3' direction. A letter "p" in "CpG" represents a phosphodiester bond between cytosine and guanine.

It is known that mammalian genomic DNA undergoes methylation modification in CpG sites. It is also known that CpG sites are mainly found in promoter regions of genes. As used herein, "CpG site" is intended to include all CpG sites present in all regions involved in expression of a gene in question including the base sequence of the gene and the promoter region of the gene.

As used herein, "analyze methylation status" is intended to mean analysis of presence or absence of methylation in at least one CpG site in a marker gene, or analysis of rate of methylated CpG sites relative to all CpG sites or certain CpG sites in the marker gene, i.e. analysis of methylation rate.

Methylation rate also means a value obtained from calculation of an area ratio between a peak derived from a methylated DNA fragment and a peak derived from a non-methylated DNA fragment of a marker gene resulting from analysis of methylation status of DNA by MassARRAY® which is described hereinafter. According to MassARRAY® analysis, a plurality of CpG sites in the DNA fragment is collectively analyzed as a "CpG unit" and methylation rate is calculated from an area ratio between the respective resulting peaks.

As used herein, "determine the prognosis of a colorectal cancer patient" intends to determine the vital prognosis of the colorectal cancer patient. When a colorectal cancer patient "has a favorable prognosis", the colorectal cancer patient has a favorable vital prognosis, and preferably a favorable survival rate or event-free survival for a predetermined period (preferably 5 to 10 years) after the definitive diagnosis or operation.

The term "microsatellite" means a repetitive sequence, particularly a repetitive sequence consisting of a unit of a few bases, located on a genome of a nucleus or organelles of a cell.

In tumor cells, control mechanisms of DNA replication, particularly a mismatch correction pathway is damaged and therefore the number of microsatellites increases or decreased with high frequency upon mitoses of tumor cells. This instability of the number of microsatellites is referred to as "microsatellite instability (MSI)".

MSI can be determined by analyzing base sequences of five MSI markers (BAT25, BAT26, D5S346, D2S123 and D17S250) recommended by NCI (National Cancer Institute) Workshop (see Boland C. R. et al., Cancer Res, vol. 58, 5248-5257 (1998)).

MSI-High (MSI-H) is assigned when MSI is detected in two or more markers among above five markers, MSI-Low (MSI-L) when MSI is detected in one of the markers and microsatellite stable (MSS) when no MSI is detected in any of these markers.

The marker genes for determination of the presence or absence of cancer cells used in the present method 1 are COL4A2, AOX1, DUSP26, EDIL3, EFHD1, ELMO1, STOX2 and ZNF447.

The above marker genes have been identified from biological samples derived from colorectal cancer. Esteller M. reports that many of the genes which are methylated in one type of malignant tumor are found to have abnormal methylation also in other types of malignant tumors (see Nature Review Genetics, Vol. 8, 286-298 (2007)).

Accordingly, the above marker genes may be methylated in various carcinomas. Thus, the present method 1 utilizing these marker genes is predicted to allow determination of the presence or absence of cancer cells derived from not only colorectal cancer but also gastric cancer, lung cancer, breast cancer, oral cancer, prostate cancer, renal cancer, bladder cancer, uterine cancer, ovarian cancer, leukemia and the like.

In the step of extraction of the present method 1, DNA is extracted from a biological sample obtained from a subject.

The biological sample includes any sample containing DNA of a subject without limitation and is preferably a sample containing genomic DNA, e.g. a clinical specimen. The clinical specimen specifically includes blood, serum, lymphocytes, urine, nipple discharge, tissues obtained from operations or biopsies.

DNA can be extracted from a biological sample by well-known extraction methods including, for example, a method comprising mixing the biological sample with a treatment solution containing a surfactant for solubilizing cells or tissues (sodium cholate, sodium dodecyl sulfate etc.), physically treating (agitation, homogenization, ultrasonication etc.) the mixture to release DNA contained in the biological sample into the solution, centrifuging the solution and obtaining the supernatant, and extracting the supernatant with phenol/chloroform. The obtained DNA may be further purified according to well-known methods. The extraction and purification of DNA from a biological sample can also be carried out with commercially available kits.

It is preferred that the step of extracting further comprises the step of fragmenting the extracted DNA. Fragmentation of DNA contained in a biological sample into an appropriate length may facilitate the procedures of MeDIP and bisulfite treatment described hereinafter in the next step of analyzing methylation status.

Fragmentation of DNA can be carried out by ultrasonication, alkaline treatment, restriction enzyme treatment and the like. For example, DNA can be fragmented by alkaline treatment with sodium hydroxide by adding a solution of sodium hydroxide to the final concentration of 0.1 to 1.0N to a DNA solution and incubating the mixture at 10 to 40° C. for 5 to 15 min. Restriction enzyme treatment nay be carried out with a restriction enzyme appropriately selected according to the base sequence of DNA, e.g. MseI or BamHI.

In the step of analyzing of the present method 1, methylation status of a CpG site in at least one gene selected from the group consisting of COL4A2, AOX1, DUSP26, EDIL3, EFHD1, ELMO1, STOX2 and ZNF447, among genes comprised in the extracted DNA.

In this step of analyzing, presence or absence of methylation in at least one CpG site in the above marker gene may be analyzed. In this case, more than one CpG site is preferably analyzed for methylation in order to improve the determination accuracy in the subsequent step of determining.

In this step of analyzing, methylation rate of the above marker gene may be analyzed.

The marker gene to be analyzed may be any one of the above nine genes. However, in order to improve the determination accuracy in the subsequent step of determining, more than one marker gene is preferably analyzed.

The base sequences of the above marker genes are well-known. The base sequences are available from well-known databases such as those provided by Unigene (National Center for Biotechnology Information (NCBI)). Unigene codes, NCBI codes and Sequence ID Numbers of the above marker genes are shown in Table 1.

TABLE 1

| Gene symbol | Unigene code | NCBI code | SEQ ID NO: |
|---|---|---|---|
| COL4A2 | Hs.508716 | NM_001846.2 | 84 |
| AOX1 | Hs.406238 | NM_001159.3 | 85 |
| DUSP26 | Hs.8719 | NM_024025.1 | 86 |
| EDIL3 | Hs.482730 | NM_005711.3 | 87 |
| EFHD1 | Hs.516769 | NM_025202.3 | 88 |
| ELMO1 | Hs.656638 | NM_014800.9 | 89 |
| STOX2 | Hs.696657 | NM_020225.1 | 90 |
| ZNF447 | Hs.235390 | NM_001145542.1 | 91 |
| ID4 | Hs.519601 | NM_001546.2 | 92 |
| LOX | Hs.102267 | NM_002317.4 | 93 |
| MYOCD | Hs.567641 | NM_001146313.1 | 94 |

Many methods are well-known for analyzing methylation status of CpG sites in genes. Any analyzing methods may be used in the step of analyzing without limitation, however, the step preferably comprises the step of distinguishing between methylated DNA and non-methylated DNA, the step of amplifying DNA and the step of separately detecting methylated DNA and non-methylated DNA.

The step of distinguishing between methylated DNA and non-methylated DNA may include methylation sensitive restriction enzyme treatment, MeDIP, bisulfite treatment and the like.

The step of amplifying DNA may include PCR amplification, quantitative PCR amplification, IVT (in vitro transcription) amplification, SPIA™ amplification and the like.

The step of separately detecting methylated DNA and non-methylated DNA may include electrophoresis, sequencing, microarray analysis, mass spectrometry and the like.

The above "MeDIP" is a method for concentrating methylated DNA in samples by immunoprecipitation using anti-methylated cytosine antibody, anti-methylated cytidine antibody or an antibody that specifically recognizes a methylated DNA-binding protein. The concentrated methylated DNA is subjected to amplification by PCR amplification or IVT amplification and then analyzed for DNA methylation using microarray; these procedures are called as MeDIP-chip method.

The above "bisulfite treatment" is a treatment for converting non-methylated cytosine (C) in DNA to uracil by deamination after addition of a solution of a bisulfite such as sodium, potassium, calcium or magnesium bisulfite in a solvent to a DNA solution.

Bisulfites do not affect methylated cytosines, resulting in the absence of base conversion as described above. Thus, difference in methylation status in DNA can be converted into difference in base sequences (C to U) after the bisulfite treatment.

Non-methylated cytosine in DNA can be converted to uracil by the bisulfite treatment followed by sequencing of the DNA and detection of difference in base sequences to analyze methylation status of the DNA. These procedures are called as bisulfite sequencing.

Methylation status of DNA can also be analyzed based on presence or absence of PCR products after PCR amplification using specific primers for a base sequence which is different in methylated DNA and non-methylated DNA. This method is called as methylation specific PCR (MSP).

Methylated DNA can be analyzed by utilizing the bisulfite treatment in other known methods than the above such as COBRA (Combined Bisulfite Restriction Analysis), Methylation-sensitive Single-Nucleotide Primer Extension, quantitative MSP, pyrosequencing and the like.

The DNA in which non-methylated cytosine is converted to uracil by the above bisulfite treatment is then used as a template in PCR amplification using primers specific for a base sequence of a target gene and the resulting PCR product is further subjected to IVT amplification, thereby converting methylated cytosine and uracil to guanine (G) and adenine (A), respectively. The resulting IVT product is then cleaved with RNase A and the difference in mass between G and A (16 kDa) of the obtained nucleic acid fragments is detected in a MALDI-TOF (matrix assisted laser desorption/ionization-time-of-flight) mass spectrometer, thereby allowing analysis of methylation status of DNA. This method is called as MassARRAY® analysis (see FIGS. 1A and 1B).

When, for example, one CpG site in a DNA fragment in a sample is methylated, a peak obtained in MassARRAY® shifts 16 kDa toward the higher mass side (right hand side) (see the left panel in FIG. 1C). When two CpG sites are methylated in the analysis of a DNA fragment having more than one CpG site, for example, the shift is 32 kDa (see the right panel in FIG. 1C) and when three CpG sites are methylated, the shift is 48 kDa.

In MassARRAY® analysis, more than one CpG site in a DNA fragment to be analyzed are collectively analyzed as a "CpG unit", therefore it is not possible to specify which CpG sites are methylated.

When the analysis employs PCR amplification, primers for the amplification may be appropriately designed by a person skilled in the art according to the base sequence of a gene to be analyzed. However, in order to carry out quantitative methylation analysis, the primers preferably contain no CpG site or one CpG site in their 5' side. The primers for amplification may be optionally added with a tag sequence, a T7 promoter sequence and the like.

When methylation of the marker gene is analyzed with microarray, the microarray to be used may be prepared by immobilizing one or more nucleic acid probes complementary to the base sequence of the marker gene on a substrate using a well-known method in the art. Commercially available microarrays may also be used.

In the analysis using microarray, DNA contained in a biological sample is preferably labeled with a labeling substance well-known in the art. Thus, the present method 1 preferably comprises the additional step of labeling the extracted DNA. The step of labeling is preferably carried out after the step of amplification of DNA because all DNA contained in the biological sample may be labeled.

The labeling substance may include fluorescent substances, haptens such as biotin, radioactive substances and the like. The fluorescent substances include Cy3, Cy5, Alexa Fluor™, FITC and the like. The labeling of DNA to be analyzed facilitates measurement of signal obtained from the probes on microarray. The method for labeling DNA with the labeling substance is well-known in the art.

Signal may be any signal that is appropriate according to the type of microarrays. Signal may be, for example, electric signal generated upon hybridization of a DNA fragment with a probe on a microarray, or fluorescence or luminescence generated from the labeling substance when DNA to be analyzed is labeled as described above.

The above signals may be detected with a scanner equipped with conventional microarray instruments. The scanner may include, for example, GeneChip® Scanner 3000 7G (Affymetrix, Inc.).

In the step of determining of the present method 1, presence or absence of cancer cells in the biological sample is determined based on a result obtained from the step of analyzing. In the step of determining, it may be determined that cancer cells are present in the biological sample obtained from a subject when the result showing that a CpG site is methylated in the marker gene is obtained. The determination may be made based on the result of one CpG site located in the marker gene. However, in order to improve the determination accuracy, the determination is preferably made based on the result of more than one CpG site.

In the step of determining, it may be determined that cancer cells are present in the biological sample obtained from a subject when methylation rate of the marker gene obtained in the step of analyzing is higher than a pre-determined cut-off value. The cut-off value may be appropriately determined without limitation and is preferably in the range of 1 to 40%.

In the step of extracting of the present method 2, DNA is extracted from a biological sample obtained from a colorectal cancer patient. The colorectal cancer patient may be pre-operative or post-operative and may be receiving or have received chemotherapy.

The biological sample includes any sample containing DNA of a colorectal cancer patient without limitation and is preferably a sample containing genomic DNA, e.g. a clinical specimen. The clinical specimen specifically includes blood, serum, lymphocytes, urine, nipple discharge, tissues obtained from operations or biopsies.

When the biological sample obtained is a tissue, the tissue preferably contains cancer cells.

In the step of extracting, DNA can be extracted from the biological sample in the same manner as the step of extracting of the present method 1.

The step of extracting preferably comprises, as similar to the step of extracting of the present method 1, the additional step of fragmenting DNA by ultrasonication, alkaline treatment, restriction enzyme treatment and the like.

In the step of analyzing of the present method 2, methylation status of a CpG site in at least one gene selected from the group consisting of ID4, LOX and MYOCD comprised in DNA obtained from the step of extracting is analyzed.

In this step of analyzing, presence or absence of methylation in at least one CpG site in the above marker gene may be analyzed. In this case, more than one CpG site is preferably analyzed for methylation in order to improve the determination accuracy in the subsequent step of determining.

In this step of analyzing, methylation rate of the above marker gene may be analyzed.

The marker gene to be analyzed may be any one of the above three genes. However, in order to improve the determination accuracy in the subsequent step of determining, more than one marker gene is preferably analyzed.

The base sequences of the above three marker genes are well-known and are available from well-known databases such as Unigene described above. Unigene codes of these three marker genes are shown in Table 1.

The step of analyzing of the present method 2 can be carried out in the similar manner as described for the step of analyzing of the present method 1. Any analysis methods may be used in the step of analyzing without limitation, however, the step preferably comprises the step of distinguishing between methylated DNA and non-methylated DNA, the step of amplifying DNA and the step of separately detecting methylated DNA and non-methylated DNA.

In the step of determining of the present method 2, the prognosis of the cancer patient is determined based on a result obtained from the step of analyzing.

In the step of determining, it may be determined that the colorectal cancer patient has a favorable prognosis when the result showing that a CpG site is methylated in the marker gene is obtained. The determination may be made based on the result of one CpG site located in the marker gene. However, in order to improve the determination accuracy, the determination is preferably made based on the result of more than one CpG site.

In the step of determining, it may be determined that the colorectal cancer patient has a favorable prognosis when methylation rate of the marker gene obtained in the step of analyzing is higher than a predetermined cut-off value. The cut-off value may be appropriately determined without limitation and is preferably in the range of 1 to 40%.

The present invention is further described in detail referring to the following Examples, which do not limit the present invention.

Example 1

Investigation for Marker Gene Candidates by MeDIP-Chip

The present inventors thought that methylated CpG sites located within 1 kb upstream and downstream of a transcription initiation site of genes are important for gene expression and that genes having a candidate methylation site (CMS) in such region may be possible markers. Thus, they investigated for such genes from a colorectal cancer cell line HCT116 by MeDIP-chip technique.

The specific procedures in Example 1 followed the instructions attached to the kits and reagents and the description by Hayashi H. et al., Hum Genet., vol. 120, 701-711 (2007).

(1) MeDIP Procedure

Genomic DNA was extracted from the colorectal cancer cell line HCT116 by using QIAAMP® DNA Micro kit (QIAGEN) according to the attached instruction. The obtained genomic DNA (6 μg) was processed in an ultrasonicator UD-201 (Tomy Seiko Co., Ltd.) for 20 seconds to fragment the genomic DNA to the size of 200 to 800 bp. The DNA fragments were denatured by heating them at 95° C. for 10 minutes followed by rapid cooling to 4° C. to obtain single-stranded genomic DNA.

The resulting denatured DNA (1 μg) was diluted with 300 μl immunoprecipitation buffer (20 mM Tris-HCl, pH 8.0; 2 mM EDTA, pH 8.0; 150 mM NaCl; and 1% Triton X-100), and added with 103 μl of a suspension of Protein A SEPHAROSE® beads (GE Healthcare) before rotation at 4° C. for 30 minutes for pre-clear treatment. The supernatant was collected after centrifugation.

The above suspension of beads had the following composition.

Immunoprecipitation buffer: 50 μl
50% Protein A SEPHAROSE® beads: 50 μl
BSA solution (Sigma): 1 μl
tRNA solution (Sigma): 1 μl
Protease inhibitor (Sigma): 1 μl To the collected supernatant was added a solution of anti-methylated cytosine antibody BI-MECY-0500 (Eurogentec) previously subjected to rotation at 4° C. for 30 minutes and the mixture was subjected to rotation at 4° C. for 3 hours.

The solution of the antibody had the following composition.

Immunoprecipitation buffer: 450 μl
50% Protein A SEPHAROSE® beads: 50 μl
Anti-methylated cytosine antibody: 10 μg
BSA solution: 1 μl
tRNA solution: 1 μl
Protease inhibitor: 1 μl Beads were collected by centrifugation, washed twice with the immunoprecipitation buffer and three times with a TE buffer (10 mM Tris-HCl, pH 8.0 and 1 mM EDTA, pH 8.0) followed by elution with an elution buffer (25 mM Tris-HCl, pH 8.0; 10 mM EDTA, pH 8.0; and 0.5% SDS) to obtain methylated genomic DNA precipitated as a complex with the anti-methylated cytosine antibody and beads.

To the resulting solution of methylated genomic DNA was added DTT to the final concentration of 250 nM and the mixture was subjected to rotation at room temperature for 30 minutes before incubation at 65° C. for 30 minutes. The solution was subjected to phenol/chloroform and ethanol precipitation to purify methylated genomic DNA derived from HCT116 cells.

(2) IVT Amplification

The methylated genomic DNA obtained in the above (1) was subjected to dephosphorylation of DNA terminal with CIP (Calf intestine phosphatase; New England Biolab) before attachment of dTTP to the 3' terminal of the DNA using TdT (Terminal transfer; ROCHE).

A T7-polyA primer was annealed to the obtained DNA and double-stranded DNA was synthesized with DNA polymerase I (Invitrogen). The sequence of the T7-polyA primer is shown below.

(SEQ ID NO: 83)
5'-GCATTAGCGGCCGCGAAATTAATACGACTCACTATAGGGA

G(A)$_{18}$B-3'

The resulting double-stranded DNA to which the T7 promoter sequence was added was used as a template in linear amplification using T7RNA polymerase (MEGAscript® T7 kit; Ambion) before purification with RNEASY® Mini kit (QIAGEN) to obtain cRNA.

The cRNA was used as a template in order to obtain cDNA with SuperScript™ II RT (Invitrogen) and random primers (Invitrogen).

The T7-polyA primer was annealed to the cDNA and subjected to reactions with DNA polymerase I and then with T4 DNA polymerase (NEB) to synthesize double-stranded DNA.

The double-stranded DNA to which the T7 promoter sequence was added was used as a template in linear amplification using T7RNA polymerase (MEGAscript® T7 kit) before purification with RNEASY® Mini kit to obtain cRNA.

The cRNA was used as a template in order to obtain cDNA with SuperScript™ II RT (Invitrogen) and random primers (Invitrogen).

The cDNA was subjected to reactions with DNA polymerase I, *E. coli* DNA ligase (Invitrogen) and then RNase H (Ambion) to synthesize double-stranded DNA.

The double-stranded DNA was treated with RNase H and RNase cocktail (Ambion) to degrade RNA before purification of the double-stranded DNA with QIAQUICK® Purification kit (QIAGEN).

(3) Microarray Analysis

The double-stranded DNA amplified from methylated genomic DNA derived from HCT116 cells according to the above (2) was fragmented with DNase I (Invitrogen) to the size of 50 to 100 bp before biotin-labeling with Biotin-N11-ddATP (Perkin Elmer).

The DNA fragments labeled with biotin were brought into contact with GeneChip® Human Promoter 1.0R Array (Affymetrix, Inc.) for hybridization with probes on the microarray. The subsequent staining, washing and scanning (measurement of signal) were carried out according to the instructions provided by Affymetrix, Inc.

The values obtained by signal measurement were analyzed by Wilcoxon rank-sum test in the window of 550 bp. The regions having less than 0.01 of significance probability ($p<0.01$) were considered as candidate methylation sites (CMS) where probes on the microarray specifically bound to the methylated DNA fragments.

As a result, 3814 genes were obtained as the genes having CMS within 1 kb upstream and downstream from a transcription initiation site of genes in HCT116 cells.

(4) Microarray Expression Analysis

In order to investigate genes whose expression in HCT116 cells is low or absent among the above 3814 genes, microarray analysis was carried out. The microarray used was GeneChip® Human Genome U133 Plus 2.0 Array (Affymetrix, Inc.) onto which probes against 38500 genes including the above 3814 genes were deposited.

From HCT116 cells, mRNA was extracted with TRIZOL® (Invitrogen) and subjected to expression analysis. The genes which had a GeneChip® score of less than 70 in the analysis were regarded as silencing genes of HCT116 cells.

As a result, 2410 genes corresponded to silencing gens.

Example 2

Investigation for Marker Gene Candidates by MassARRAY® Analysis

The present inventors randomly selected 41 genes from 2410 genes obtained in Example 1 as marker gene candidates. Methylation status of the marker gene candidates in colorectal cancer tissues and normal colonic mucosa tissues was analyzed by MassARRAY® analysis (hereinafter also referred to as "mass spectrometry").

The 41 marker gene candidates are shown in Table 2.

The specific procedures in Example 2 followed the instructions attached to the kits and reagents and the description by Ehrich M. et al., Proc Natl Acad Sci USA, vol. 102, 15785-15790 (2005) and Coolen M W. et al., Nucleic Acids Res, vol. 35, 119 (2007).

TABLE 2

| Gene No | Gene symbol | Gene title |
|---|---|---|
| 1 | ABTB2 | ankyrin repeat and BTB(POZ) domain containing 2 |
| 2 | ADAMTS1 | ADAM metallopeptidase with thrombospondin type 1 motif, 1 |
| 3 | AOX1 | aldehyde oxidase 1 |
| 4 | CDO1 | cysteine dioxygenese, type1 |
| 5 | CHFR | checkpoint with forkhead and ring finger domains |
| 6 | CIDEB | cell death-inducing DEFA-like effector b |
| 7 | CLDN23 | claudin 23 |
| 8 | COL4A2 | collagen, typeIV, alpha 2 |
| 9 | DUSP26 | dual specificity phosphatase 26 |
| 10 | EDIL3 | EGF-like repeats and discoidin 1-like domains 3 |
| 11 | EFEMP1 | EGF-containing fibulin-like extracellular matrix protein 1 |
| 12 | EFHD1 | EF-hand domain family, member D1 |
| 13 | ELMO1 | engulfment and cell motility 1 |
| 14 | EPHB1 | EPH receptor B1 |
| 15 | FBN2 | fibrillin 2 |
| 16 | FLJ23191 | chromosome4 open reading frame 31 |
| 17 | HAND1 | hand and neural crest derivatives expressed 1 |
| 18 | ID4 | inhibitor of DNA binding 4, dominant negative helix-loop-helix protein |
| 19 | IGFBP7 | insulin-like growth factor binding protein 7 |
| 20 | IRF8 | interferon reguratory factor 8 |
| 21 | KCNC2 | potassium voltage-gated channel, Shaw-related subfamily, member 2 |
| 22 | KIAA0495 | KIAA0495 |
| 23 | LOX | lysyl oxidase |
| 24 | MYOCD | myocardin |
| 25 | PCSK6 | proprotein convertase subtilisin/kexin type 6 |
| 26 | PENK | proenkephalin |
| 27 | PPP1R14A | protein phosphatase 1, regulatory (inhibitor) subunit 14A |
| 28 | PPP1R3C | protein phosphatase 1, regulatory (inhibitor) subunit 3C |
| 29 | SCAM1 | sorbin and SH3 domain containing 3 |
| 30 | SFRP1 | secreted frissled-related protein 1 |
| 31 | SLC30A10 | solute carrier family 30, member 8 |
| 32 | SLC35B3 | solute carrier family 35, member B3 |
| 33 | SPON1 | spondin 1, extracellular matrix protein |
| 34 | STOX2 | storkhead box 2 |
| 35 | THBD | thrombomodulin |
| 36 | TLE4 | transducin-like enhancer of spilit 4(E(sp1)homolog, *Drosophila*) |
| 37 | TMEFF2 | transmembrane protein with EGF-like and two follistatin-like domains 2 |
| 38 | SPG20 | spastic paraplegia 20 |
| 39 | TSPYL5 | TSPY-like 5 |
| 40 | UCHL1 | ubiquitin carboxvl-terminal esterase L1 |
| 41 | ZNF447 | zinc finger protein 447 |

(1) Preparation of Test Samples and Control Samples

As described below, CRC (colorectal cancer) specimen samples and Normal specimen samples were prepared from genomic DNA derived from colorectal cancer tissues and normal colonic mucosa tissues, respectively. In order to prepare a calibration curve for mass spectrometry, 0%, 25%, 50%, 75% and 100% methylated control samples were prepared from control genomic DNA, i.e. peripheral blood lymphocyte genomic DNA.

(i) DNA Extraction from Colorectal Cancer Tissues and Normal Colonic Mucosa Tissues From colorectal cancer tissues obtained from colorectal cancer patients (112 specimens) and normal colonic mucosa tissues (9 specimens), genomic DNA was respectively extracted using QIAAMP® DNA Micro kit (QIAGEN) and cleaved by ultrasonication in Bioruptor (COSMO BIO Co., Ltd.). The colorectal cancer specimens contained 40% or more cancer cells as determined by histopathological observations of the sections.

(ii) Preparation of 0%, 25%, 50%, 75% and 100% Methylated DNA

Human peripheral blood lymphocyte genomic DNA was amplified by using GENOMIPHI® v2 DNA amplification kit (GE Healthcare Life Science). The amplified product is non-methylated DNA. The amplified product was then cleaved by ultrasonication in Bioruptor (COSMO BIO Co., Ltd.) to obtain DNA fragments (0% methylated DNA). A portion of the DNA fragments was reacted with SssI methylase (New England Biolab) and all cytosines were methylated to obtain methylated DNA fragments (100% methylated DNA). The 0% methylated DNA and the 100% methylated DNA were mixed in certain proportions to prepare 25%, 50% and 75% methylated DNAs.

(iii) Bisulfite Treatment

The DNAs (1 μg) obtained in the above (i) and (ii) were diluted in 19 μl water, 1 μl of a 6N aqueous solution of sodium hydroxide was added to the final concentration of 0.3 N and the mixture was incubated at 37° C. for 15 minutes in order to denature DNA.

To the above DNA solutions was added 120 μl of a 3.6 M sodium bisulfite/0.6 M hydroquinone solution, and the mixtures were subjected to bisulfite treatment by performing 15 cycles of 95° C. for 30 seconds and 50° C. for 15 minutes. The reaction solutions were subjected to desalting on Wizard® DNA Clean-up System (Promega) and eluted with 50 μl of TE buffer to obtain the solutions of DNA in which non-methylated cytosine(s) was (were) converted to uracil(s).

To the DNA solutions was added 5 μl of a 3 N aqueous solution of sodium hydroxide, and the mixture was incubated at room temperature for 5 minutes before DNA purification by ethanol precipitation. Finally, DNAs were dissolved in 80 μl water to obtain CRC specimen samples and Normal specimen samples as well as 0%, 25%, 50%, 75% and 100% methylated control samples.

(2) PCR and IVT Amplifications

In this step, methylated cytosine(s) and uracil(s) in the DNAs obtained after conversion of non-methylated cytosine(s) to uracil(s) by bisulfite treatment as described above were converted to guanine(s) and adenine(s), respectively, by PCR amplification and IVT amplification.

It was confirmed that the primer sets used in PCR amplification could universally amplify both methylated DNA and non-methylated DNA, by MassARRAY® analysis described hereinafter using the control samples obtained above. The sequences of the primer sets (SEQ ID NOs: 1 to 82) for the marker gene candidates are shown in Table 3.

TABLE 3

| Gene symbol | Forward primer | SEQ ID NO: | Reverse primer | SEQ ID NO: |
|---|---|---|---|---|
| ABTB2 | GAATAGTYGTTATAATAGTTGGGATA | 1 | ACACCTCAAAACRAATACACTTAAC | 2 |
| ADAMTS1 | GTTTTTTGGGGTTTTAATGT | 3 | CTCCRACACCACTAACTCCTC | 4 |
| AOX1 | AGAYGTAAGAGGGTGTGATATAGA | 5 | AAAAAATAACRAACACCTAAAACC | 6 |
| CDO1 | TTTGGAGTTATTAGGAATGTATTA | 7 | TCCTCCRACCCTTTTTATCTA | 8 |
| CHFR | GGTTATTTTTGATTTTGATTAGG | 9 | CAAAATCCTTAAAACTTCCAAT | 10 |
| CIDEB | GGTTGAYGTTAGAATTGAAGAAG | 11 | CCCACCTAAACCTAAAAACTC | 12 |
| CLDN23 | GGTTATTTTATTTGGATGGTGT | 13 | AACTACCTAAACAACTACCTCCTAC | 14 |
| COL4A2 | TAGYGTAGGATGAGGGAGGT | 15 | CRCCTTATACAAACTAAAACTACAC | 16 |
| DUSP26 | TTTTGTAATTGGTGTAGTTTTGA | 17 | ACTATTTTAAACCATAACACACAC | 18 |
| EDIL3 | ATAAAGYGTTGAGGAAAGAGAA | 19 | CTCTACTCAAACTTTACAAACACT | 20 |
| EFEMP1 | TAGGAGTTGGTTAGAAGTTGG | 21 | ACRACTAATTCTCTTTTATCTTATCA | 22 |
| EFHD1 | GGYGGAGTGTTGTAGAGTTT | 23 | CCAACTCCTCACTAACCATAAC | 24 |
| ELMO1 | AATGTGTTTTTGGTTAGTAGGAG | 25 | AAATAACTCTACCTCTATCCTATACC | 26 |
| EPHB1 | GGAGTAGTAGTAGATAATTTAGGG | 27 | TAACTAACAATATAACACCAAAAC | 28 |
| FBN2 | GGATATTGGAAAGTTGTAAAAG | 29 | CCRCCCTCTCTCTTACTAAC | 30 |
| FLJ23191 | GTAGAGGATAAATGAGGAGTTAGAG | 31 | TCCCTTTCCAAATTCATACC | 32 |
| HAND1 | GGGAAAGTTTATAGTGGAGAGAG | 33 | CAAATCATCACTCCTTAAAAATC | 34 |
| ID4 | GGGTTTGGAGTGGTTAGTTA | 35 | CRCTCCCTCAACAACCTAAT | 36 |
| IGFBP7 | GAGAAGGTTATTATTTAGGTTAGTAA | 37 | ACTACCAACTCTTTCCCTCC | 38 |
| IRF8 | GTTAGYGGTTTTAGAAGAGGTT | 39 | CRCCCACTATACCTACCTACC | 40 |

TABLE 3-continued

Sequence of primer set

| Gene symbol | Forward primer | SEQ ID NO: | Reverse primer | SEQ ID NO: |
|---|---|---|---|---|
| KCNC2 | GAGGAGGAGTTGGTTTTTTG | 41 | AATCTCTTCTACCCCCCATAC | 42 |
| KIAA0495 | GGYGGGAAAAAGAAGGTTTTATA | 43 | ACCCRAAAACAAATATTCCAAAATAC | 44 |
| LOX | TGGTATTGTTTGGTGGAGAT | 45 | AAACTCAACAAACTAAACACCTA | 46 |
| MYOCD | GAGGAAAGAAGGAAGGGTTG | 47 | AATACAAAATCRTCTCTACCAATACC | 48 |
| PCSK6 | GGTTTTAGGGAGAAGAAGTT | 49 | RACCTACCTCCCAACATAAA | 50 |
| PENK | TYGTAGGAATGTTTTTTTTG | 51 | CTCTTTCCCTTCACATTTCA | 52 |
| PPP1R14 | AATGGATGAGTGAATGAATGAA | 53 | ACRAAAACCTAAAACAAACAC | 54 |
| PPP1R3C | GYGATGTTTAGATAGTTTTTG | 55 | ACCACAACTCCAAACCTTAC | 56 |
| SCAM1 | ATYGTTTTTGTTTTTGTTTTG | 57 | AACACTAATAACCCCCTACC | 58 |
| SFRP1 | GTTTTGTTTTTTAAGGGGTGTTGAG | 59 | ACACTAACTCCRAAAACTACAAAAC | 60 |
| SLC30A10 | GGTATTYGTTTTTTAGATTGTT | 61 | AAATAAATCCCACCTCTACAT | 62 |
| SLC35B3 | GAGGAGGAAGAGGAGGTGAT | 63 | AAAATCTAAATCCCAAACACAA | 64 |
| SPON1 | TGTTAGGTATAGAGTAGGTGGT | 65 | CAACRCTATTTTATTTCCTCC | 66 |
| STOX2 | GGTTTTAGGTTGGGGTAGTT | 67 | CCTACACATACATACTCCTACTTACT | 68 |
| THBD | TAGTTTTTTTTATTAGGATTTTTTT | 69 | CCCAAACATATTACCCAAAC | 70 |
| TLE4 | ATGTTTAGTTATTTTTGATTGGTT | 71 | RCTCAACACAACTCTAACAACAC | 72 |
| TMEFF2 | TATTTAGGGATTGGGTTTAGTTT | 73 | CCTCCTTACATCCTTACACCTC | 74 |
| SPG20 | GGGTAGAATTTAGTTTGAGTAGGT | 75 | AACTCOCACTCCCTTACACTA | 76 |
| TSPYL5 | GGAAGAGATGAAATGGTAGTAT | 77 | TCAAAAACACRCTATAACCCTA | 78 |
| UCHL1 | YGGTAGAAATAGTTTAGGGAAG | 79 | TACTCCATACACTCAAAAAACAC | 80 |
| ZNF447 | TTTATTTYGTTGTTATGGTGTTTA | 81 | CCTAACCCCTTTCCCTAAC | 82 |

In the following PCR reactions, the primer sets containing the following tag sequence and T7 promoter sequence at the 5' terminal of forward primers and reverse primers of the above primer sets were used in order to facilitate the subsequent IVT reactions.

```
Tag sequence:
                                    (SEQ ID NO: 133)
5'-AGGAAGAGAG-3'

T7 promoter sequence:
                                    (SEQ ID NO: 134)
5'-CAGTAATACGACTCACTATAGGGAGAAGGCT-3'
```

The following reagents were mixed and used for PCR reactions.

| 10 × Hot Star buffer (QIAGEN) | 0.5 µl |
| 25 mM dNTP mix | 0.04 µl |
| Hot Star Taq (5 U/µl) (QIAGEN) | 0.04 µl |
| Primer mix | 2 µl |
| DNA solution | 1 µl |
| Water | 1.42 µl |
| Total | 5 µl |

With the above reaction solution, PCR reactions were carried out under the following conditions.

94° C. for 15 minutes;
45 cycles of 94° C. for 20 seconds, 52° C. for 30 seconds and 72° C. for 1 minute; and
72° C. for 3 minutes.

The PCR products obtained as above were subjected to dephosphorylation reaction using SAP (Shrimp Alkaline Phosphatase) included in MassCLEAVE™ Reagent kit (SEQUENOM). The following reaction solution prepared according to the above kit was added and incubated at 37° C. for 3 hours to carry out IVT reaction and specific cleavage at uracil (U) or thymine (T). The obtained cleavage products were purified with Clean Resin (SEQUENOM) and the samples for mass spectrometry were obtained.

| 5 × T7 R&DNA polymerase buffer | 0.89 µl |
| T Cleavage mix | 0.24 µl |
| 100 mM DTT | 0.22 µl |
| T7 R&DNA polymerase | 0.44 µl |
| RNase A | 0.06 µl |
| RNase-free water | 3.15 µl |
| Total | 5 µl |

As shown in FIG. 1A, it has been known that IVT products are cleaved by RNase A at a position between a base and uracil (U) or thymine (T) adjacent to the base. Base sequences and mass of the cleavage products obtained as above can be predicted from the base sequences of the marker gene candidates. Based on this information, the peaks obtained by the subsequent mass spectrometry can be assigned to the portions of the marker gene candidates having certain base sequences.

(3) Analysis by Mass Spectrometer MassARRAY® (SEQUENOM)

(i) Generation of Calibration Curve

Mass spectrometry analysis was carried out twice independently for each sample for mass spectrometry obtained as the above (2) derived from the specimen samples. Calibration curves were generated for respective primer sets from the analysis results and correlation coefficients were calculated. The calibration curves obtained from control samples amplified with the above primer sets were linear, confirming that the respective primer sets could universally amplify both methylated DNA and non-methylated DNA.

(ii) Analysis of Samples Derived from Specimen Samples

The samples for mass spectrometry derived from the specimen samples obtained as the above (2) were analyzed by mass spectrometry and peaks of respective cleavage products were obtained. Each peak obtained was assigned to the portions of the base sequences of the marker gene candidates. For cleavage products derived from the same base sequence, methylation rate was calculated from a ratio between the area of the peak of the cleavage product containing methylated CpG site(s) and the area of the peak of the cleavage product containing no methylated CpG site. This calculation is illustrated by referring to the left panel of FIG. 1C. When the area ratio between the peak of non-methylated cleavage product (left peak) and the peak of methylated cleavage product (right peak) is 1:3, methylation rate of the DNA fragment having the indicated sequence is calculated as 75% (3/(1+3)=0.75). Such calculation of methylation rate was carried out for all cleavage products. In theory, methylation rate is 100% when all CpG sites in a cleavage product are methylated and 0% when all CpG sites are non-methylated.

The cleavage products having the correlation coefficient of more than 0.9 as calculated in the above (i) for methylation rate obtained as above were used for the subsequent data analysis. The cleavage products were excluded whose methylation rate was calculated in less than 102 specimens (90%) among 112 colorectal cancer tissues.

In order to take account of the number of CpG sites in each of the marker gene candidates and the number of CpG sites in the cleavage products of the each gene, methylation rate for each marker gene candidate was calculated as a weighted average of the methylation rates of the cleavage products which were not excluded.

(iii) Setting of Cut-Off Value and Calculation of Methylation Frequency

According to the methylation rates obtained as above, a cut-off value was set as 35% in order to determine whether or not the marker gene candidate contained in the specimens is methylated. Thus, when methylation rate of a gene is higher than 35%, it is determined that the gene is methylated. This value was set by taking account of the fact that the colorectal cancer specimens had 40% cancer cell content.

For the colorectal cancer specimens (112 specimens) and normal colonic mucosa specimens (9 specimens), methylation of the above 41 marker gene candidates were determined based on the cut-off value (35%) and methylation rates thereof calculated as above. For each gene, the number of specimens in which the gene is methylated was count among the population of colorectal cancer specimens and the population of normal colonic mucosa specimens, and proportion of methylation-positive specimens relative to the total number of specimens was calculated according to the following equation. The results are shown in Table 4.

(Proportion of methylation-positive specimens)(%)= ((Number of methylation-positive specimens in the population)/(Total number of specimens in the population))×100

TABLE 4

| Group | | Gene symbol | Normal (n = 9) Proportion of methylation-positive specimens (%) | CRC (n = 112) Proportion of methylation-positive specimens (%) | CRC (n = 112) Number of methylation-positive specimens | Difference in methylation frequency between CRC and Normal (%) |
|---|---|---|---|---|---|---|
| A | * | TSPYL | 0% | 95% | 106 | 95% |
| | * | COL4A2 | 0% | 95% | 106 | 95% |
| | * | ADAMTS1 | 0% | 84% | 92 | 84% |
| | * | SPG20 | 0% | 80% | 90 | 80% |
| | * | TMEFF2 | 0% | 73% | 81 | 73% |
| | * | CIDEB | 0% | 71% | 80 | 71% |
| | * | EDIL3 | 0% | 68% | 76 | 68% |
| | * | EFEMP1 | 0% | 65% | 73 | 65% |
| | * | PPP1R14A | 0% | 61% | 68 | 61% |
| | * | UCHL1 | 0% | 61% | 68 | 61% |
| | * | HAND1 | 0% | 60% | 67 | 60% |
| | * | STOX2 | 0% | 59% | 64 | 59% |
| | * | THBD | 0% | 57% | 64 | 57% |
| | * | ELMO1 | 0% | 55% | 62 | 55% |
| | * | IGFBP7 | 0% | 52% | 58 | 52% |
| | * | PPP1R3C | 0% | 51% | 57 | 51% |
| | | AOX1 | 0% | 48% | 54 | 48% |
| | | CHFR | 0% | 38% | 43 | 38% |
| | | EFHD1 | 0% | 36% | 40 | 36% |
| | | DUSP26 | 0% | 36% | 40 | 36% |
| | | SLC30A10 | 0% | 24% | 27 | 24% |
| | | FLJ23191 | 0% | 22% | 24 | 22% |
| | | ID4 | 0% | 18% | 20 | 18% |
| | | EPHB1 | 0% | 15% | 17 | 15% |
| | | LOX | 0% | 14% | 16 | 14% |
| | | MYOCD | 0% | 14% | 16 | 14% |
| B | * | SFRP1 | 22% | 100% | 112 | 78% |
| | * | CDO1 | 11% | 88% | 98 | 77% |
| | * | FBN2 | 13% | 69% | 77 | 56% |
| | * | ZNF447 | 22% | 63% | 71 | 41% |
| | | PENK | 56% | 100% | 112 | 44% |
| | | KCNC2 | 56% | 91% | 100 | 35% |
| C | | TLE4 | 0% | 3% | 3 | 3% |
| | | PCSK6 | 100% | 98% | 108 | −2% |
| | | CLDN23 | 100% | 99% | 109 | −1% |
| | | ABTB2 | 0% | 1% | 1 | 1% |
| | | SCAM1 | 0% | 1% | 1 | 1% |
| | | SPON1 | 11% | 12% | 13 | 1% |
| | | KIAA0495 | 100% | 100% | 112 | 0% |
| | | IRF8F2 | 0% | 0% | 0 | 0% |
| | | SLC35B3 | 0% | 0% | 0 | 0% |

In Table 4, the 41 genes were classified into three groups A, B and C based on the calculated proportions of methylation-positive specimens. The group A is a group of genes having 0% of the proportion of methylation-positive specimens in the population of normal colonic mucosa specimens (Normal) and 10% or more of the proportion in the population of colorectal cancer specimens (CRC); the group B is a group of genes having more than 0% of the proportion in the population Normal and 30% or more of the difference in the proportions of methylation-positive specimens between CRC and Normal; and the group C is a group of genes having more than 0% of the proportion in the population Normal and less than 30% of the difference in the proportions of methylation-positive specimens between CRC and Normal.

Among 41 genes shown in Table 4, the genes having 50% or more of the difference in the proportions of methylation-positive specimens between CRC and Normal were selected as possible markers, which are marked with * in Table 4.

The selected genes are TSPYL, COL4A2, ADAMTS1, SPG20, TMEFF2, CIDEB, EDIL3, EFEMP1, PPP1R14A, UCHL1, HAND1, STOX2, THBD, ELMO1, IGFBP7, PPP1R3C, SFRP1, CDO1, FBN2 and ZNF447.

The proportion of methylation-positive specimens was also calculated for each gene when the cut-off value for determination of methylation was set at 10%. The results are shown in Table 5. Again, the genes having 50% or more of the difference in the proportions of methylation-positive specimens between CRC and Normal were selected, which are marked with * in Table 5. The definition for the groups A to C is the same as described above.

The selected genes are EFHD1, STOX2, ELMO1, CHFR, DUSP26, MYOCD, FLJ23191, LOX, EPHB1, TLE4, TMEFF2, SPG20, EDIL3, PPP1R3C, FBN2, AOX1 and ZNF447.

TABLE 5

| Group | | Gene symbol | Normal (n = 9) Proportion of methylation-positive specimens (%) | CRC (n = 112) Proportion of methylation-positive specimens (%) | Number of methylation-positive specimens | Difference in methylation frequency between CRC and Normal (%) |
|---|---|---|---|---|---|---|
| A | * | EFHD1 | 0% | 80% | 89 | 80% |
| | * | STOX2 | 0% | 80% | 86 | 80% |
| | * | ELMO1 | 0% | 68% | 76 | 68% |
| | * | CHFR | 0% | 62% | 69 | 62% |
| | * | DUSP26 | 0% | 59% | 65 | 59% |
| | * | MYOCD | 0% | 29% | 32 | 29% |
| | * | FLJ23191 | 0% | 27% | 30 | 27% |
| | * | LOX | 0% | 26% | 29 | 26% |
| | * | EPHB1 | 0% | 23% | 26 | 23% |
| | * | TLE4 | 0% | 10% | 11 | 10% |
| B | * | TMEFF2 | 11% | 99% | 110 | 88% |
| | * | SPG20 | 11% | 92% | 103 | 81% |
| | * | EDIL3 | 11% | 88% | 98 | 77% |
| | * | PPP1R3C | 11% | 80% | 89 | 69% |
| | * | FBN2 | 25% | 90% | 101 | 65% |
| | * | AOX1 | 11% | 68% | 76 | 57% |
| | * | ZNF447 | 22% | 78% | 87 | 56% |
| | | EFEMP1 | 44% | 92% | 103 | 48% |
| | | PPP1R14A | 50% | 87% | 97 | 37% |
| | | UCHL1 | 56% | 91% | 102 | 35% |
| | | THBD | 56% | 90% | 101 | 34% |
| | | CDO1 | 67% | 99% | 110 | 32% |
| | | COL4A2 | 67% | 99% | 111 | 32% |
| C | | CIDEB | 67% | 94% | 105 | 27% |
| | | SLC30A10 | 22% | 41% | 46 | 19% |
| | | ID4 | 63% | 48% | 54 | -15% |
| | | PENK | 89% | 100% | 112 | 11% |
| | | HAND1 | 78% | 89% | 99 | 11% |
| | | TSPYL | 89% | 99% | 110 | 10% |
| | | ADAMTS1 | 89% | 99% | 109 | 10% |
| | | SPON1 | 44% | 35% | 39 | -9% |
| | | IRF8F2 | 11% | 3% | 3 | -8% |
| | | ABTB2 | 0% | 4% | 4 | 4% |
| | | IGFBP7 | 89% | 92% | 102 | 3% |
| | | KCNC2 | 100% | 99% | 109 | -1% |
| | | SCAM1 | 0% | 1% | 1 | 1% |
| | | KIAA0495 | 100% | 100% | 112 | 0% |
| | | SFRP1 | 100% | 100% | 112 | 0% |
| | | PCSK6 | 100% | 100% | 110 | 0% |
| | | CLDN23 | 100% | 100% | 110 | 0% |
| | | SLC35B3 | 0% | 0% | 0 | 0% |

Thus, possible markers selected from these two cut-off values of methylation rate are ADAMTS1, AOX1, CDO1, CHFR, CIDEB, COL4A2, DUSP26, EDIL3, EFEMP1, EFHD1, ELMO1, EPHB1, FBN2, FLJ23191, HAND1, IGFBP7, LOX, MYOCD, PPP1R14A, PPP1R3C, SFRP1, STOX2, THBD, TLE4, TMEFF2, SPG20, TSPYL, UCHL1 and ZNF447.

Among those genes, the genes whose methylation in a certain cancer cells has already been reported are shown in the following Table 6.

TABLE 6

| Gene symbol | Related documents suggesting methylation of the gene in cancer | |
|---|---|---|
| | Carcinoma | Related documents |
| TSPYL | ① Glioma | ① Cancer Research vol. 66, 7490-7501 (2006) |
| | ② Gastric carcinoma | ② Laboratory Investigation vol. 88, 153-160 (2008) |
| ADAMTS1 | Colorectal cancer, lung cancer and ovarian cancer | Mol Cancer. vol. 7, 94 (2008) |
| TMEFF2 | Esophageal cancer | Oncology Reports, Vol. 21, 1067-1073 (2009) |
| CIDEB | Hepatocarcinoma, culture cells | Biochem. J. vol. 393, 779-788 (2006) |
| EFEMP1 | Breast carcinoma | International Journal of Cancer, Vol. 124, Issue 7, 1727-1735 (2009) |
| PPP1R14A | Colorectal cancer | US2008-221056 (Publication of US patent application) |
| UCHL1 | Pancreatic cancer, gastric carcinoma | International Journal of Cancer, Vol. 124, Issue 4, 827-833 (2009) |
| HAND1 | Gastric carcinoma | Cancer Epidemiology Biomarkers & Prevention Vol. 15, 2317-2321 (2006) |
| THBD | Gastric carcinoma | Clinical Cancer Research Vol. 12, 989-995 (2006) |
| IGFBP7 | Colorectal cancer | The Journal of Pathology, Vo. 212, Issue 1, 83-90 (2007) |
| PPP1R3C | Melanoma | Genes, Chromosomes and Cancer, Vol. 48, Issue 1, 10-21 (2009) |
| CHFR | Lung cancer | Anticancer Research vol. 29, 363-369 (2009) |
| SFRP1 | Colorectal cancer | Int J Biol Markers. Vol. 24, 57-62 (2009) |
| CDO1 | Lung cancer | US2007-264659 (Publication of US patent application) |
| FBN2 | Esophageal cancer, lung cancer | Oncology Reports, Volume 21, 1067-1073 (2009) |
| SPG20 | Colorectal cancer, prostate cancer | WO2008102002 (Intl. publication), WO2009065511 (Intl. publication) |

Thus, the present inventors excluded the genes shown in Table 6 and identified for the first time COL4A2, AOX1, DUSP26, EDIL3, EFHD1, ELMO1, STOX2 and ZNF447 as marker genes which can be used for determination of the presence or absence of cancer cells.

Example 3

Analysis of Correlation Between Methylation of Marker Genes and MSI

There are many published documents which report on the correlation between MSI and the prognosis of colorectal cancer patients. Generally, it is believed that the cases having high MSI correlate to a favorable prognosis. According to the report by Popat S. et al. (J Clin Oncol, Vol. 23, 609-613 (2005)) who summarized the previously reported data from 32 reports (total 7642 cases among which MSI cases were 1277), it has been understood that the colorectal cancer patients having high MSI have a statistically significant favorable prognosis.

Accordingly, the present inventors investigated a possible correlation between the proportion of methylation-positive specimens for a marker gene among the above 41 marker genes and MSI.

(1) Determination for MSI

In order to analyze MSI of genomic DNA of colorectal cancer tissues (112 specimens) obtained in Example 2 (1) (i), sequencing analysis was carried out for five MSI markers (BAT25, BAT26, D5S346, D2S123 and D17S250) recommended by the NCI Workshop described above.

The base sequences of these five markers in genomic DNA from each specimen were analyzed with ALF express DNA sequencer (Pharmacia Biotech) and Allele Links software (Pharmacia Biotech).

MSI-H was assigned to the specimens in which MSI was detected in two or more markers among five, MSI-L to the specimens in which MSI was detected in one marker and MSS to the specimens in which no MSI was detected in any marker. Analysis was repeated at least twice for the markers in which MSI was detected.

(2) Analysis on Correlation Between Methylation of Marker Genes and MSI

In order to analyze whether there is a correlation between the population in which a marker gene is methylation-positive and the population having MSI-H, Fisher's exact test was used.

As shown in below, the analysis showed that the population in which the marker genes ID4, LOX and MYOCD were methylated had a strong correlation with the population of MSI-H. P is the significance probability calculated from the above test. The results are shown in Table 7.

TABLE 7

|  |  | Methylated | Non-methylated |  |
|---|---|---|---|---|
| ID4 | MSI-H | 15 | 3 | Fisher's exact test |
|  | Other than MSI-H | 5 | 89 | $P = 6.9 \times 10^{-12}$ |
| LOX | MSI-H | 15 | 3 | Fisher's exact test |
|  | Other than MSI-H | 1 | 93 | $P = 8.1 \times 10^{-15}$ |
| MYOCD | MSI-H | 14 | 4 | Fisher's exact test |
|  | Other than MSI-H | 2 | 92 | $P = 1.4 \times 10^{-12}$ |

Numbers in the tables correspond to the number of specimens.

For ID4, among 20 methylated specimens, 15 were MSI-H and among 92 non-methylated specimens, 3 were MSI-H ($P=6.9\times10^{-12}$).

For LOX, among 16 methylated specimens, 15 were MSI-H and among 96 non-methylated specimens, 3 were MSI-H ($P=8.1\times10^{-15}$).

For MYOCD, among 16 methylated specimens, 14 were MSI-H and among 96 non-methylated specimens, 4 were MSI-H ($P=1.4\times10^{-12}$).

From the above results, it is suggested that the colorectal cancer patients in which any one of ID4, LOX and MYOCD is methylated may tend to be high in MSI, namely have a favorable prognosis. Thus, it is expected that the prognosis of colorectal cancer patients may be predicted by analyzing methylation status of these three marker genes.

Example 4

Detection of Colorectal Cancer Cells by Methylation Specific PCR (MSP)

(1) Preparation of Specimen Samples

As described below, a HCT116 sample, a DLD-1 sample, CRC specimen samples 1 to 7 and a Normal specimen sample were prepared from genomic DNAs derived from colorectal cancer cell lines HCT116 and DLD-1, colorectal cancer tissues 1 to 7 taken from colorectal cancer patients, and normal colonic mucosa tissue, respectively.

(i) Extraction of DNA from Colorectal Cancer Cell Lines, Colorectal Cancer Tissues and Normal Colonic Mucosa Tissue DNAs were extracted from each of HCT116, DLD-1, colorectal cancer tissues 1 to 7 and a normal colonic mucosa tissue by using QIAAMP® DNA Micro kit (QIAGEN) according to the attached instruction. Genomic DNAs extracted from colorectal cancer cell lines, colorectal cancer tissues and the normal colonic mucosa tissue were cleaved by ultrasonication in Bioruptor (COSMO BIO Co., Ltd.).

(ii) Bisulfite Treatment

The DNAs (1 µg) obtained in the above (i) were diluted in 19 µl water, 1 µl of a 6N aqueous solution of sodium hydroxide was added to the final concentration of 0.3 N and the mixture was incubated at 37° C. for 15 minutes in order to denature DNA. To the above DNA solutions was added 120 µl of a 3.6 M sodium bisulfite/0.6 M hydroquinone solution, and the mixtures were subjected to bisulfite treatment by performing 15 cycles of 95° C. for 30 seconds and 50° C. for 15 minutes. The reaction solutions were subjected to desalting on Wizard® DNA Clean-up System (Promega) and eluted with 50 µl of TE buffer to obtain the solutions of DNA in which non-methylated cytosine(s) was (were) converted to uracil(s).

To the DNA solutions was added 5 µl of a 3 N aqueous solution of sodium hydroxide, and the mixture was incubated at room temperature for 5 minutes before DNA purification by ethanol precipitation. Finally, DNAs were dissolved in 80 µl water to obtain the HCT116 sample, the DLD-1 sample, CRC specimen samples 1 to 7 and the Normal specimen sample.

(2) Preparation of Control Samples (i) Preparation of 0% and 100% Methylated DNAs Human peripheral blood lymphocyte genomic DNA was amplified by using GENOMIPHI® v2 DNA amplification kit (GE Healthcare Life Science). The amplified product is non-methylated DNA. The amplified product was then cleaved by ultrasonication in Bioruptor (COSMO BIO Co., Ltd.) to obtain DNA fragments (0% methylated DNA). A portion of the DNA fragments was reacted with SssI methylase (New England Biolab) and all cytosines were methylated to obtain methylated DNA fragments (100% methylated DNA).

(ii) Bisulfite Treatment

In the same manner as the bisulfite treatment for preparation of specimen samples described above, 0% methylated DNA and 100% methylated DNA were treated to obtain 0% methylated control sample and 100% methylated control sample.

(3) Methylation Specific PCR (MSP)

The specimen samples and control samples obtained as described in the above (1) and (2) (DNAs after bisulfite treatment) were used for MSP. Composition of a PCR reagent, primer sets and PCR conditions are shown below.

<PCR Reagent>

| | |
|---|---|
| DDW (Sterilized water) | 15.25 μl |
| 10 × PCR buffer with MgCl$_2$ (Roche) | 2.5 μl |
| 1.25 mM dNTP mix | 4 μl |
| 10 μM sense primer | 1 μl |
| 10 μM antisense primer | 1 μl |
| Faststart Taq polymerase (Roche) | 0.25 μl |
| Specimen sample | 1 μl |
| Total | 25 μl |

<Primer Sets>

Primer sets used in MSP are shown in Table 8. In the third column of Table 3, "M" denotes primers for detection of methylation and "U" denotes primers for detection of non-methylation.

TABLE 8

| Gene No. | symbol | Primer | SEQ ID NO: | Base sequence of primer | Size of PCR product (bp) | Annealing temperature (X °C.) | No. of cycles (Y) |
|---|---|---|---|---|---|---|---|
| 1 | COL4A2 | M COL4A2_MF | 95 | GGTTCGTTTATTTTGGGTTTC | 162 bp | 64° C. | 34 |
| | | COL4A2_MR | 96 | TCCGATCACCCCTACATACG | | | |
| | | U COL4A2_UF | 97 | GAGGGAGGTAGTTTATTTTTATTGTT | 173 bp | 62° C. | 34 |
| | | COL4A2_UR | 98 | AAAAACCAAACTCCTCAACCA | | | |
| 2 | AOX1 | M AOX1_MF | 99 | AAGGGGTCGTTTTTATTTTCGTC | 88 bp | 63° C. | 34 |
| | | AOX1_MR | 100 | TCTTCCCGAAACACCAACACG | | | |
| | | U AOX1_UF | 101 | AAGAGGGTGTGATATAGATGTTAAGT | 131 bp | 61° C. | 36 |
| | | AOX1_UR | 102 | CTTCCCAAAACACCAACACA | | | |
| 3 | DUSP26 | M DUSP26_MF | 103 | TCGTGTTTGGTTTGTAAGGC | 90 bp | 63° C. | 34 |
| | | DUSP26_MR | 104 | GATCTCACATTCGATAACCCG | | | |
| | | U DUSP26_UF | 105 | TGTGTTTGGTTTGTAAGGTGTGT | 135 bp | 58° C. | 34 |
| | | DUSP26_UR | 106 | AAACAAAATTCAAATCAACATATACA | | | |
| 4 | ELMO1 | M ELMO1_MF | 107 | TGAGAGTAGCGGTAGTCGGC | 150 bp | 63° C. | 34 |
| | | ELMO1_MR | 108 | AAAAACTCTATCGCCCAACG | | | |
| | | U ELMO1_UF | 109 | AGAGGAAGTGAGAGTAGTGGTAGTT | 144 bp | 63° C. | 34 |
| | | ELMO1_UR | 110 | CCAACATAAAACCACAACAACA | | | |
| 5 | STOX2 | M STOX2_MF | 111 | TGAGAAGTTTGATGGGAATCGC | 128 bp | 62° C. | 34 |
| | | STOX2_MR | 112 | ACGACAACGCTACTCCGACG | | | |
| | | U STOX2_UF | 113 | TGAGAAGTTTGATGGGAATTGT | 115 bp | 61° C. | 34 |
| | | STOX2_UR | 114 | TCCAACACAAACACACAAAACA | | | |
| 6 | EDIL3 | M EDIL3_MF | 115 | GTTATTTCGGTTATATTGTTTTTCGC | 106 bp | 62° C. | 34 |
| | | EDIL3_MR | 116 | ACCCGACCAAAAACCAAACG | | | |
| | | U EDIL3_UF | 117 | TGTTGTTGTTTTGTGTTGTTATTTT | 89 bp | 62° C. | 36 |
| | | EDIL3_UR | 118 | CATAATCCCATCTCCCAAACA | | | |
| 7 | ZN F447 | M ZNF447_MF | 119 | TTCGTTGTTATGGTGTTTAAAATGAC | 161 bp | 63° C. | 36 |
| | | ZNF447_MR | 120 | GAACTACGACTCCCACAATACCG | | | |
| | | U ZNF447_UF | 121 | GGATGTTGGGAGGTTATATTTGT | 139 bp | 62° C. | 34 |
| | | ZNF447_UR | 122 | ACCTACACACTAAACCTCACCACA | | | |
| 8 | EFHD 1 | M EFHD1_MF | 123 | TGTTGTAGAGTTTCGAGTTTGC | 111 bp | 60° C. | 34 |
| | | EFHD1_MR | 124 | TCCTCACTAACCATAACGACG | | | |
| | | U EFHD1_UF | 125 | GAGTGTGTTGTTTGTTAGTTTTTTGT | 128 bp | 60° C. | 34 |
| | | EFHD1_UR | 126 | ACCTCCTCACACCACAACCA | | | |

<PCR Reaction Conditions>
95° C. for 6 minutes;
Y cycles of 95° C. for 30 seconds, X° C. for 30 seconds and 72° C. for 30 seconds;
72° C. for 7 minutes; and
leave at 16° C.

In the above conditions, "X" and "Y" denote the annealing temperature and the number of cycles, respectively, specified in Table 8.

(3) Analysis of Methylation Specific PCR (MSP) Results

Amplification products obtained by the above MSP were verified on 2% agarose gel electrophoresis. The images obtained by the agarose gel electrophoresis were analyzed with an image processing software (ImageJ) to determine the intensity of the bands. The intensity of each band was calculated by subtracting from the intensity of the band in question the intensity of the background in the same lane. The followings describe the symbols used in the figures showing the results of agarose gel electrophoresis and the figures of the graphs of band intensities as described below.

M: Primers for detection of methylation
U: Primers for detection of non-methylation
0%: 0% methylation control sample
100%: 100% methylation control sample
HCT116: HCT116 sample
DLD1: DLD-1 sample
N: Normal specimen sample
1: CRC specimen sample 1
2: CRC specimen sample 2
3: CRC specimen sample 3
4: CRC specimen sample 4
5: CRC specimen sample 5
6: CRC specimen sample 6
7: CRC specimen sample 7

<COL4A2>

Figure 2:
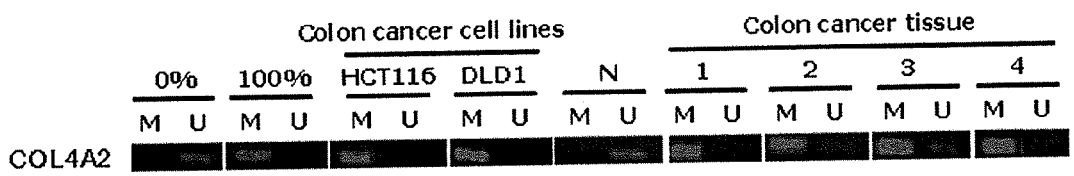
FIG. 2 is a representation showing results of agarose gel electrophoresis after methylation specific PCR (MSP) using the primer set for COL4A2 in Example 4.
Figure 3:
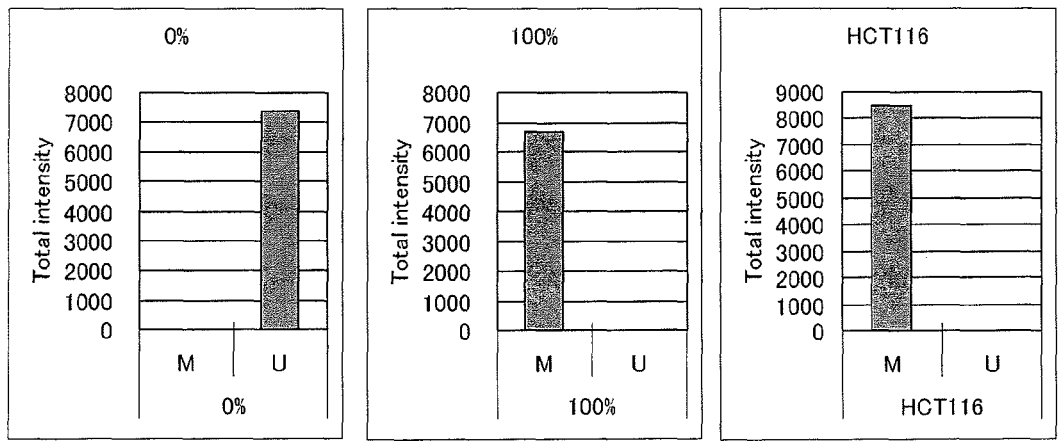
FIG. 3 is graphs showing band intensities of agarose gel electrophoresis after MSP using the primer set for COL4A2 in Example 4.
Figure 3:
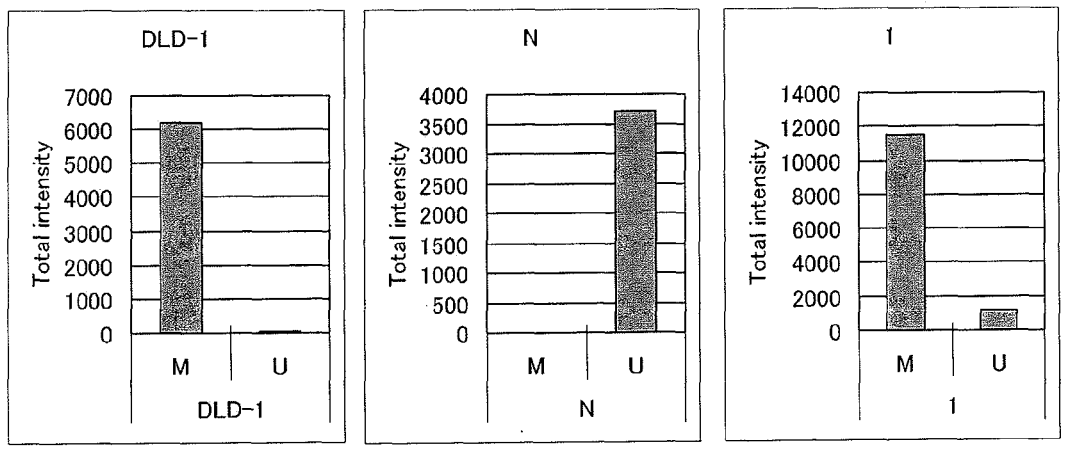
Figure 3:
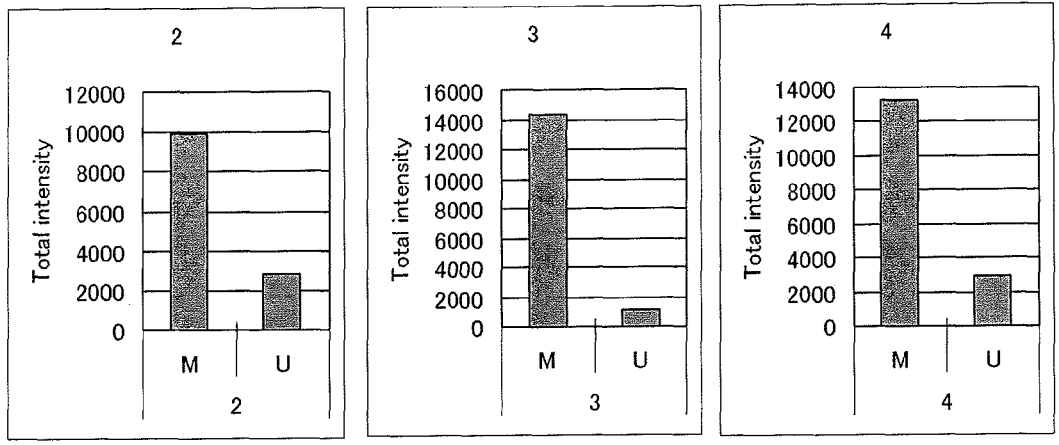

FIG. 2 shows the results of agarose gel electrophoresis of MSP using the primer set for COL4A2. FIG. 3 shows the graphs of band intensities of agarose gel electrophoresis of methylation specific PCR using the primer set for COL4A2.

FIGS. 2 and 3 show that 100% methylation control sample, HCT116 sample, DLD-1 sample, CRC specimen samples 1 to 4 resulted in stronger band intensities in PCR when the primers for detection of methylation were used than the primers for detection of non-methylation were used, while 0% methylation control sample and Normal specimen sample resulted in stronger band intensities in PCR when the primers for detection of non-methylation were used than the primers for detection of methylation were used. These results revealed that colorectal cancer cells can be detected by analyzing methylation status of COL4A2 gene in biological samples by MSP.

<AOX1>

Figure 4:
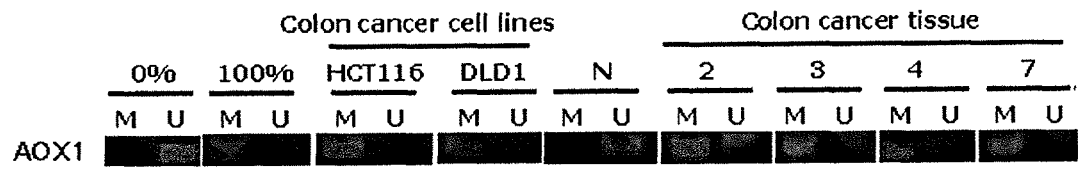
FIG. 4 is a representation showing results of agarose gel electrophoresis after MSP using the primer set for AOX1 in Example 4.
Figure 5:
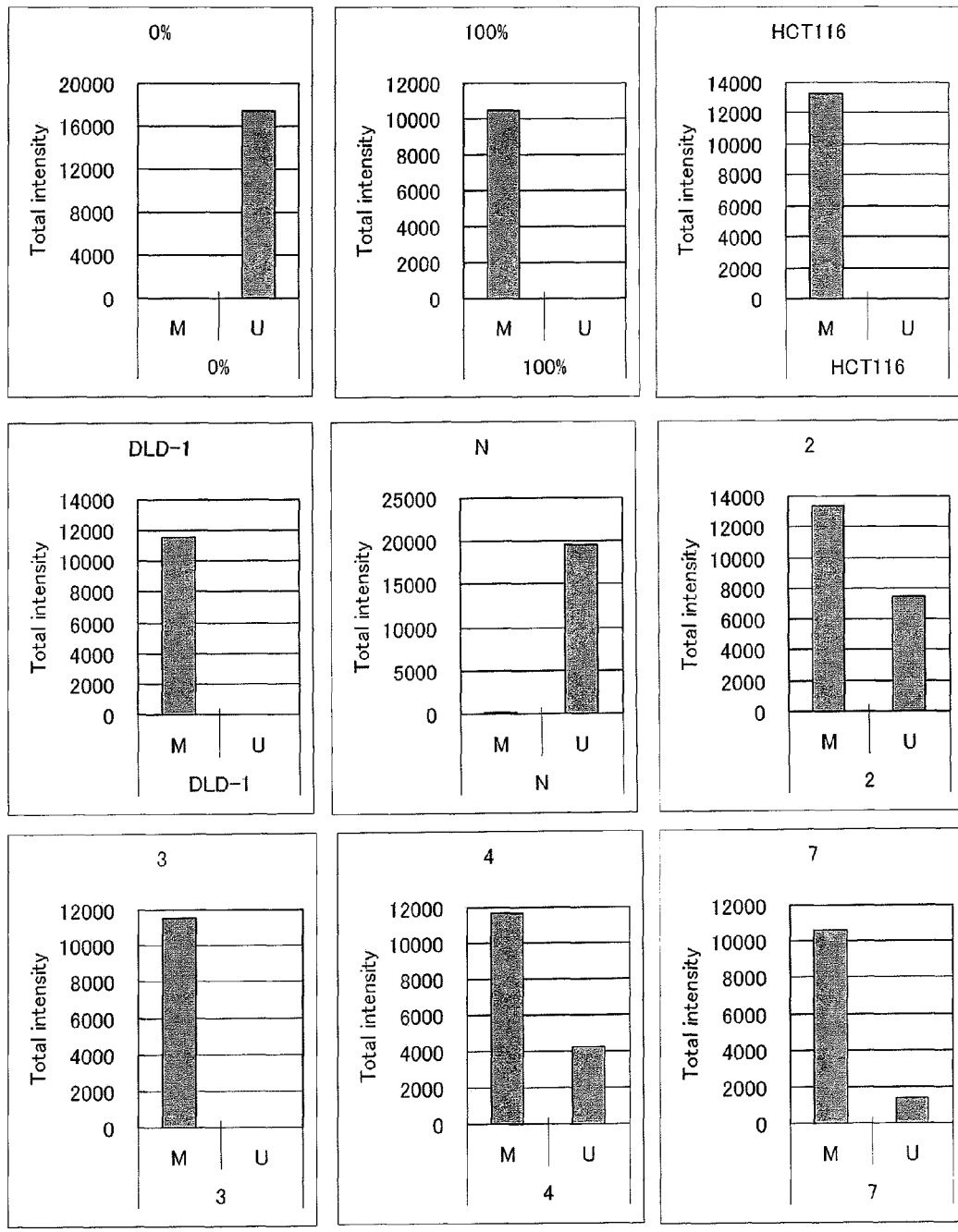
FIG. 5 is graphs showing band intensities of agarose gel electrophoresis after MSP using the primer set for AOX1 in Example 4.

FIG. 4 shows the results of agarose gel electrophoresis of MSP using the primer set for AOX1. FIG. 5 shows the graphs of band intensities of agarose gel electrophoresis of methylation specific PCR using the primer set for AOX1.

FIGS. 4 and 5 show that 100% methylation control sample, HCT116 sample, DLD-1 sample, and CRC specimen samples 2 to 4 and 7 resulted in stronger band intensities in PCR when the primers for detection of methylation were used than the primers for detection of non-methylation were used, while 0% methylation control sample and Normal specimen sample resulted in stronger band intensities in PCR when the primers for detection of non-methylation were used than the primers for detection of methylation were used. These results revealed that colorectal cancer cells can be detected by analyzing methylation status of AOX1 gene in biological samples by MSP.

<DUSP26>

Figure 6:
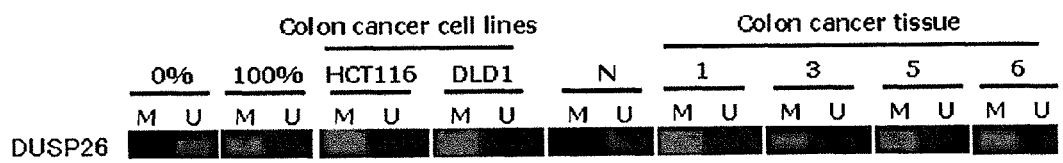
FIG. 6 is a representation showing results of agarose gel electrophoresis after MSP using the primer set for DUSP26 in Example 4.
Figure 7:
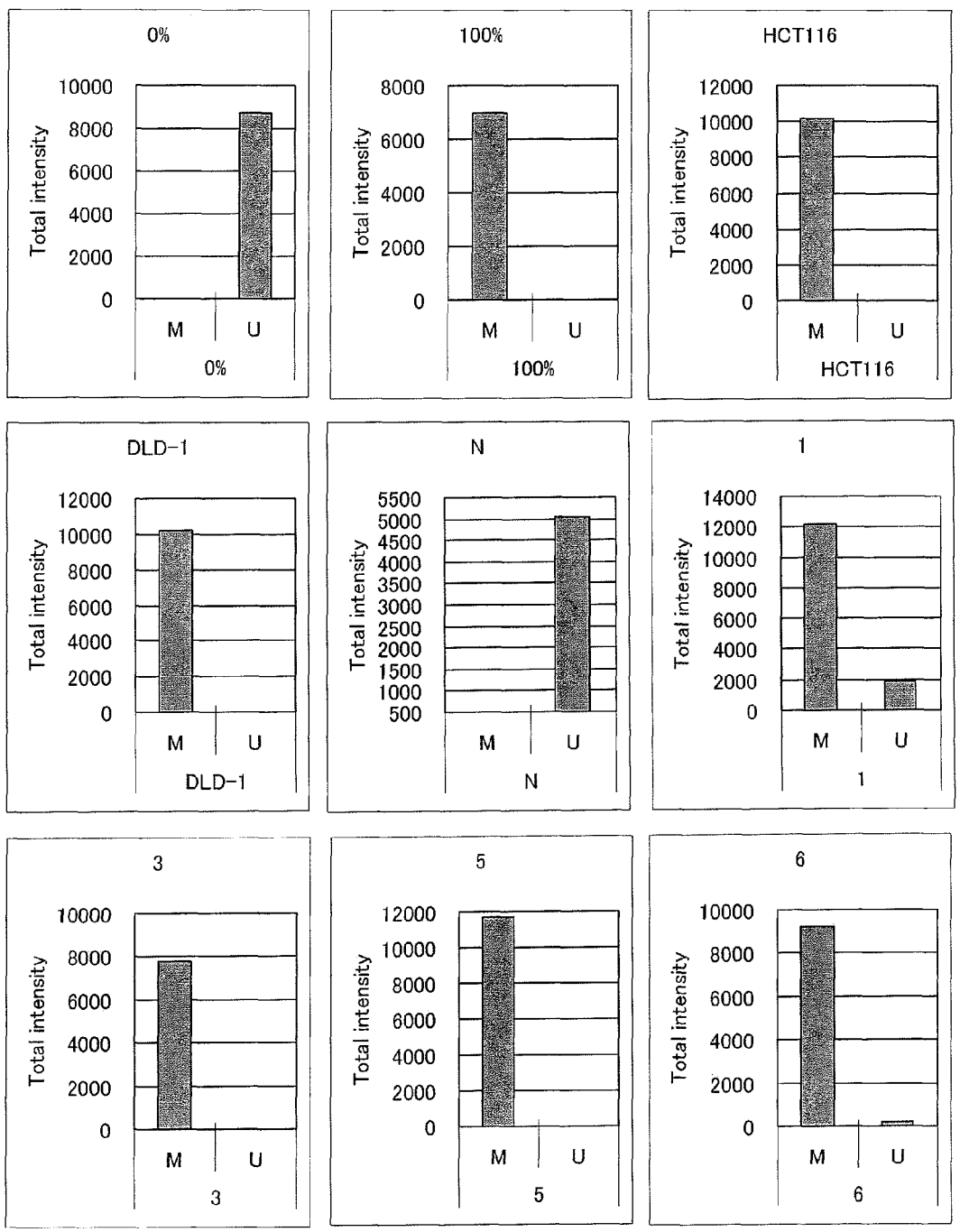
FIG. 7 is graphs showing band intensities of agarose gel electrophoresis after MSP using the primer set for DUSP26 in Example 4.

FIG. 6 shows the results of agarose gel electrophoresis of MSP using the primer set for DUSP26. FIG. 7 shows the graphs of band intensities of agarose gel electrophoresis of methylation specific PCR using the primer set for DUSP26.

FIGS. 6 and 7 show that 100% methylation control sample, HCT116 sample, DLD-1 sample, and CRC specimen samples 1, 3, 5 and 6 resulted in stronger band intensities in PCR when the primers for detection of methylation were used than the primers for detection of non-methylation were used, while 0% methylation control sample and Normal specimen sample resulted in stronger band intensities in PCR when the primers for detection of non-methylation were used than the primers for detection of methylation were used. These results revealed that colorectal cancer cells can be detected by analyzing methylation status of DUSP26 gene in biological samples by MSP.

<ELMO1>

Figure 8:
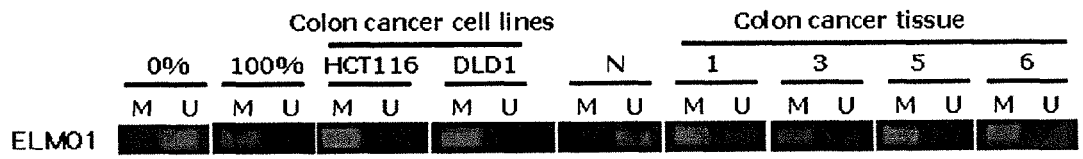
FIG. 8 is a representation showing results of agarose gel electrophoresis after MSP using the primer set for ELMO1 in Example 4.
Figure 9:
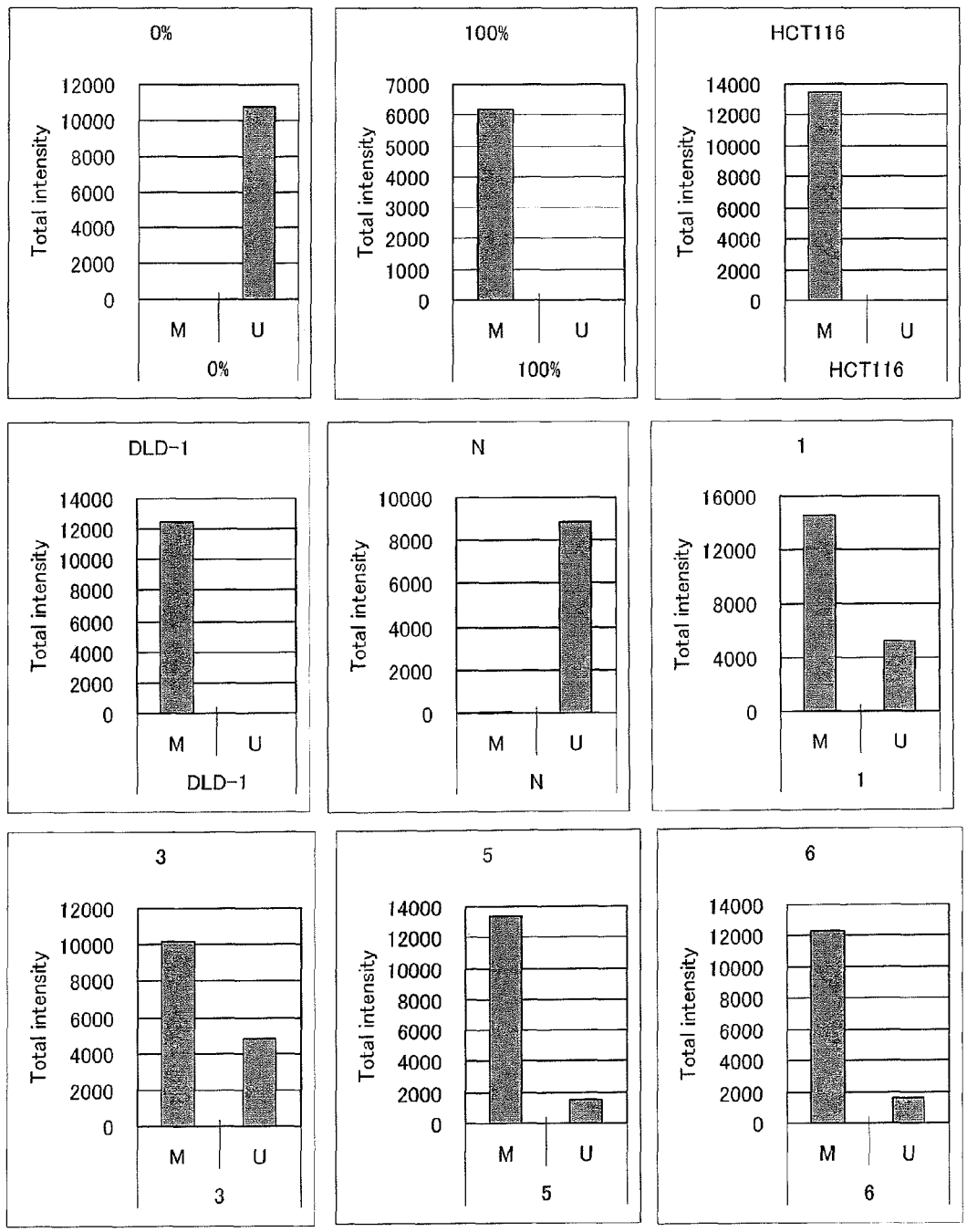
FIG. 9 is graphs showing band intensities of agarose gel electrophoresis after MSP using the primer set for ELMO1 in Example 4.

FIG. 8 shows the results of agarose gel electrophoresis of MSP using the primer set for ELMO1. FIG. 9 shows the graphs of band intensities of agarose gel electrophoresis of methylation specific PCR using the primer set for ELMO1.

FIGS. 8 and 9 show that 100% methylation control sample, HCT116 sample, DLD-1 sample, and CRC specimen samples 1, 3, 5 and 6 resulted in stronger band intensities in PCR when the primers for detection of methylation were used than the primers for detection of non-methylation were used, while 0% methylation control sample and Normal specimen sample resulted in stronger band intensities in PCR when the primers for detection of non-methylation were used than the primers for detection of methylation were used. These results revealed that colorectal cancer cells can be detected by analyzing methylation status of ELMO1 gene in biological samples by MSP.

<STOX2>

Figure 10:
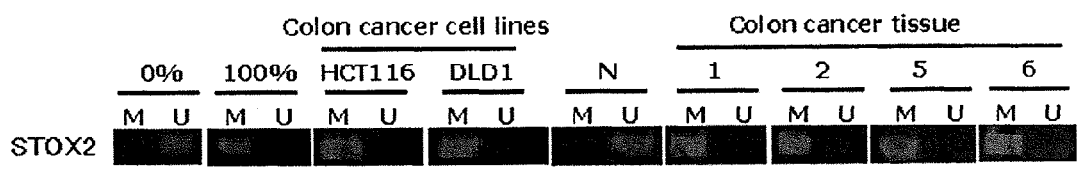
FIG. 10 is a representation showing results of agarose gel electrophoresis after MSP using the primer set for STOX2 in Example 4.
Figure 11:
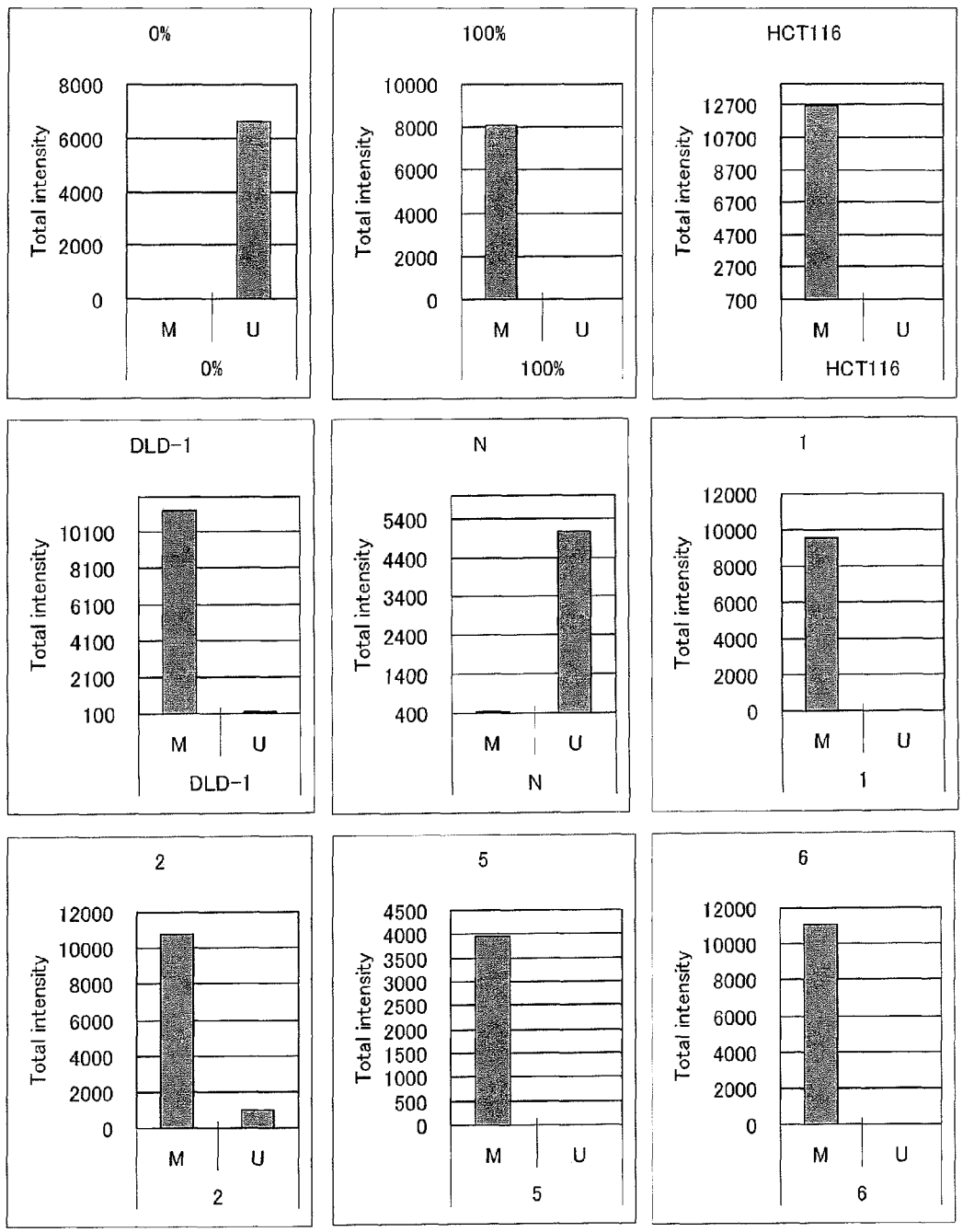
FIG. 11 is graphs showing band intensities of agarose gel electrophoresis after MSP using the primer set for STOX2 in Example 4.

FIG. 10 shows the results of agarose gel electrophoresis of MSP using the primer set for STOX2. FIG. 11 shows the graphs of band intensities of agarose gel electrophoresis of methylation specific PCR using the primer set for STOX2.

FIGS. 10 and 11 show that 100% methylation control sample, HCT116 sample, DLD-1 sample, and CRC specimen samples 1, 2, 5 and 6 resulted in stronger band intensities in PCR when the primers for detection of methylation were used than the primers for detection of non-methylation were used, while 0% methylation control sample and Normal specimen sample resulted in stronger band intensities in PCR when the primers for detection of non-methylation were used than the primers for detection of methylation were used. These results revealed that colorectal cancer cells can be detected by analyzing methylation status of STOX2 gene in biological samples by MSP.

<EDIL3>

Figure 12:
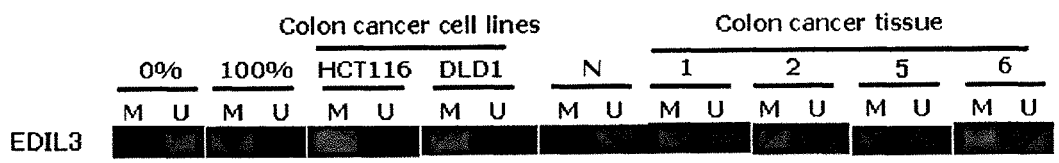
FIG. 12 is a representation showing results of agarose gel electrophoresis after MSP using the primer set for EDIL3 in Example 4.
Figure 13:
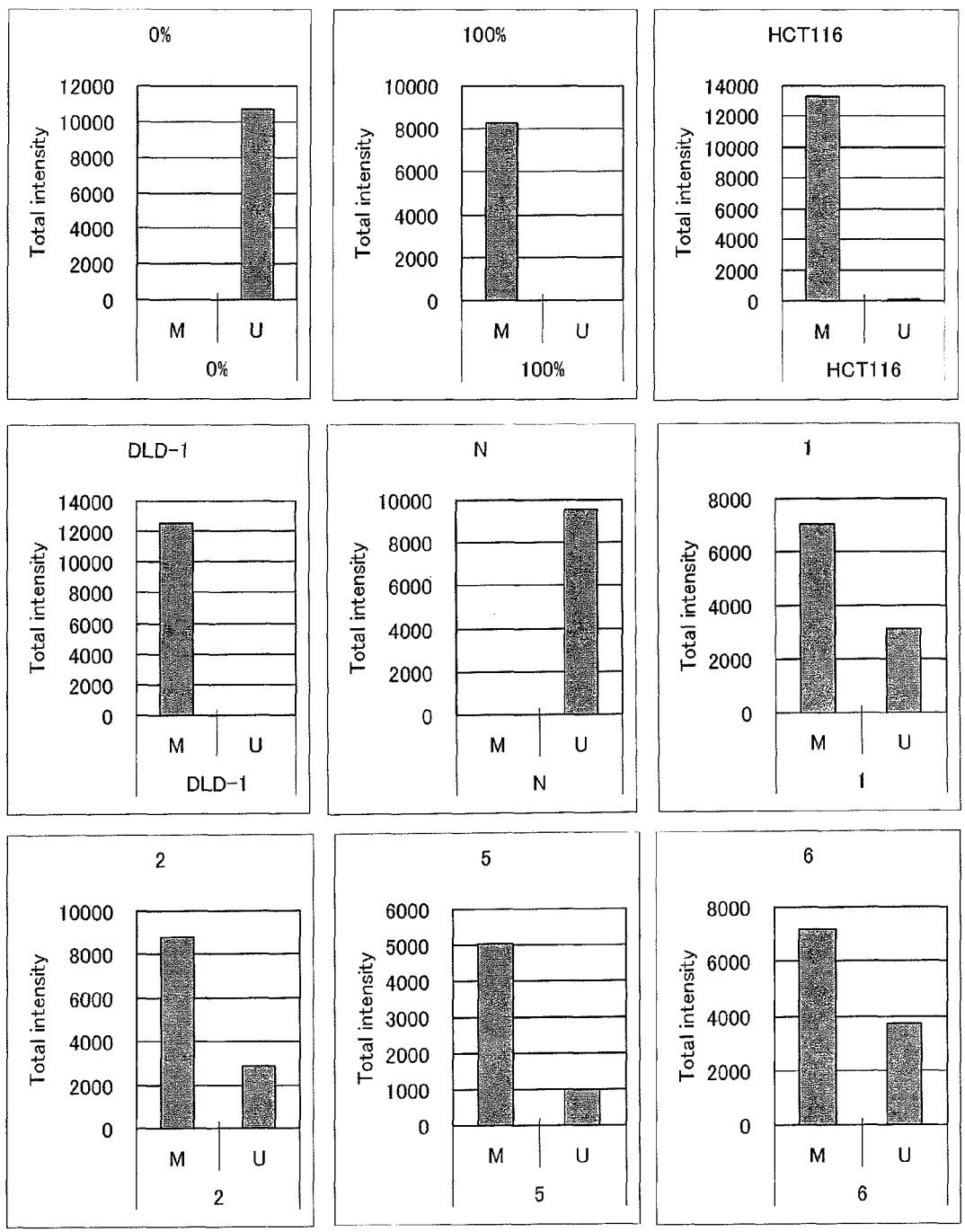
FIG. 13 is graphs showing band intensities of agarose gel electrophoresis after MSP using the primer set for EDIL3 in Example 4.

FIG. 12 shows the results of agarose gel electrophoresis of MSP using the primer set for EDIL3. FIG. 13 shows the graphs of band intensities of agarose gel electrophoresis of methylation specific PCR using the primer set for EDIL3.

FIGS. 12 and 13 show that 100% methylation control sample, HCT116 sample, DLD-1 sample, and CRC specimen samples 1, 2, 5 and 6 resulted in stronger band intensities in PCR when the primers for detection of methylation were used than the primers for detection of non-methylation were used, while 0% methylation control sample and Normal specimen sample resulted in stronger band intensities in PCR when the primers for detection of non-methylation were used than the primers for detection of methylation were used. These results revealed that colorectal cancer cells can be detected by analyzing methylation status of EDIL3 gene in biological samples by MSP.

<ZNF447>

Figure 14:
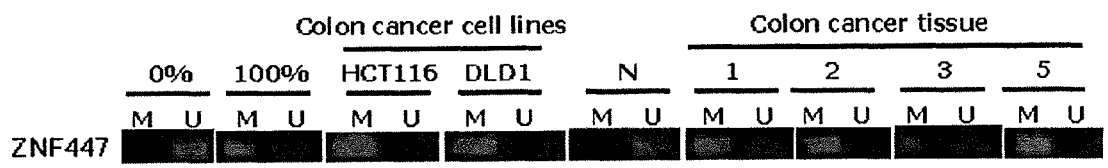
FIG. 14 is a representation showing results of agarose gel electrophoresis after MSP using the primer set for ZNF447 in Example 4.
Figure 15:
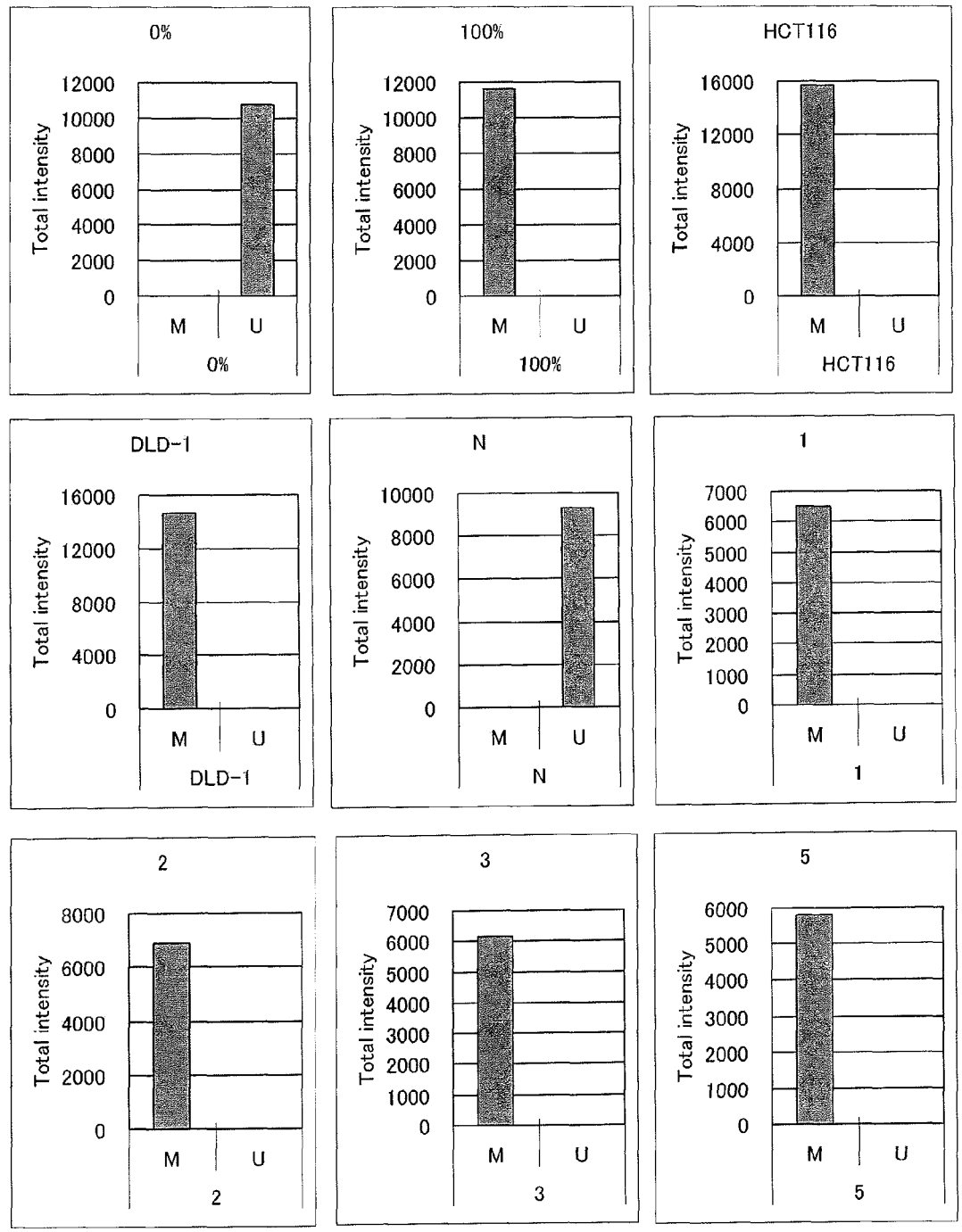
FIG. 15 is graphs showing band intensities of agarose gel electrophoresis after MSP using the primer set for ZNF447 in Example 4.

FIG. 14 shows the results of agarose gel electrophoresis of MSP using the primer set for ZNF447. FIG. 15 shows the graphs of band intensities of agarose gel electrophoresis of methylation specific PCR using the primer set for ZNF447.

FIGS. 14 and 15 show that 100% methylation control sample, HCT116 sample, DLD-1 sample, and CRC specimen samples 1, 2, 3 and 5 resulted in stronger band intensities in PCR when the primers for detection of methylation were used than the primers for detection of non-methylation were used, while 0% methylation control sample and Normal specimen sample resulted in stronger band intensities in PCR when the primers for detection of non-methylation were used than the primers for detection of methylation were used. These results revealed that colorectal cancer cells can be detected by analyzing methylation status of ZNF447 gene in biological samples by MSP.

<EFHD1>

Figure 16:
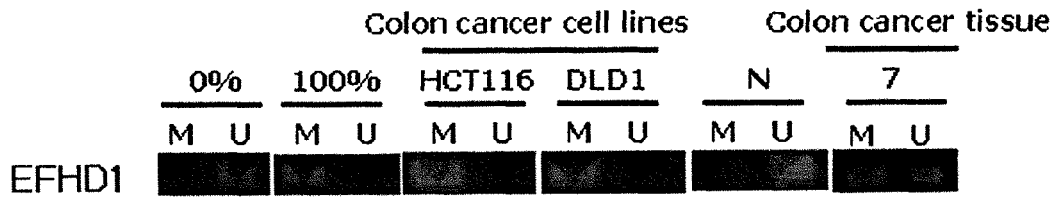
FIG. 16 is a representation showing results of agarose gel electrophoresis after MSP using the primer set for EFHD1 in Example 4.
Figure 17:
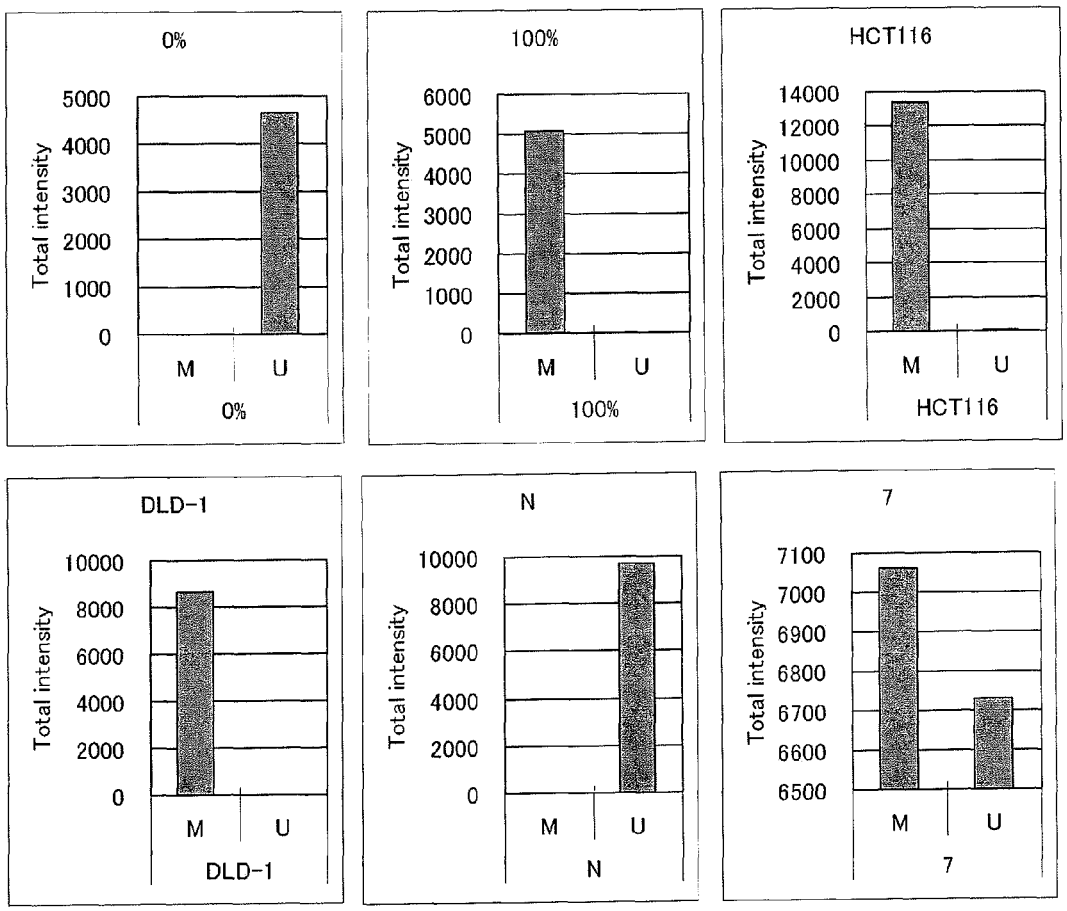
FIG. 17 is graphs showing band intensities of agarose gel electrophoresis after MSP using the primer set for EFHD1 in Example 4.

FIG. 16 shows the results of agarose gel electrophoresis of MSP using the primer set for EFHD1. FIG. 17 shows the graphs of band intensities of agarose gel electrophoresis of methylation specific PCR using the primer set for EFHD1.

FIGS. 16 and 17 show that 100% methylation control sample, HCT116 sample, DLD-1 sample and CRC specimen sample 7 resulted in stronger band intensities in PCR when the primers for detection of methylation were used than the primers for detection of non-methylation were used, while 0% methylation control sample and Normal specimen sample resulted in stronger band intensities in PCR when the primers for detection of non-methylation were used than the primers for detection of methylation were used. These results revealed that colorectal cancer cells can be detected by analyzing methylation status of EFHD1 gene in biological samples by MSP.

Example 5

Detection of Breast Cancer Cells by Methylation Specific PCR (MSP)

(1) Preparation of Specimen Samples

Two kinds of commercially available genomic DNAs derived from human normal mammary epithelial tissues were subjected to ultrasonication in Bioruptor (COSMO BIO Co., Ltd.). The ultrasonicated genomic DNAs derived from human normal mammary epithelial tissues were subjected to the bisulfite treatment in the similar manner as described in Example 4 to prepare normal mammary epithelial tissue specimen samples A and B. A commercially available genomic DNA derived from human breast cancer tissue was treated in the same manner to prepare a breast cancer specimen sample C.

(2) Preparation of Control Samples

In the similar manner of the preparation of control samples described in Example 4, 0% methylation control sample and 100% methylation control sample were prepared.

(3) Methylation Specific PCR (MSP)

The specimen samples and control samples obtained as described in the above (1) and (2) were used for MSP. Composition of a PCR reagent and PCR conditions for MSP are the same as those described in Example 4. The primers for COL4A2, AOX1 and STOX2 shown in Table 8 were used as primers.

(4) Analysis of Methylation Specific PCR (MSP) Results

As described in Example 4, amplified products were analyzed by using agarose gel electrophoresis and intensities of bands. The followings describe the symbols used in the figures showing the results of agarose gel electrophoresis and the figures of the graphs of band intensities as described below.

M: Primer for detection of methylation
U: Primer for detection of non-methylation
0%: 0% methylation control sample
100%: 100% methylation control sample
A: Normal mammary epithelial tissue specimen sample A
B: Normal mammary epithelial tissue specimen sample B
C: Breast cancer specimen sample C

<COL4A2>

Figure 18:
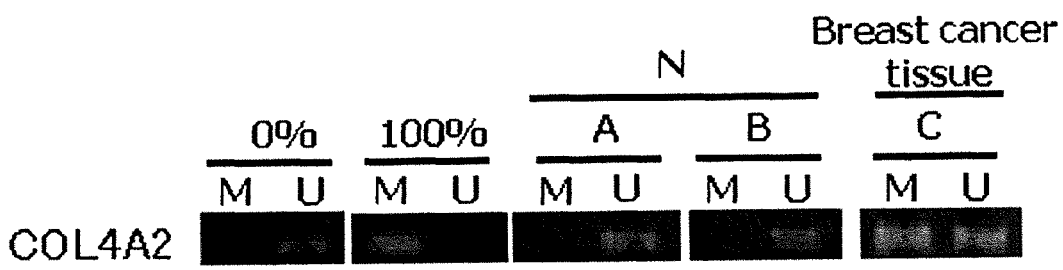
FIG. 18 is a representation showing results of agarose gel electrophoresis after MSP using the primer set for COL4A2 in Example 5.
Figure 19:
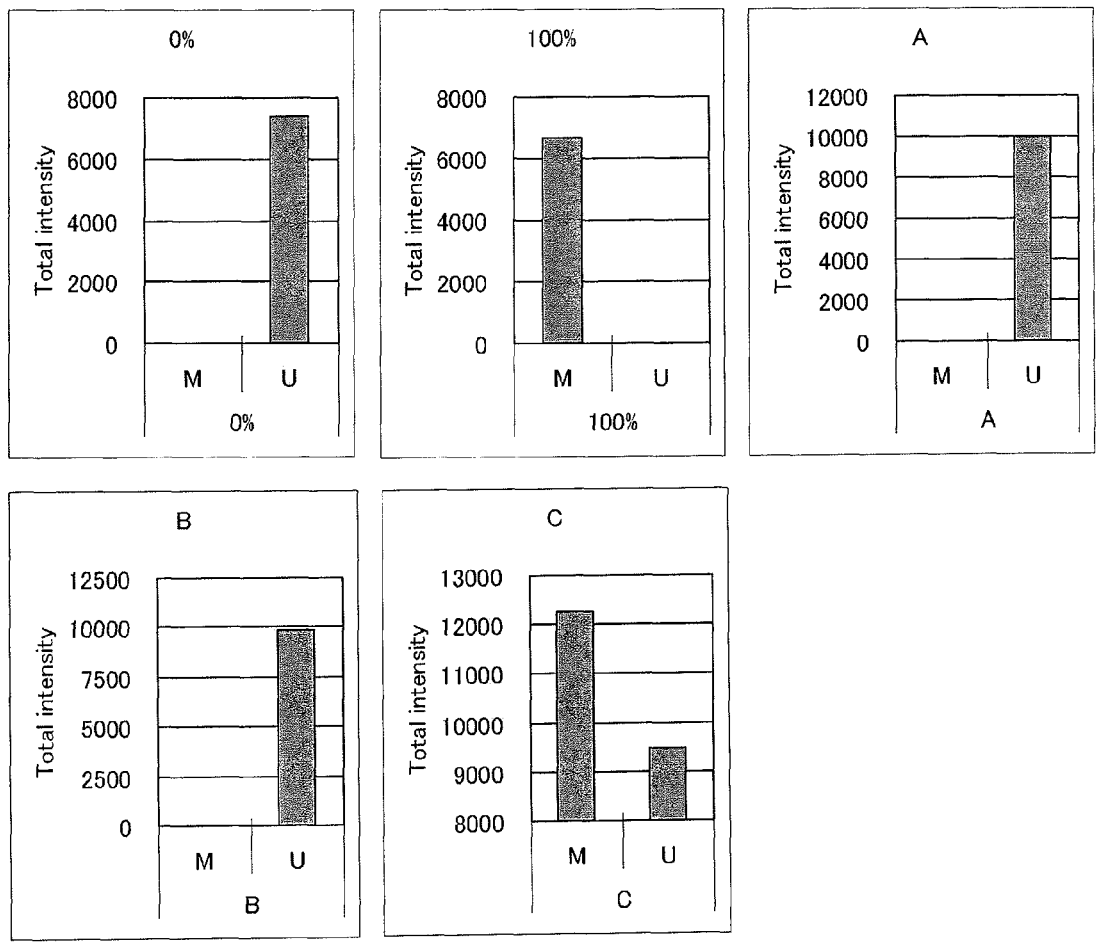
FIG. 19 is graphs showing band intensities of agarose gel electrophoresis after MSP using the primer set for COL4A2 in Example 5.

FIG. 18 shows the results of agarose gel electrophoresis of MSP using the primer set for COL4A2. FIG. 19 shows the graphs of band intensities of agarose gel electrophoresis of methylation specific PCR using the primer set for COL4A2.

FIGS. 18 and 19 show that 100% methylation control sample and breast cancer specimen sample C resulted in stronger band intensities in PCR when the primers for detection of methylation were used than the primers for detection of non-methylation were used, while 0% methylation control sample, and normal mammary epithelial tissue specimen samples A and B resulted in stronger band intensities in PCR when the primers for detection of non-methylation were used than the primers for detection of methylation were used. These results revealed that breast cancer cells can be detected by analyzing methylation status of COL4A2 gene in biological samples by MSP.

<AOX1>

Figure 20:
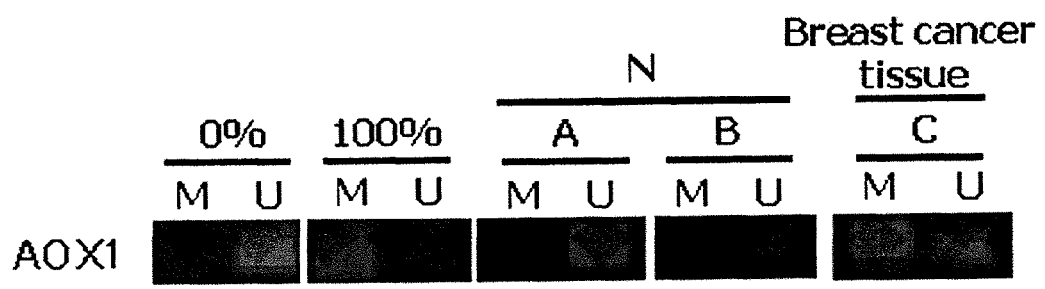
FIG. 20 is a representation showing results of agarose gel electrophoresis after MSP using the primer set for AOX1 in Example 5.
Figure 21:
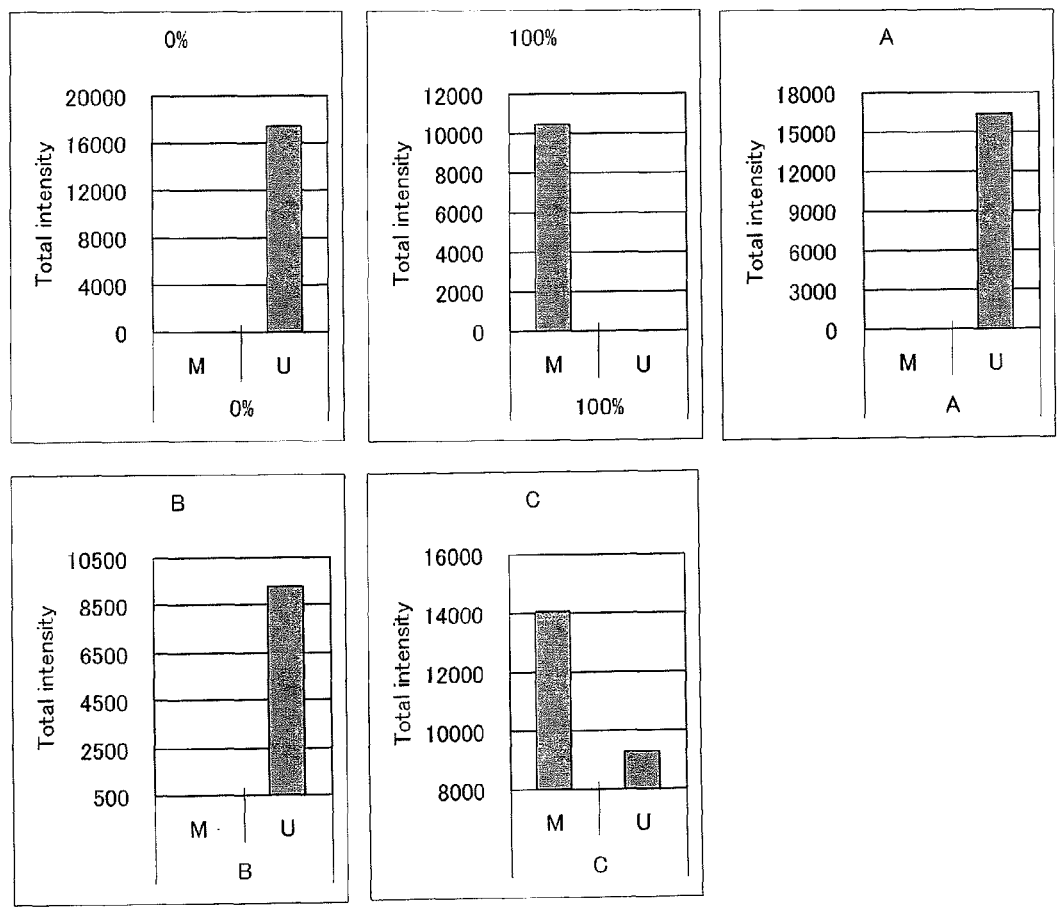
FIG. 21 is graphs showing band intensities of agarose gel electrophoresis after MSP using the primer set for AOX1 in Example 5.

FIG. 20 shows the results of agarose gel electrophoresis of MSP using the primer set for AOX1. FIG. 21 shows the graphs of band intensities of agarose gel electrophoresis of methylation specific PCR using the primer set for AOX1.

FIGS. 20 and 21 show that 100% methylation control sample and breast cancer specimen sample C resulted in stronger band intensities in PCR when the primers for detection of methylation were used than the primers for detection of non-methylation were used, while 0% methylation control sample, and normal mammary epithelial tissue specimen samples A and B resulted in stronger band intensities in PCR when the primers for detection of non-methylation were used than the primers for detection of methylation were used. These results revealed that breast cancer cells can be detected by analyzing methylation status of AOX1 gene in biological samples by MSP.

<STOX2>

Figure 22:
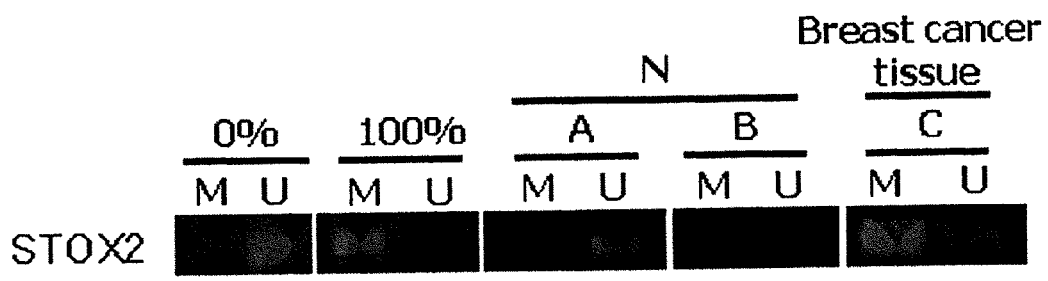
FIG. 22 is a representation showing results of agarose gel electrophoresis after MSP using the primer set for STOX2 in Example 5.
Figure 23:
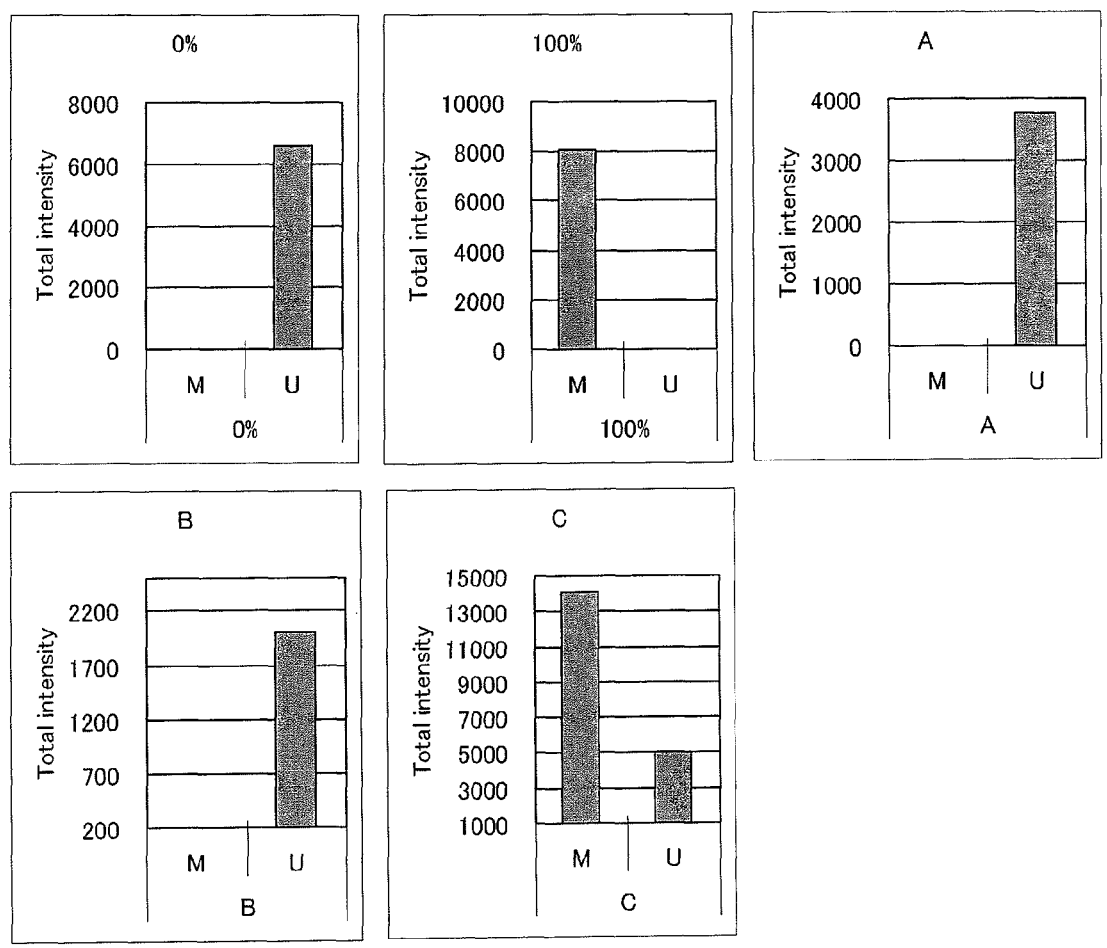
FIG. 23 is graphs showing band intensities of agarose gel electrophoresis after MSP using the primer set for STOX2 in Example 5.

FIG. 22 shows the results of agarose gel electrophoresis of MSP using the primer set for STOX2. FIG. 23 shows the graphs of band intensities of agarose gel electrophoresis of methylation specific PCR using the primer set for STOX2.

FIGS. 22 and 23 show that 100% methylation control sample and breast cancer specimen sample C resulted in stronger band intensities in PCR when the primers for detection of methylation were used than the primers for detection of non-methylation were used, while 0% methylation control sample, and normal mammary epithelial specimen samples A and B resulted in stronger band intensities in PCR when the primers for detection of non-methylation were used than the primers for detection of methylation were used. These results revealed that breast cancer cells can be detected by analyzing methylation status of STOX2 gene in biological samples by MSP.

What is claimed is:

1. A method for determination of presence or absence of cancer cells in a tissue obtained from a colon of a subject comprising the steps of:

extracting DNA from the tissue;

carrying out bisulfite treatment to the DNA obtained from the step of extracting;

amplifying DNA of a promoter region of COL4A2 by using the DNA from the bisulfite treatment step as a template, a first primer comprising the sequence of SEQ ID NO: 15 and a second primer comprising the sequence of SEQ ID NO: 16;

obtaining a peak from a methylated DNA fragment and a peak from a non-methylated DNA fragment of the promoter region of COL4A2 by analyzing the amplified DNA by mass spectrometry;

calculating a methylation rate of CpG sites in the promoter region of COL4A2 from an area ratio between a peak from the methylated DNA fragment and a peak from the non-methylated DNA fragment; and determining presence or absence of cancer cells in the tissue based on a comparison of the rate obtained from the step of calculating to a pre-determined cut-off value, and cancer cells are determined to be present in the tissue when the rate is higher than the cut-off value.

2. The method according to claim 1, wherein the methylation rate of CpG sites is calculated from the formula:

> area of the peak derived from the methylated DNA fragment/(area of the peak derived from the non-methylated DNA fragment+area of the peak derived from the methylated DNA fragment).

3. The method according to claim 1, further comprising fragmenting the DNA obtained from the step of extracting after the step of extracting.

4. The method according to claim 1, wherein the first primer has a tag sequence: 5'-AGGAAGAGAG-3' (SEQ ID NO: 133) at the 5' terminal of the first primer, and the second primer has a T7 promoter sequence: 5'-CAGTAATACGACTCACTATAGGGAGAAGGCT-3' (SEQ ID NO: 134) at the 5' terminal of the second primer.

\* \* \* \* \*